United States Patent
Kim et al.

(10) Patent No.: US 11,234,599 B2
(45) Date of Patent: *Feb. 1, 2022

(54) METHOD AND SYSTEMS FOR MEASURING NEURAL ACTIVITY

(71) Applicant: The Board of Trustees of the Leland Stanford Junior University, Stanford, CA (US)

(72) Inventors: Christina K. Kim, Stanford, CA (US); Samuel J. Yang, Stanford, CA (US); Karl A. Deisseroth, Stanford, CA (US); Isaac V. Kauvar, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/709,508

(22) Filed: Dec. 10, 2019

(65) Prior Publication Data

US 2020/0187780 A1    Jun. 18, 2020

Related U.S. Application Data

(63) Continuation of application No. 15/749,052, filed as application No. PCT/US2016/062314 on Nov. 16, 2016.

(60) Provisional application No. 62/257,140, filed on Nov. 18, 2015.

(51) Int. Cl.
*A61B 5/00* (2006.01)
*G01N 33/58* (2006.01)

(52) U.S. Cl.
CPC .......... *A61B 5/0071* (2013.01); *A61B 5/4064* (2013.01); *G01N 33/582* (2013.01); *A61B 5/0066* (2013.01); *A61B 5/0084* (2013.01); *A61B 5/6868* (2013.01)

(58) Field of Classification Search
CPC ... A61B 5/0071; A61B 5/4064; A61B 5/0066; A61B 5/0084; A61B 5/6868; G01N 33/582
See application file for complete search history.

(56) References Cited

U.S. PATENT DOCUMENTS

| | | |
|---|---|---|
| 2006/0054787 A1 | 3/2006 | Olsen et al. |
| 2009/0195896 A1 | 8/2009 | Tsai |
| 2014/0303504 A1 | 10/2014 | Stankovic et al. |

OTHER PUBLICATIONS

Morales-Delgado, Edgar E., Salma Farahi, Ioannis N. Papadopoulos, Demetri Psaltis, and Christophe Moser. "Delivery of focused short pulses through a multimode fiber." Optics express 23, No. 7 (2015): 9109-9120.*

(Continued)

*Primary Examiner* — Carolyn A Pehlke
(74) *Attorney, Agent, or Firm* — Rudy J. Ng; Bozicevic, Field & Francis LLP

(57) ABSTRACT

Provided herein is a method of optically recording neural activity in one or more regions of a target tissue. Also provided is a method of optically modulating the activity of a neural tissue. Further provided is a system that finds use in performing the present methods.

27 Claims, 38 Drawing Sheets

Specification includes a Sequence Listing.

(56) References Cited

OTHER PUBLICATIONS

Ma, Hongtao, et al. "Wide-field in vivo neocortical calcium dye imaging using a convection-enhanced loading technique combined with simultaneous multiwavelength imaging of voltage-sensitive dyes and hemodynamic signals." Neurophotonics 1, No. 1 (2014): 015003.*

Vanni, Matthieu P., and Timothy H. Murphy. "Mesoscale transcranial spontaneous activity mapping in GCaMP3 transgenic mice reveals extensive reciprocal connections between areas of somatomotor cortex." Journal of Neuroscience 34, No. 48 (2014): 15931-15946.*

Mahalati, Reza Nasiri, Ruo Yu Gu, and Joseph M. Kahn. "Resolution limits for imaging through multi-mode fiber." Optics express 21, No. 2 (2013): 1656-1668.*

Flusberg, Benjamin A., Eric D. Cocker, Wibool Piyawattanametha, Juergen C. Jung, Eunice LM Cheung, and Mark J. Schnitzer. "Fiber-optic fluorescence imaging." Nature methods 2, No. 12 (2005): 941-950.*

Dugue et al., (2014) "Optogenetic Recruitment of Dorsal Raphe Serotonergic Neurons Acutely Decreases Mechanosensory Responsivity in Behaving Mice," PLOS ONE, 9(8), e105941, p. 1-6.

Bootman et al., (2013) "Ca2+-Sensitive Fluorescent Dyes and Intracellular Ca2+ Imaging," Cold Spring Harbor Protocols: No. 2 p. 83-99.

Consalez & Hawkes (2013) "The compartmental restriction of cerebellar interneurons," Review Article, Frontiers in Neural Circuits: vol. 6 (123) p. 1-14.

Doric Lenses ((http://doriclenses.com/life-sciences/integrated-fluorescence-mini-cubes/1 098-5-v ports-gcamp-isosbestic-and-functi onal-exci tati ons-and-opsi n-activation. html#:-: text= The %20GCa M P %20isosbesti c%20poi nt%20is%20excited%20by% 20400%2D41 0%20nm,with%20580%2D650%20nm%20light, retrieved Jan. 16, 2021) 2 pages.

Guo et al., (2015) "Multi-channel fiber photometry for population neuronal activity recording," Biomedical Optics Express: vol. 6 No. 10, p. 3919-3931.

Sanderson et al., (2016) "Fluorescence Microscopy," Cold Spring Harbor protocols: vol. 2014 No. 10, p. 1-36.

Definitin of "synchronous" (https://www. thefreedictionary.com/synchronously, retrieved Jan. 16, 2021) p. 1.

Szabo et al., (2014) "Spatially Selective Holographic Photoactivation and Functional Fluorescence Imaging in Freely Behaving Mice with a Fiberscope," Neuron: 84, p. 1157-1169.

Venkatachalam and Cohen (2014) "Imaging GFP-Based Reporters in Neurons with Multiwavelength Optogenetic Control," Biophysical Journal: vol. 107 p. 1554-1563.

* cited by examiner

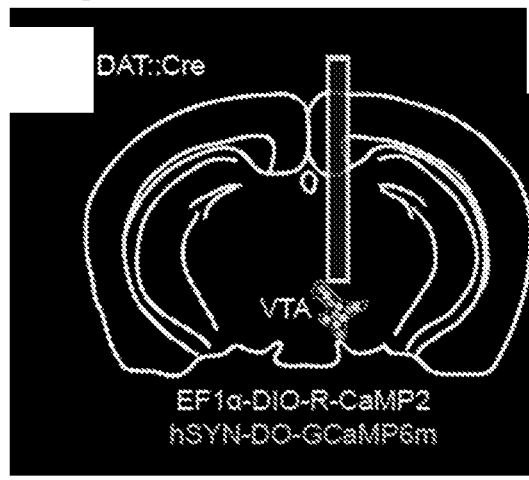
Fig. 2A
Fig. 2B
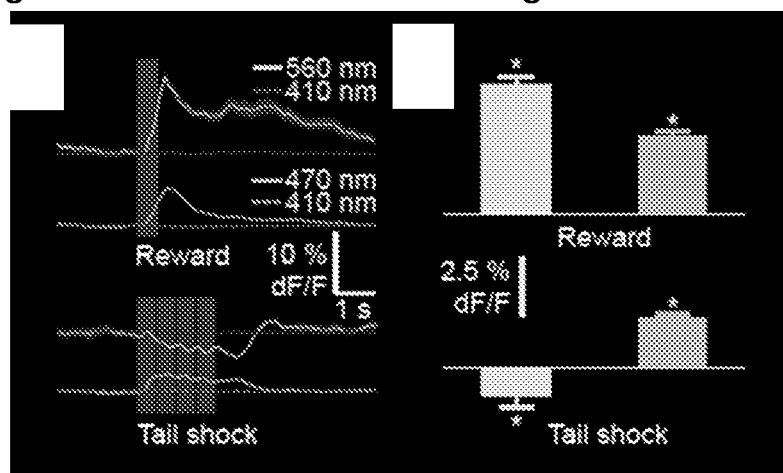
Fig. 2C
Fig. 2D

Fig. 3A
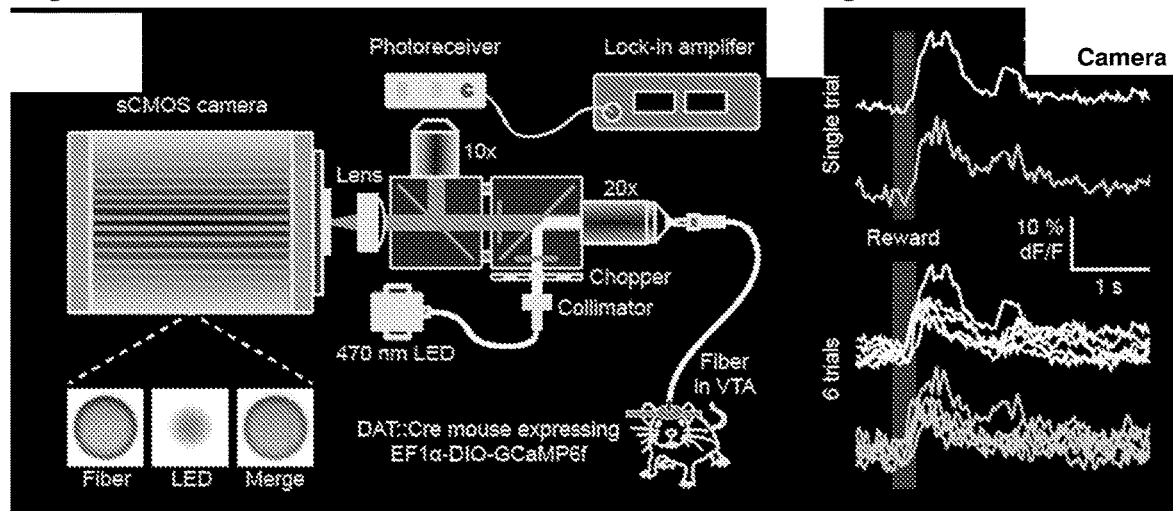
Fig. 3B
Fig. 3C
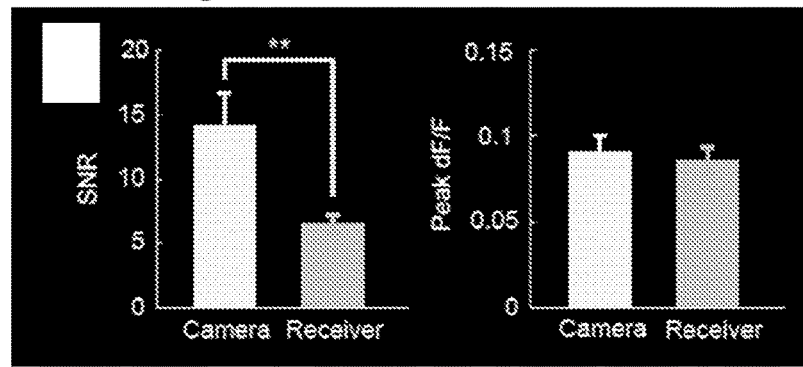

FIG. 12A

Amino acid sequence of ReaChR (SEQ ID NO:1)

MVSRRPWLLALALAVALAAGSAGASTGSDATVPVATQDGPDYVFHRAHER
MLFQTSYTLENNGSVICIPNNGQCFCLAWLKSNGTNAEKLAANILQWVVFA
LSVACLGWYAYQAWRATCGWEEVYVALIEMMKSIIEAFHEFDSPATLWLSSG
NGVVWMRYGEWLLTCPVILIHLSNLTGLKDDYSKRTMGLLVSDVGCIVWGA
TSAMCTGWTKILFFLISLSYGMYTYFHAAKVYIEAFHTVPKGLCRQLVRAM
AWLFFVSWGMFPVLFLLGPEGFGHISPYGSAIGHSILDLIAKNMWGVLGNYL
RVKIHEHILLYGDIRKKQKITIAGQEMEVETLVAEEEDKYESS

E = amino acid 163

FIG. 12B

Amino acid sequence of ReaChRE-S (SEQ ID NO:2)

MVSRRPWLLALALAVALAAGSAGASTGSDATVPVATQDGPDYVFHRAHER
MLFQTSYTLENNGSVICIPNNGQCFCLAWLKSNGTNAEKLAANILQWVVFA
LSVACLGWYAYQAWRATCGWEEVYVALIEMMKSIIEAFHEFDSPATLWLSSG
NGVVWMRYGSWLLTCPVILIHLSNLTGLKDDYSKRTMGLLVSDVGCIVWGA
TSAMCTGWTKILFFLISLSYGMYTYFHAAKVYIEAFHTVPKGLCRQLVRAM
AWLFFVSWGMFPVLFLLGPEGFGHISPYGSAIGHSILDLIAKNMWGVLGNYL
RVKIHEHILLYGDIRKKQKITIAGQEMEVETLVAEEEDKYESS

S = amino acid 163

FIG. 12C

Amino acid sequence of bReaChE-S (SEQ ID NO:3)

MDYGGALSAVGLFQTSYTLENNGSVICIPNNGQCFCLAWLKSNGTNAEKLA
ANILQWVVFALSVACLGWYAYQAWRATCGWEEVYVALIEMMKSIIEAFHEF
DSPATLWLSSGNGVVWMRYGSWLLTCPVILIHLSNLTGLKDDYSKRTMGLLV
SDVGCIVWGATSAMCTGWTKILFFLISLSYGMYTYFHAAKVYIEAFHTVPKG
LCRQLVRAMAWLFFVSWGMFPVLFLLGPEGFGHISPYGSAIGHSILDLIAKN
MWGVLGNYLRVKIHEHILLYGDIRKKQKITIAGQEMEVETLVAEEED

S = amino acid 123

FIG. 12D
bReaChE-S + trafficking sequence + ER export sequence (SEQ ID NO:4)
MDYGGALSAVGLFQTSYTLENNGSVICIPNNGQCFCLAWLKSNGTNAEKLA
ANILQWVVFALSVACLGWYAYQAWRATCGWEEVYVALIEMMKSIIEAFHEF
DSPATLWLSSGNGVVWMRYGSWLLTCPVILIHLSNLTGLKDDYSKRTMGLLV
SDVGCIVWGATSAMCTGWTKILFFLISLSYGMYTYFHAAKVYIEAFHTVPKG
LCRQLVRAMAWLFFVSWGMFPVLFLLGPEGFGHISPYGSAIGHSILDLIAKN
MWGVLGNYLRVKIHEHILLYGDIRKKQKITIAGQEMEVETLVAEEEDAAAKS
RITSEGEYIPLDQIDINVFCYENEV
S = amino acid 123
Grey highlight = trafficking sequence
Grey highlight and underlined = ER export sequence

FIG. 12E
Amino acid sequence of bReaChE-S no signal sequence (SEQ ID NO:5)
LFQTSYTLENNGSVICIPNNGQCFCLAWLKSNGTNAEKLAANILQWVVFALS
VACLGWYAYQAWRATCGWEEVYVALIEMMKSIIEAFHEFDSPATLWLSSGN
GVVWMRYGSWLLTCPVILIHLSNLTGLKDDYSKRTMGLLVSDVGCIVWGAT
SAMCTGWTKILFFLISLSYGMYTYFHAAKVYIEAFHTVPKGLCRQLVRAMA
WLFFVSWGMFPVLFLLGPEGFGHISPYGSAIGHSILDLIAKNMWGVLGNYLR
VKIHEHILLYGDIRKKQKITIAGQEMEVETLVAEEED
S = amino acid 112

FIG. 12F
Amino acid sequence of bReaChE-S no signal sequence + trafficking sequence + ER export (SEQ ID NO:6)
LFQTSYTLENNGSVICIPNNGQCFCLAWLKSNGTNAEKLAANILQWVVFALS
VACLGWYAYQAWRATCGWEEVYVALIEMMKSIIEAFHEFDSPATLWLSSGN
GVVWMRYGSWLLTCPVILIHLSNLTGLKDDYSKRTMGLLVSDVGCIVWGAT
SAMCTGWTKILFFLISLSYGMYTYFHAAKVYIEAFHTVPKGLCRQLVRAMA
WLFFVSWGMFPVLFLLGPEGFGHISPYGSAIGHSILDLIAKNMWGVLGNYLR
VKIHEHILLYGDIRKKQKITIAGQEMEVETLVAEEEDAAAKSRITSEGEYIPLD
QIDINVFCYENEV
S = amino acid 112
Grey highlight = trafficking sequence
Grey highlight and underlined = ER export sequence

FIG. 13A

GCaMPK (SEQ ID NO:7)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKYTDSEEEIGEAFRVFDKDGNGYISAAELR
HVMTNLGEKLTDEEVDEMIREADIDGDGQVNYEEFVQMMTAK

FIG. 13B

GCaMP2 (SEQ ID NO:8)
MRGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13C

GCaMP2.1 (SEQ ID NO:9)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13D

GCaMP2.2a (SEQ ID NO:10)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13E

GCaMP2.2b (SEQ ID NO:11)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQCKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13F

GCaMP2.3 (SEQ ID NO:12)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13G

GCaMP2.4 (SEQ ID NO:13)

MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13H

GCaMP3 (SEQ ID NO:14)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13I

GCaMP5g (SEQ ID NO:15)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYTDSEEEIREAFRVFDKDGNGYISAAELRHV
MTNLGEKLTDEEVDEMIREADIDGDGQVNYEEFVQMMTAK

FIG. 13J

GCaMP6m (SEQ ID NO:16)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKGSYRDTEEEIREAFGVFDKDGNGYISAAELRHV
MTNLGEKLTDEEVDEMIREADIDGDGQVNYEEFVQMMTAK

FIG. 13K

GCaMP6s (SEQ ID NO:17)

MGSHHHHHHGMASMTGGQQMGRDLYDDDDKDLATMVDSSRRKWNKTG
HAVRAIGRLSSLENVYIKADKQKNGIKANFHIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 13L

GCaMP6f (SEQ ID NO:18)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEEFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 13M

GEM-GECO1 (GenBank ID: JN258409) (SEQ ID NO:19)

MVDSSRRKWNKTGHAVRAIGRLSSPENVYIKADEQKNGIKAYFKIRHNIEGG
GVQLAYHYQQITPIGDGPVLLPDNHYLSVQSILSKDPNEKRDHMVLLEFVTA
AGITLGMDELYKGGSGGMVSKGEELFTGVVPIQVELDGDVNGHKFSVSGEG
EGDATYGKLTLKFICTTGKLPVPWPTLVTTLSYGVQCFSRYPDHMKQHDFFK
SAMPEGYIQERTIFFKDDGNYKTRAEVKFEGDTLVNRIELKGIDFKEDGNILG
HKLEYSTRDQLTEEQIAEFKEAFSLFDKDGDGTITTKELGTVMRSLGQNPTE
AELQDMINEVDADGDGTIDFPEFLTMMAPKMQDTDSEEEIREAFRVFDKDG
NGYIGAAELRHVMTNLGEKLTDEEVDEMIRVADIDGDGQVNYEEFVQMMT
AK

FIG. 13N

GEX-GECO1 (GenBank ID: JN258410) (SEQ ID NO:20)

MVDSSRRKWNKTGHAVRAIGRLSSLENVYIKADEQKNGIKANFKIRHNIEDG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLSYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAELKEAFSLFDKDGDGTITTKELGTVMRSLGQNP
TEAELQDMINEVDADGDGTIDLPEFQTMMARKMNDTDSEEEIREAFRVFDK
DGNGYIGAAELRHVMTNLGEKLTDEEVDEMIRVADIDGDGQVNYEEFVQM
MTAK

FIG. 13O

R-GECO1 (GenBank ID: JN258411) (SEQ ID NO:21)

MVDSSRRKWNKAGHAVRAIGRLSSPVVSERMYPEDGALKSEIKKGLRLKDG
GHYAAEVKTTYKAKKPVQLPGAYIVDIKLDIVSHNEDYTIVEQCERAEGRHS
TGGMDELYKGGTGGSLVSKGEEDNMAIIKEFMRFKVHMEGSVNGHEFEIEG
EGEGRPYEAFQTAKLKVTKGGPLPFAWDILSPQFMYGSKAYIKHPADIPDYF
KLSFPEGFRWERVMNFEDGGIIHVNQDSSLQDGVFIYKVKLRGTNFPPDGPV
MQKKTMGWEATRDQLTEEQIAEFKEAFSLFDKDGDGTITTKELGTVMRSLG
QNPTEAELQDMINEVDADGDGTFDFPEFLTMMARKMNDTDSEEEIREAFRV
FDKDGNGYIGAAELRHVMTDLGEKLTDEEVDEMIRVADIDGDGQVNYEEFV
QMMTAK

FIG. 13P

B-GECO1 (GenBank ID: JN258412) (SEQ ID NO:22)

MVDSPRRKWNKTGHAVRAIGRLSSPENVYIKADKQKNGIKANFKIRHNIEG
GGVQLAYHYQQNTPIGDGPVLLPDNHYLSVQSILSKDPNEKRDHMVLLEFV
TAAGITLGMDELYKGGTGGSESMVSKGEELFTGVVPIQVELDGDVNGHKFS
VSGEGEGDATYGKLTLKFICTTGKLPVPWPTLVTTLSHGVQCFSRYPDHMKQ
HDFFKSAMPGGYIQERTIFFKDDGNYKTRAEVKFEGDTLVNRIELKGIDFKED
GNILGHKLEYNTRGQLTEEQIAEFKEAFSLFDKDGDGTITTKELGTVMRSLG
QNPTEAELQDMINEVDADGDGTIDFPEFLTMMAPKMQDTDSEEEIREAFRVF
DKDGNGYIGAAELRHVMTNLGEKLTDEEVDEMIREADIDGDGQVNYEEFV
QMMTAK

FIG. 13Q

G-GECO1 (GenBank ID: JN258413) (SEQ ID NO:23)
MVDSSRRKWNKTGHAVRAIGRLSSLENVYIKADKQKNGIKANFKIRHNIED
GGVQLAYHYQQNTPIGDGPVLLPDNHYLSVQSILSKDPNEKRDHMVLLEFV
TAAGITLGMDELYKGGTGGSMVSKGEELFTGVVPIQVELDGDVNGHKFSVS
GEGEGDATYGKLTLKFICTTGKLPVPWPTLVTTLTYGVQCFSRYPDHMKQHD
FFKSAMPEGYIQERTIFFKDDGNYKTRAEVKFEGDTLVNRIELKGIDFKEDGN
ILGHKLEYNTRDQLTEEQIAEFKEAFSLFDKDGDGTITTKELGTVMRSLGQNP
TEAELQDMINEVDADGDGTIDFPEFLTMMARKMKDTDSEEEIREAFRVFDK
DGNGYIGAAELRHVMTNLGEKLTDEEVDEMIRVADIDGDGQVNYEEFVQM
MTAK

FIG. 13R

G-GECO1.1 (GenBank ID: JN258414) (SEQ ID NO:24)
MVDSSRRKWNKTGHAVRAIGRLSSLENVYIKADEQKNGIKAYFKIRHNIEGG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLTYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAEFKEAFSLFDKDGDGTITTKELGTVMRSLGQNP
TEAELQDMINEVDADGDGTIDFPEFLTMMARKMNDTDSEEEIREAFRVFDK
DGNGYIGAAELRHVMTNLGEKLTDEEVDEMIRVADIDGDGQVNYEEFVQM
MTAK

FIG. 13S

G-GECO1.2 (GenBank ID: JN258415) (SEQ ID NO:25)
MVDSSRRKWNKTGHAVRAIGRLSSLENVYIKADEQKNGIKAYFKIRHNIEGG
GVQLAYHYQQNTPIGDGPVLLPDNHYLSVQSMLSKDPNEKRDHMVLLEFVT
AAGITLGMDELYKGGTGGSESMVSKGEELFTGVVPIQVELDGDVNGHKFSV
SGEGEGDATYGKLTLKFICTTGKLPVPWPTLVTTLTYGVQCFSRYPDHMKQH
DFFKSAMPEGYIQERTIFFKGDGNYKTRAEVKFEGDTLVNRIELKGIDFKEDG
NILGHKLEYNTRDQLTEEQIAEFKEAFSLFDKDGDGTITTKELGTVMRSLGQ
NPTEAELQDMINEVDADGDGTIDFPEFLTMMARKMKDTDSEEEIREAFRVFD
KDGNGYIGAAELRHVMTNLGEKLTDEEVDEMIRVADIDGDGQVNYEEFVQ
MMTAK

FIG. 14A

TN-XXL (SEQ ID NO:26)

MVSKGEELFTGVVPILVELDGDVNGHKFSVRGEGEGDATNGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSK
LSKDPNEKRDHMVLLEFVTAARMLSEEELANCFRIFDKDANGFIDIEELGEIL
RATGEHVTEEDIEDLMKDSDKNNDGRIDFDEFLKMMEGVQGTSEEELANCF
RIFDKDANGFIDIEELGEILRATGEHVTEEDIEDLMKDSDKNNDGRIDFDEFL
KMMEGVQELMGGVQLADHYQQNTPIGDGPVLLPDNHYLSYQSKLSKDPNE
KRDHMVLLEFVTAAGITLGMDELYKGGTGGSMVSKGEELFTGVVPILVELD
GDVNGHKFSVRGEGEGDATNGKLTLKFICTTGKLPVPWPTLVTTLGYGLMC
FARYPDHMKQHDFFKSAMPEGYVQERTIFFKDDGNYKTRAEVKFEGDTLVN
RIELKGIDFKEDGNILGHKLEYNYNSHNVYIMADKQKNGIKANFKIRHNIED

FIG. 14B

YC3.6 (SEQ ID NO:27)

MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLFDKDGDGTITT
KELGTVMRSLGQNPTEAELQDMINEVDADGNGTIYFPEFLTMMARKMKDT
DSEEEIREAFRVFDKDGNGYISAAQLRHVMTNLGEKLTDEEVDEMIREADID
GDGQVNYEEFVQMMTAKGGKRRWKKNFIAVSAANRFKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIELSRGPGTSAEIYACRLE
ISN

FIG. 14C

D3CPVenus polypeptide (SEQ ID NO:28)
MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLLDKDGDGTITT
KELGTALRSLGQNPTEAELQDMINEVDADGNGTIYFPEFLTMMARKMKDTD
SEEEIREAFRVFDKDGNGYISAAELRHVMTNLGEKLTDEEVDEMIREADIDG
DGQVNYEEFVQMMTAKGGKRRWQKTGHAVRAFGRLKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIE

FIG. 15A

Amino acid sequence of ChR1 (SEQ ID NO:29)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGICRDLVRYLAWLYFCSW
AMFPVLFLLGPEGFGHINQFNSAIAHAILDLASKNAWSMMGHFLRVKIHEHI
LLYGDIRKKQKVNVAGQEMEVETMVHEEDD

FIG. 15B

Amino acid sequence of ChR2 (SEQ ID NO:30)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTCPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 15C

Amino acid sequence of ChR2 SFO (SEQ ID NO:31)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 15D

Amino acid sequence of ChR2 SSFO (SEQ ID NO:32)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SAIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 15E

Amino acid sequence of VChR1 (SEQ ID NO:33)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 15F

Amino acid sequence of VChR1 SFO (SEQ ID NO:34)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTSPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 15G

Amino acid sequence of VChR1 SSFO (SEQ ID NO:35)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSAVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 15H

Amino acid sequence of C1V1 (SEQ ID NO:36)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVLLIHLSNLTGLKDDYSKRTMGLLVSDVGCIVWGATSAMCT
GWTKILFFLISLSYGMYTYFHAAKVYIEAFHTVPKGICRELVRVMAWTFFVA
WGMFPVLFLLGTEGFGHISPYGSAIGHSILDLIAKNMWGVLGNYLRVKIHEH
ILLYGDIRKKQKITIAGQEMEVETLVAEEED

FIG. 15I

Amino acid sequence of C1C2 (SEQ ID NO:37)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVS
WGMFPILFILGPEGFGVLSVYGSTVGHTIIDLMSKNCWGLLGHYLRVLIHEHI
LIHGDIRKTTKLNIGGTEIEVETLVEDEAEAGAV

FIG. 15J
Amino acid sequence of SdChR (SEQ ID NO:38)
MGGAPAPDAHSAPPGNDSAGGSEYHAPAGYQVNPPYHPVHGYEEQCSSIYI
YYGALWEQETARGFQWFAVFLSALFLAFYGWHAYKASVGWEEVYVCSVEL
IKVILEIYFEFTSPAMLFLYGGNITPWLRYAEWLLTCPVILIHLSNITGLSEEYN
KRTMALLVSDLGTICMGVTAALATGWVKWLFYCIGLVYGTQTFYNAGIIYV
ESYYIMPAGGCKKLVLAMTAVYYSSWLMFPGLFIFGPEGMHTLSVAGSTIGH
TIADLLSKNIWGLLGHFLRIKIHEHIIMYGDIRRPVSSQFLGRKVDVLAFVTEE
DKV

FIG. 15K
Amino acid sequence of CnChR2 (SEQ ID NO:39)
MEPVLGLASTAVRELTAGGSGNPYESYKPPEDPCALTPFGCLTNFWCDPQFG
LADAKYDYCYVKAAYGELAIVETSRLPWLYSHGSDAEHQGALAMQWMAF
ALCIICLVFYAYHSWKATTGWEEVYVCVVELVKVLLEIYKEFESPASIYLPTA
NAALWLRYGEWLLTCPVILIHLSNITGLKDDYNKRTMQLLVSDIGCVVWGIT
AAFSVGWLKWVFFVLGLLYGSNTYFHAAKVYIESYHTVPKGHCRLIVRLMA
YCFYVAWTMYPILFILGPEGLGHMSAYMSTALHGVADMLSKQIWGLLGHHL
RVKIFEHILIHGDIRKTTTMQVGGQMVQVEEMVDEEDEDTI

FIG. 15L
Amino acid sequence of CsChrimson (SEQ ID NO:40)
MSRLVAASWLLALLLCGITSTTTASSAPAASSTDGTAAAAVSHYAMNGFDEL
AKGAVVPEDHFVCGPADKCYCSAWLHSRGTPGEKIGAQVCQWIAFSIAIALL
TFYGFSAWKATCGWEEVYVCCVEVLFVTLEIFKEFSSPATVYLSTGNHAYCL
RYFEWLLSCPVILIKLSNLSGLKNDYSKRTMGLIVSCVGMIVFGMAAGLATD
WLKWLLYIVSCIYGGYMYFQAAKCYVEANHSVPKGHCRMVVKLMAYAYF
ASWGSYPILWAVGPEGLLKLSPYANSIGHSICDIIAKEFWTFLAHHLRIKIHEHI
LIHGDIRKTTKMEIGGEEVEVEEFVEEEDEDTV

FIG. 15M

Amino acid sequence of ShChR1 (SEQ ID NO:41)

METAATMTHAFISAVPSAEATIRGLLSAAAVVTPAADAHGETSNATTAGADH
GCFPHINHGTELQHKIAVGLQWFTVIVAIVQLIFYGWHSFKATTGWEEVYVC
VIELVKCFIELFHEVDSPATVYQTNGGAVIWLRYSMWLLTCPVILIHLSNLTGL
HEEYSKRTMTILVTDIGNIVWGITAAFTKGPLKILFFMIGLFYGVTCFFQIAKV
YIESYHTLPKGVCRKICKIMAYVFFCSWLMFPVMFIAGHEGLGLITPYTSGIG
HLILDLISKNTWGFLGHHLRVKIHEHILIHGDIRKTTTINVAGENMEIETFVDE
EEEGGV

FIG. 15N

Amino acid sequence of Arch (SEQ ID NO:42)

MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAAD

FIG. 15O

Amino acid sequence of ArchT (SEQ ID NO:43)

MDPIALQAGYDLLGDGRPETLWLGIGTLLMLIGTFYFIVKGWGVTDKEARE
YYSITILVPGIASAAYLSMFFGIGLTEVTVAGEVLDIYYARYADWLFTTPLLLL
DLALLAKVDRVSIGTLVGVDALMIVTGLIGALSHTPLARYSWWLFSTICMIV
VLYFLATSLRAAAKERGPEVASTFNTLTALVLVLWTAYPILWIIGTEGAGVVGL
GIETLLFMVLDVTAKVGFGFILLRSRAILGDTEAPEP

FIG. 15P

Amino acid sequence of GtR3 (SEQ ID NO:44)
ASSFGKALLEFVFIVFACITLLLGINAAKSKAASRVLFPATFVTGIASIAYFSMA
SGGGWVIAPDCRQLFVARYLDWLITTPLLLIDLGLVAGVSRWDIMALCLSDV
LMIATGAFGSLTVGNVKWVWWFFGMCWFLHIIFALGKSWAEAAKAKGGDS
ASVYSKIAGITVITWFCYPVVWVFAEGFGNFSVTFEVLIYGVLDVISKAVFGLI
LMSGAATGYESI

FIG. 15Q

Amino acid sequence of Oxy (SEQ ID NO:45)
MAPLAQDWTYAEWSAVYNALSFGIAGMGSATIFFWLQLPNVTKNYRTALTIT
GIVTLIATYHYFRIFNSWVAAFNVGLGVNGAYEVTVSGTPFNDAYRYVDWLL
TVPLLLVELILVMKLPAKETVCLAWTLGIASAVMVALGYPGEIQDDLSVRWF
WWACAMVPFVYVVGTLVVGLGAATAKQPEGVVDLVSAARYLTVVSWLTYP
FVYIVKNIGLAGSTATMYEQIGYSAADVTAKAVFGVLIWAIANAKSRLEEEG
KLRA

FIG. 15R

Amino acid sequence of Mac (SEQ ID NO:46)
MIVDQFEEVLMKTSQLFPLPTATQSAQPTHVAPVPTVLPDTPIYETVGDSGSK
TLWVVFVLMLIASAAFTALSWKIPVNRRLYHVITTIITLTAALSYFAMATGHG
VALNKIVIRTQHDHVPDTYETVYRQVYYARYIDWAITTPLLLLDLGLLAGMS
GAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYA
VLDVLAKGVFGAWLLVTHANLRESDVELNGFWANGLNREGAIRIGEDDGA

FIG. 15S

Amino acid sequence of NpHR (SEQ ID NO:47)

VTQRELFEFVLNDPLLASSLYINIALAGLSILLFVFMTRGLDDPRAKLIAVSTIL
VPVVSIASYTGLASGLTISVLEMPAGHFAEGSSVMLGGEEVDGVVTMWGRY
LTWALSTPMILLALGLLAGSNATKLFTAITFDIAMCVTGLAAALTTSSHLMRW
FWYAISCACFLVVLYILLVEWAQDAKAAGTADMFNTLKLLTVVMWLGYPIV
WALGVEGIAVLPVGVTSWGYSFLDIVAKYIFAFLLLNYLTSNESVVSGSILDV
PSASGTPADD

FIG. 15T

Amino acid sequence of DsChR (SEQ ID NO:48)

MRRRESQLAYLCLFVLIAGWAPRLTESAPDLAERRPPSERNTPYANIKKVPNI
TEPNANVQLDGWALYQDFYYLAGSDKEWVVGPSDQCYCRAWSKSHGTDR
EGEAAVVWAYIVFAICIVQLVYFMFAAWKATVGWEEVYVNIIELVHIALVIWV
EFDKPAMLYLNDGQMVPWLRYSAWLLSCPVILIHLSNLTGLKGDYSKRTMG
LLVSDIGTIVFGTSAALAPPNHVKVILFTIGLLYGLFTFFTAAKVYIEAYHTVP
KGQCRNLVRAMAWTYFVSWAMFPILFILGREGFGHITYFGSSIGHFILEIFSKN
LWSLLGHGLRYRIRQHIIIHGNLTKKNKINIAGDNVEVEEYVDSNDKDSDV

FIG. 15U

Amino acid sequence of Champ (SEQ ID NO:49)
MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAADKSRITSE
GEYIPLDQIDINVGAPGSGATNFSLLKQAGDVEENPGPMDLKESPSEGSLQPS
SIQIFANTSTLHGIRHIFVYGPLTIRRVLWAVAFVGSLGLLLVESSERVSYYFSY
QHVTKVDEVVAQSLVFPAVTLCNLNGFRFSRLTTNDLYHAGELLALLDVNLQ
IPDPHLADPTVLEALRQKANFKHYKPKQFSMLEFLHRVGHDLKDMMLYCKF
KGQECGHQDFTTVFTKYGKCYMFNSGEDGKPLLTTVKGGTGNGLEIMLDIQ
QDEYLPIWGETEETTFEAGVKVQIHSQSEPPFIQELGFGVAPGFQTFVATQEQR
LTYLPPPWGECRSSEMGLDFFPVYSITACRIDCETRYIVENCNCRMVHMPGD
APFCTPEQHKECAEPALGLLAEKDSNYCLCRTPCNLTRYNKELSMVKIPSKTS
AKYLEKKFNKSEKYISENILVLDIFFEALNYETIEQKKAYEVAALLGDIGGQM
GLFIGASLLTILELFDYIYELIKEKLLDLLGKEEEEGSHDENMSTCDTMPNHSE
TISHTVNVPLQTALGTLEEIACAAAKSRITSEGEYIPLDQIDINVVSKGEELFTG
VVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVK
FEGDTLVNRIELKGIDFREDGNILGHKLEYNYNSHNVYIMADKQKNGIKVNF
KIRHNIEDGSVQLADHYQQNTPIGDGPVLLPDNHYLSYQSALSKDPNEKRDH
MVLLEFVTAAGITLGMDELYKFCYENEV

SEQUENCE LISTING

<160> NUMBER OF SEQ ID NOS: 49

<210> SEQ ID NO 1
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 1

```
Met Val Ser Arg Arg Pro Trp Leu Leu Ala Leu Ala Leu Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
                100                 105                 110

Gln Ala Trp Arg Ala Thr Cys Gly Trp Glu Val Tyr Val Ala Leu
        115                 120                 125

Ile Glu Met Met Lys Ser Ile Ile Glu Ala Phe His Glu Phe Asp Ser
        130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
        290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
                340                 345                 350

<210> SEQ ID NO 2
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 2

Met Val Ser Arg Arg Pro Trp Leu Leu Ala Leu Ala Leu Val Ala
1               5                   10                  15
```

```
Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
 50                  55                  60

Val Ile Cys Ile Pro Asn Asn Gly Gln Cys Phe Cys Leu Ala Trp Leu
 65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Ser Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
            340                 345                 350

<210> SEQ ID NO 3
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 3

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30
```

```
Gln Cys Phe Cys Leu Ala Trp Leu Lys Ser Asn Gly Thr Asn Ala Glu
         35                  40                  45
Lys Leu Ala Ala Asn Ile Leu Gln Trp Val Val Phe Ala Leu Ser Val
 50                  55                  60
Ala Cys Leu Gly Trp Tyr Ala Tyr Gln Ala Trp Arg Ala Thr Cys Gly
 65                  70                  75                  80
Trp Glu Glu Val Tyr Val Ala Leu Ile Glu Met Met Lys Ser Ile Ile
                 85                  90                  95
Glu Ala Phe His Glu Phe Asp Ser Pro Ala Thr Leu Trp Leu Ser Ser
             100                 105                 110
Gly Asn Gly Val Val Trp Met Arg Tyr Gly Ser Trp Leu Leu Thr Cys
         115                 120                 125
Pro Val Ile Leu Ile His Leu Ser Asn Leu Thr Gly Leu Lys Asp Asp
130                 135                 140
Tyr Ser Lys Arg Thr Met Gly Leu Leu Val Ser Asp Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
            180                 185                 190
Ala Lys Val Tyr Ile Glu Ala Phe His Thr Val Pro Lys Gly Leu Cys
        195                 200                 205
Arg Gln Leu Val Arg Ala Met Ala Trp Leu Phe Phe Val Ser Trp Gly
210                 215                 220
Met Phe Pro Val Leu Phe Leu Leu Gly Pro Glu Gly Phe Gly His Ile
225                 230                 235                 240
Ser Pro Tyr Gly Ser Ala Ile Gly His Ser Ile Leu Asp Leu Ile Ala
                245                 250                 255
Lys Asn Met Trp Gly Val Leu Gly Asn Tyr Leu Arg Val Lys Ile His
            260                 265                 270
Glu His Ile Leu Leu Tyr Gly Asp Ile Arg Lys Lys Gln Lys Ile Thr
        275                 280                 285
Ile Ala Gly Gln Glu Met Glu Val Glu Thr Leu Val Ala Glu Glu Glu
290                 295                 300
Asp
305

<210> SEQ ID NO 4
<211> LENGTH: 335
<212> TYPE: PRT
<213> ORGANISM: Artificial sequence
<220> FEATURE:
<223> OTHER INFORMATION: Synthetic polypeptide

<400> SEQUENCE: 4

Met Asp Tyr Gly Gly Ala Leu Ser Ala Val Gly Leu Phe Gln Thr Ser
1                5                  10                  15
Tyr Thr Leu Glu Asn Asn Gly Ser Val Ile Cys Ile Pro Asn Asn Gly
             20                  25                  30
Gln Cys Phe Cys Leu Ala Trp Leu Lys Ser Asn Gly Thr Asn Ala Glu
         35                  40                  45
Lys Leu Ala Ala Asn Ile Leu Gln Trp Val Val Phe Ala Leu Ser Val
 50                  55                  60
Ala Cys Leu Gly Trp Tyr Ala Tyr Gln Ala Trp Arg Ala Thr Cys Gly
 65                  70                  75                  80
```

Trp Glu Glu Val Tyr Val Ala Leu Ile Glu Met Met Lys Ser Ile Ile
            85                  90                  95

Glu Ala Phe His Glu Phe Asp Ser Pro Ala Thr Leu Trp Leu Ser Ser
        100                 105                 110

Gly Asn Gly Val Val Trp Met Arg Tyr Gly Ser Trp Leu Leu Thr Cys
        115                 120                 125

Pro Val Ile Leu Ile His Leu Ser Asn Leu Thr Gly Leu Lys Asp Asp
        130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
        210                 215                 220

Met Phe Pro Val Leu Phe Leu Leu Gly Pro Glu Gly Phe Gly His Ile
225                 230                 235                 240

Ser Pro Tyr Gly Ser Ala Ile Gly His Ser Ile Leu Asp Leu Ile Ala
                245                 250                 255

Lys Asn Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
        290                 295                 300

Asp Ala Ala Ala Lys Ser Arg Ile Thr Ser Glu Gly Glu Tyr Ile Pro
305                 310                 315                 320

Leu Asp Gln Ile Asp Ile Asn Val Phe Cys Tyr Glu Asn Glu Val
                325                 330                 335

<210> SEQ ID NO 5
<211> LENGTH: 294
<212> TYPE: PRT
<213> ORGANISM: Artificial sequence
<220> FEATURE:
<223> OTHER INFORMATION: Synthetic polypeptide

<400> SEQUENCE: 5

Leu Phe Gln Thr Ser Tyr Thr Leu Glu Asn Asn Gly Ser Val Ile Cys
1               5                   10                  15

Ile Pro Asn Asn Gly Gln Cys Phe Cys Leu Ala Trp Leu Lys Ser Asn
            20                  25                  30

Gly Thr Asn Ala Glu Lys Leu Ala Ala Asn Ile Leu Gln Trp Val Val
        35                  40                  45

Phe Ala Leu Ser Val Ala Cys Leu Gly Trp Tyr Ala Tyr Gln Ala Trp
    50                  55                  60

Arg Ala Thr Cys Gly Trp Glu Glu Val Tyr Val Ala Leu Ile Glu Met
65                  70                  75                  80

Met Lys Ser Ile Ile Glu Ala Phe His Glu Phe Asp Ser Pro Ala Thr
                85                  90                  95

Leu Trp Leu Ser Ser Gly Asn Gly Val Val Trp Met Arg Tyr Gly Ser
            100                 105                 110

```
Trp Leu Leu Thr Cys Pro Val Ile Leu Ile His Leu Ser Asn Leu Thr
            115                 120                 125

Gly Leu Lys Asp Asp Tyr Ser Lys Arg Thr Met Gly Leu Leu Val Ser
130                 135                 140

Asp Val Gly Cys Ile Val Trp Gly Ala Thr Ser Ala Met Cys Thr Gly
145                 150                 155                 160

Trp Thr Lys Ile Leu Phe Phe Leu Ile Ser Leu Ser Tyr Gly Met Tyr
                165                 170                 175

Thr Tyr Phe His Ala Ala Lys Val Tyr Ile Glu Ala Phe His Thr Val
            180                 185                 190

Pro Lys Gly Leu Cys Arg Gln Leu Val Arg Ala Met Ala Trp Leu Phe
        195                 200                 205

Phe Val Ser Trp Gly Met Phe Pro Val Leu Phe Leu Leu Gly Pro Glu
    210                 215                 220

Gly Phe Gly His Ile Ser Pro Tyr Gly Ser Ala Ile Gly His Ser Ile
225                 230                 235                 240

Leu Asp Leu Ile Ala Lys Asn Met Trp Gly Val Leu Gly Asn Tyr Leu
                245                 250                 255

Arg Val Lys Ile His Glu His Ile Leu Leu Tyr Gly Asp Ile Arg Lys
            260                 265                 270

Lys Gln Lys Ile Thr Ile Ala Gly Gln Glu Met Glu Val Glu Thr Leu
        275                 280                 285

Val Ala Glu Glu Glu Asp
    290

<210> SEQ ID NO 6
<211> LENGTH: 324
<212> TYPE: PRT
<213> ORGANISM: Artificial sequence
<220> FEATURE:
<223> OTHER INFORMATION: Synthetic polypeptide

<400> SEQUENCE: 6

Leu Phe Gln Thr Ser Tyr Thr Leu Glu Asn Asn Gly Ser Val Ile Cys
1               5                   10                  15

Ile Pro Asn Asn Gly Gln Cys Phe Cys Leu Ala Trp Leu Lys Ser Asn
            20                  25                  30

Gly Thr Asn Ala Glu Lys Leu Ala Ala Asn Ile Leu Gln Trp Val Val
        35                  40                  45

Phe Ala Leu Ser Val Ala Cys Leu Gly Trp Tyr Ala Tyr Gln Ala Trp
    50                  55                  60

Arg Ala Thr Cys Gly Trp Glu Glu Val Tyr Val Ala Leu Ile Glu Met
65                  70                  75                  80

Met Lys Ser Ile Ile Glu Ala Phe His Glu Phe Asp Ser Pro Ala Thr
                85                  90                  95

Leu Trp Leu Ser Ser Gly Asn Gly Val Val Trp Met Arg Tyr Gly Ser
            100                 105                 110

Trp Leu Leu Thr Cys Pro Val Ile Leu Ile His Leu Ser Asn Leu Thr
        115                 120                 125

Gly Leu Lys Asp Asp Tyr Ser Lys Arg Thr Met Gly Leu Leu Val Ser
130                 135                 140

Asp Val Gly Cys Ile Val Trp Gly Ala Thr Ser Ala Met Cys Thr Gly
145                 150                 155                 160

Trp Thr Lys Ile Leu Phe Phe Leu Ile Ser Leu Ser Tyr Gly Met Tyr
                165                 170                 175
```

```
Thr Tyr Phe His Ala Ala Lys Val Tyr Ile Glu Ala Phe His Thr Val
            180                 185                 190

Pro Lys Gly Leu Cys Arg Gln Leu Val Arg Ala Met Ala Trp Leu Phe
        195                 200                 205

Phe Val Ser Trp Gly Met Phe Pro Val Leu Phe Leu Leu Gly Pro Glu
    210                 215                 220

Gly Phe Gly His Ile Ser Pro Tyr Gly Ser Ala Ile Gly His Ser Ile
225                 230                 235                 240

Leu Asp Leu Ile Ala Lys Asn Met Trp Gly Val Leu Gly Asn Tyr Leu
                245                 250                 255

Arg Val Lys Ile His Glu His Ile Leu Leu Tyr Gly Asp Ile Arg Lys
            260                 265                 270

Lys Gln Lys Ile Thr Ile Ala Gly Gln Glu Met Glu Val Glu Thr Leu
        275                 280                 285

Val Ala Glu Glu Asp Ala Ala Lys Ser Arg Ile Thr Ser Glu
    290                 295                 300

Gly Glu Tyr Ile Pro Leu Asp Gln Ile Asp Ile Asn Val Phe Cys Tyr
305                 310                 315                 320

Glu Asn Glu Val

<210> SEQ ID NO 7
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 7

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
```

```
                 210                 215                 220
Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
        370                 375                 380

Glu Glu Ile Gly Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 8
<211> LENGTH: 451
<212> TYPE: PRT
<213> ORGANISM: Artificial sequence
<220> FEATURE:
<223> OTHER INFORMATION: Synthetic polypeptide

<400> SEQUENCE: 8

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Leu Ala Thr Met Val Asp Ser Ser Arg Arg Lys Trp Asn Lys Thr Gly
        35                  40                  45

His Ala Val Arg Ala Ile Gly Arg Leu Ser Ser Leu Glu Asn Val Tyr
    50                  55                  60

Ile Met Ala Asp Lys Gln Lys Asn Gly Ile Lys Ala Asn Phe Lys Ile
65                  70                  75                  80

Arg His Asn Ile Glu Asp Gly Gly Val Gln Leu Ala Tyr His Tyr Gln
                85                  90                  95

Gln Asn Thr Pro Ile Gly Asp Gly Pro Val Leu Leu Pro Asp Asn His
            100                 105                 110

Tyr Leu Ser Thr Gln Ser Lys Leu Ser Lys Asp Pro Asn Glu Lys Arg
```

```
            115                 120                 125
Asp His Met Val Leu Glu Phe Val Thr Ala Ala Gly Ile Thr Leu
    130                 135                 140

Gly Met Asp Glu Leu Tyr Lys Gly Gly Thr Gly Ser Met Val Ser
145                 150                 155                 160

Lys Gly Glu Glu Leu Phe Thr Gly Val Val Pro Ile Leu Val Glu Leu
                165                 170                 175

Asp Gly Asp Val Asn Gly His Lys Phe Ser Val Ser Gly Glu Gly Glu
                180                 185                 190

Gly Asp Ala Thr Tyr Gly Lys Leu Thr Leu Lys Phe Ile Cys Thr Thr
            195                 200                 205

Gly Lys Leu Pro Val Pro Trp Pro Thr Leu Val Thr Thr Leu Thr Tyr
210                 215                 220

Gly Val Gln Cys Phe Ser Arg Tyr Pro Asp His Met Lys Gln His Asp
225                 230                 235                 240

Phe Phe Lys Ser Ala Met Pro Glu Gly Tyr Ile Gln Glu Arg Thr Ile
                245                 250                 255

Phe Phe Lys Asp Asp Gly Asn Tyr Lys Thr Arg Ala Glu Val Lys Phe
                260                 265                 270

Glu Gly Asp Thr Leu Val Asn Arg Ile Glu Leu Lys Gly Ile Asp Phe
            275                 280                 285

Lys Glu Asp Gly Asn Ile Leu Gly His Lys Leu Glu Tyr Asn Thr Arg
290                 295                 300

Asp Gln Leu Thr Glu Glu Gln Ile Ala Glu Phe Lys Glu Ala Phe Ser
305                 310                 315                 320

Leu Phe Asp Lys Asp Gly Asp Gly Thr Ile Thr Thr Lys Glu Leu Gly
                325                 330                 335

Thr Val Met Arg Ser Leu Gly Gln Asn Pro Thr Glu Ala Glu Leu Gln
            340                 345                 350

Asp Met Ile Asn Glu Val Asp Ala Asp Gly Asn Gly Thr Ile Asp Phe
            355                 360                 365

Pro Glu Phe Leu Thr Met Met Ala Arg Lys Met Lys Asp Thr Asp Ser
370                 375                 380

Glu Glu Glu Ile Arg Glu Ala Phe Arg Val Phe Asp Lys Asp Gly Asn
385                 390                 395                 400

Gly Tyr Ile Ser Ala Ala Glu Leu Arg His Val Met Thr Asn Leu Gly
                405                 410                 415

Glu Lys Leu Thr Asp Glu Glu Val Asp Glu Met Ile Arg Glu Ala Asp
            420                 425                 430

Ile Asp Gly Asp Gly Gln Val Asn Tyr Glu Glu Phe Val Gln Met Met
            435                 440                 445

Thr Ala Lys
    450

<210> SEQ ID NO 9
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 9

Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
```

```
                    20                  25                  30
Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445
```

Ala Lys
    450

<210> SEQ ID NO 10
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 10

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Arg Arg Lys Trp Asn Lys Thr Gly His
            35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

```
Met Ile Asn Glu Val Asp Ala Asp Gly Asn Gly Thr Ile Asp Phe Pro
            355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 11
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 11

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Cys Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255
```

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
            325                 330                 335

Val Met Arg Ser Leu Gly Gln Asn Pro Thr Glu Ala Glu Leu Gln Asp
        340                 345                 350

Met Ile Asn Glu Val Asp Ala Asp Gly Asn Gly Thr Ile Asp Phe Pro
    355                 360                 365

Glu Phe Leu Thr Met Met Ala Arg Lys Met Lys Asp Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
    435                 440                 445

Ala Lys
    450

<210> SEQ ID NO 12
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 12

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
            85                  90                  95

Asn Thr Pro Ile Gly Asp Gly Pro Val Leu Leu Pro Asp Asn His Tyr
        100                 105                 110

Leu Ser Val Gln Ser Lys Leu Ser Lys Asp Pro Asn Glu Lys Arg Asp
    115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 13
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 13

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

```
Met Ala Asp Lys Gln Lys Asn Gly Ile Lys Ala Asn Phe Lys Ile Arg
 65                  70                  75                  80

His Asn Ile Glu Asp Gly Gly Val Gln Leu Ala Tyr His Tyr Gln Gln
                 85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 14
<211> LENGTH: 450
```

```
<212> TYPE: PRT
<213> ORGANISM: Artificial sequence
<220> FEATURE:
<223> OTHER INFORMATION: Synthetic polypeptide

<400> SEQUENCE: 14

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Asp Thr Asp Ser Glu
370                 375                 380
```

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 15
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 15

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

```
Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 16
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 16

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190
```

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Gly Ser Tyr Arg Asp Thr Glu
        370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 17
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 17

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe His Ile Arg
65                  70                  75                  80

His Asn Ile Glu Asp Gly Gly Val Gln Leu Ala Tyr His Tyr Gln Gln
                85                  90                  95

```
Asn Thr Pro Ile Gly Asp Gly Pro Val Leu Pro Asp Asn His Tyr
            100                 105                 110
Leu Ser Val Gln Ser Lys Leu Ser Lys Asp Pro Asn Glu Lys Arg Asp
        115                 120                 125
His Met Val Leu Leu Glu Phe Val Thr Ala Ala Gly Ile Thr Leu Gly
    130                 135                 140
Met Asp Glu Leu Tyr Lys Gly Thr Gly Gly Ser Met Val Ser Lys
145                 150                 155                 160
Gly Glu Glu Leu Phe Thr Gly Val Val Pro Ile Leu Val Glu Leu Asp
                165                 170                 175
Gly Asp Val Asn Gly His Lys Phe Ser Val Ser Gly Glu Gly Glu Gly
            180                 185                 190
Asp Ala Thr Tyr Gly Lys Leu Thr Leu Lys Phe Ile Cys Thr Thr Gly
        195                 200                 205
Lys Leu Pro Val Pro Trp Pro Thr Leu Val Thr Thr Leu Thr Tyr Gly
    210                 215                 220
Val Gln Cys Phe Ser Arg Tyr Pro Asp His Met Lys Gln His Asp Phe
225                 230                 235                 240
Phe Lys Ser Ala Met Pro Glu Gly Tyr Ile Gln Glu Arg Thr Ile Phe
                245                 250                 255
Phe Lys Asp Asp Gly Asn Tyr Lys Thr Arg Ala Glu Val Lys Phe Glu
            260                 265                 270
Gly Asp Thr Leu Val Asn Arg Ile Glu Leu Lys Gly Ile Asp Phe Lys
        275                 280                 285
Glu Asp Gly Asn Ile Leu Gly His Lys Leu Glu Tyr Asn Leu Pro Asp
    290                 295                 300
Gln Leu Thr Glu Glu Gln Ile Ala Glu Phe Lys Glu Ala Phe Ser Leu
305                 310                 315                 320
Phe Asp Lys Asp Gly Asp Gly Thr Ile Thr Thr Lys Glu Leu Gly Thr
                325                 330                 335
Val Met Arg Ser Leu Gly Gln Asn Pro Thr Glu Ala Glu Leu Gln Asp
            340                 345                 350
Met Ile Asn Glu Val Asp Ala Asp Gly Asp Gly Thr Ile Asp Phe Pro
        355                 360                 365
Glu Phe Leu Thr Met Met Ala Arg Lys Met Lys Tyr Arg Asp Thr Glu
    370                 375                 380
Glu Glu Ile Arg Glu Ala Phe Gly Val Phe Asp Lys Asp Gly Asn Gly
385                 390                 395                 400
Tyr Ile Ser Ala Ala Glu Leu Arg His Val Met Thr Asn Leu Gly Glu
                405                 410                 415
Lys Leu Thr Asp Glu Glu Val Asp Glu Met Ile Arg Glu Ala Asp Ile
            420                 425                 430
Asp Gly Asp Gly Gln Val Asn Tyr Glu Glu Phe Val Gln Met Met Thr
        435                 440                 445
Ala Lys
    450

<210> SEQ ID NO 18
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 18
```

-continued

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
        290                 295                 300

Gln Leu Thr Glu Glu Gln Ile Ala Glu Phe Lys Glu Phe Ser Leu
305                 310                 315                 320

Phe Asp Lys Asp Gly Asp Gly Thr Ile Thr Thr Lys Glu Leu Gly Thr
            325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Arg Asp Thr Glu
        370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
```

```
                420          425           430
Asp Gly Asp Gly Gln Val Asn Tyr Glu Glu Phe Val Gln Met Met Thr
        435              440              445

Ala Lys
    450

<210> SEQ ID NO 19
<211> LENGTH: 415
<212> TYPE: PRT
<213> ORGANISM: Artificial sequence
<220> FEATURE:
<223> OTHER INFORMATION: Synthetic polypeptide

<400> SEQUENCE: 19

Met Val Asp Ser Ser Arg Arg Lys Trp Asn Lys Thr Gly His Ala Val
1               5                   10                  15

Arg Ala Ile Gly Arg Leu Ser Ser Pro Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Gly Val Gln Leu Ala Tyr His Tyr Gln Gln Ile Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Ser Gly Gly Met Val Ser Lys Gly Glu Glu
        115                 120                 125

Leu Phe Thr Gly Val Val Pro Ile Gln Val Glu Leu Asp Gly Asp Val
    130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
                165                 170                 175

Val Pro Trp Pro Thr Leu Val Thr Thr Leu Ser Tyr Gly Val Gln Cys
            180                 185                 190

Phe Ser Arg Tyr Pro Asp His Met Lys Gln His Asp Phe Phe Lys Ser
        195                 200                 205

Ala Met Pro Glu Gly Tyr Ile Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
                245                 250                 255

Asn Ile Leu Gly His Lys Leu Glu Tyr Ser Thr Arg Asp Gln Leu Thr
            260                 265                 270

Glu Glu Gln Ile Ala Glu Phe Lys Glu Ala Phe Ser Leu Phe Asp Lys
        275                 280                 285

Asp Gly Asp Gly Thr Ile Thr Thr Lys Glu Leu Gly Thr Val Met Arg
    290                 295                 300

Ser Leu Gly Gln Asn Pro Thr Glu Ala Glu Leu Gln Asp Met Ile Asn
305                 310                 315                 320

Glu Val Asp Ala Asp Gly Asp Gly Thr Ile Asp Phe Pro Glu Phe Leu
```

```
                    325                 330                 335
Thr Met Met Ala Pro Lys Met Gln Asp Thr Asp Ser Glu Glu Glu Ile
                340                 345                 350

Arg Glu Ala Phe Arg Val Phe Asp Lys Asp Gly Asn Gly Tyr Ile Gly
            355                 360                 365

Ala Ala Glu Leu Arg His Val Met Thr Asn Leu Gly Glu Lys Leu Thr
        370                 375                 380

Asp Glu Glu Val Asp Glu Met Ile Arg Val Ala Asp Ile Asp Gly Asp
385                 390                 395                 400

Gly Gln Val Asn Tyr Glu Glu Phe Val Gln Met Met Thr Ala Lys
                405                 410                 415

<210> SEQ ID NO 20
<211> LENGTH: 416
<212> TYPE: PRT
<213> ORGANISM: Artificial sequence
<220> FEATURE:
<223> OTHER INFORMATION: Synthetic polypeptide

<400> SEQUENCE: 20

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Asn Phe Lys Ile Arg His Asn
        35                  40                  45

Ile Glu Asp Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
        115                 120                 125

Glu Leu Phe Thr Gly Val Val Pro Ile Gln Val Glu Leu Asp Gly Asp
    130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Ser Tyr Gly Val Gln
            180                 185                 190

Cys Phe Ser Arg Tyr Pro Asp His Met Lys Gln His Asp Phe Phe Lys
        195                 200                 205

Ser Ala Met Pro Glu Gly Tyr Ile Gln Glu Arg Thr Ile Phe Phe Lys
    210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
            260                 265                 270

Thr Glu Glu Gln Ile Ala Glu Leu Lys Glu Ala Phe Ser Leu Phe Asp
```

275                 280                 285
Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Leu Pro Glu Phe
                325                 330                 335

Gln Thr Met Met Ala Arg Lys Met Asn Asp Thr Asp Ser Glu Glu Glu
                340                 345                 350

Ile Arg Glu Ala Phe Arg Val Phe Asp Lys Asp Gly Asn Gly Tyr Ile
                355                 360                 365

Gly Ala Ala Glu Leu Arg His Val Met Thr Asn Leu Gly Glu Lys Leu
                370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
                405                 410                 415

<210> SEQ ID NO 21
<211> LENGTH: 417
<212> TYPE: PRT
<213> ORGANISM: Artificial sequence
<220> FEATURE:
<223> OTHER INFORMATION: Synthetic polypeptide

<400> SEQUENCE: 21

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
                20                  25                  30

Pro Glu Asp Gly Ala Leu Lys Ser Glu Ile Lys Lys Gly Leu Arg Leu
            35                  40                  45

Lys Asp Gly Gly His Tyr Ala Ala Glu Val Lys Thr Thr Tyr Lys Ala
50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
                100                 105                 110

Gly Gly Thr Gly Gly Ser Leu Val Ser Lys Gly Glu Glu Asp Asn Met
            115                 120                 125

Ala Ile Ile Lys Glu Phe Met Arg Phe Lys Val His Met Glu Gly Ser
130                 135                 140

Val Asn Gly His Glu Phe Glu Ile Glu Gly Glu Gly Glu Gly Arg Pro
145                 150                 155                 160

Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
            180                 185                 190

Lys Ala Tyr Ile Lys His Pro Ala Asp Ile Pro Asp Tyr Phe Lys Leu
        195                 200                 205

Ser Phe Pro Glu Gly Phe Arg Trp Glu Arg Val Met Asn Phe Glu Asp
210                 215                 220

Gly Gly Ile Ile His Val Asn Gln Asp Ser Ser Leu Gln Asp Gly Val

```
               225                 230                 235                 240

Phe Ile Tyr Lys Val Lys Leu Arg Gly Thr Asn Phe Pro Pro Asp Gly
                        245                 250                 255

Pro Val Met Gln Lys Lys Thr Met Gly Trp Glu Ala Thr Arg Asp Gln
                        260                 265                 270

Leu Thr Glu Glu Gln Ile Ala Glu Phe Lys Glu Ala Phe Ser Leu Phe
                        275                 280                 285

Asp Lys Asp Gly Asp Gly Thr Ile Thr Thr Lys Glu Leu Gly Thr Val
                        290                 295                 300

Met Arg Ser Leu Gly Gln Asn Pro Thr Glu Ala Glu Leu Gln Asp Met
        305                 310                 315                 320

Ile Asn Glu Val Asp Ala Asp Gly Asp Gly Thr Phe Asp Phe Pro Glu
                        325                 330                 335

Phe Leu Thr Met Met Ala Arg Lys Met Asn Asp Thr Asp Ser Glu Glu
                        340                 345                 350

Glu Ile Arg Glu Ala Phe Arg Val Phe Asp Lys Asp Gly Asn Gly Tyr
                        355                 360                 365

Ile Gly Ala Ala Glu Leu Arg His Val Met Thr Asp Leu Gly Glu Lys
                        370                 375                 380

Leu Thr Asp Glu Glu Val Asp Glu Met Ile Arg Val Ala Asp Ile Asp
        385                 390                 395                 400

Gly Asp Gly Gln Val Asn Tyr Glu Glu Phe Val Gln Met Met Thr Ala
                        405                 410                 415

Lys

<210> SEQ ID NO 22
<211> LENGTH: 418
<212> TYPE: PRT
<213> ORGANISM: Artificial sequence
<220> FEATURE:
<223> OTHER INFORMATION: Synthetic polypeptide

<400> SEQUENCE: 22

Met Val Asp Ser Pro Arg Arg Lys Trp Asn Lys Thr Gly His Ala Val
        1               5                   10                  15

Arg Ala Ile Gly Arg Leu Ser Ser Pro Glu Asn Val Tyr Ile Lys Ala
                        20                  25                  30

Asp Lys Gln Lys Asn Gly Ile Lys Ala Asn Phe Lys Ile Arg His Asn
                        35                  40                  45

Ile Glu Gly Gly Gly Val Gln Leu Ala Tyr His Tyr Gln Gln Asn Thr
                50                  55                  60

Pro Ile Gly Asp Gly Pro Val Leu Leu Pro Asp Asn His Tyr Leu Ser
        65                  70                  75                  80

Val Gln Ser Ile Leu Ser Lys Asp Pro Asn Glu Lys Arg Asp His Met
                        85                  90                  95

Val Leu Leu Glu Phe Val Thr Ala Ala Gly Ile Thr Leu Gly Met Asp
                        100                 105                 110

Glu Leu Tyr Lys Gly Gly Thr Gly Gly Ser Glu Ser Met Val Ser Lys
                        115                 120                 125

Gly Glu Glu Leu Phe Thr Gly Val Val Pro Ile Gln Val Glu Leu Asp
                        130                 135                 140

Gly Asp Val Asn Gly His Lys Phe Ser Val Ser Gly Glu Gly Glu Gly
        145                 150                 155                 160

Asp Ala Thr Tyr Gly Lys Leu Thr Leu Lys Phe Ile Cys Thr Thr Gly
                        165                 170                 175
```

Lys Leu Pro Val Pro Trp Pro Thr Leu Val Thr Thr Leu Ser His Gly
            180                 185                 190

Val Gln Cys Phe Ser Arg Tyr Pro Asp His Met Lys Gln His Asp Phe
        195                 200                 205

Phe Lys Ser Ala Met Pro Gly Gly Tyr Ile Gln Glu Arg Thr Ile Phe
    210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Thr Arg Gly
            260                 265                 270

Gln Leu Thr Glu Glu Gln Ile Ala Glu Phe Lys Glu Ala Phe Ser Leu
        275                 280                 285

Phe Asp Lys Asp Gly Asp Gly Thr Ile Thr Thr Lys Glu Leu Gly Thr
    290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Pro Lys Met Gln Asp Thr Asp Ser Glu
            340                 345                 350

Glu Glu Ile Arg Glu Ala Phe Arg Val Phe Asp Lys Asp Gly Asn Gly
        355                 360                 365

Tyr Ile Gly Ala Ala Glu Leu Arg His Val Met Thr Asn Leu Gly Glu
    370                 375                 380

Lys Leu Thr Asp Glu Glu Val Asp Glu Met Ile Arg Glu Ala Asp Ile
385                 390                 395                 400

Asp Gly Asp Gly Gln Val Asn Tyr Glu Glu Phe Val Gln Met Met Thr
                405                 410                 415

Ala Lys

<210> SEQ ID NO 23
<211> LENGTH: 416
<212> TYPE: PRT
<213> ORGANISM: Artificial sequence
<220> FEATURE:
<223> OTHER INFORMATION: Synthetic polypeptide

<400> SEQUENCE: 23

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Lys Gln Lys Asn Gly Ile Lys Ala Asn Phe Lys Ile Arg His Asn
        35                  40                  45

Ile Glu Asp Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
            115                 120                 125

Glu Leu Phe Thr Gly Val Val Pro Ile Gln Val Glu Leu Asp Gly Asp
    130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
            165                 170                 175

Pro Val Pro Trp Pro Thr Leu Val Thr Thr Leu Thr Tyr Gly Val Gln
            180                 185                 190

Cys Phe Ser Arg Tyr Pro Asp His Met Lys Gln His Asp Phe Phe Lys
            195                 200                 205

Ser Ala Met Pro Glu Gly Tyr Ile Gln Glu Arg Thr Ile Phe Phe Lys
            210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
            245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
            275                 280                 285

Lys Asp Gly Asp Gly Thr Ile Thr Thr Lys Glu Leu Gly Thr Val Met
            290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Phe Pro Glu Phe
            325                 330                 335

Leu Thr Met Met Ala Arg Lys Met Lys Asp Thr Asp Ser Glu Glu Glu
            340                 345                 350

Ile Arg Glu Ala Phe Arg Val Phe Asp Lys Asp Gly Asn Gly Tyr Ile
            355                 360                 365

Gly Ala Ala Glu Leu Arg His Val Met Thr Asn Leu Gly Glu Lys Leu
            370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
            405                 410                 415

<210> SEQ ID NO 24
<211> LENGTH: 416
<212> TYPE: PRT
<213> ORGANISM: Artificial sequence
<220> FEATURE:
<223> OTHER INFORMATION: Synthetic polypeptide

<400> SEQUENCE: 24

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
            85                  90                  95

Val Leu Leu Glu Phe Val Thr Ala Ala Gly Ile Thr Leu Gly Met Asp
        100                 105                 110

Glu Leu Tyr Lys Gly Gly Thr Gly Gly Ser Met Val Ser Lys Gly Glu
            115                 120                 125

Glu Leu Phe Thr Gly Val Val Pro Ile Gln Val Glu Leu Asp Gly Asp
        130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
            165                 170                 175

Pro Val Pro Trp Pro Thr Leu Val Thr Thr Leu Thr Tyr Gly Val Gln
        180                 185                 190

Cys Phe Ser Arg Tyr Pro Asp His Met Lys Gln His Asp Phe Phe Lys
            195                 200                 205

Ser Ala Met Pro Glu Gly Tyr Ile Gln Glu Arg Thr Ile Phe Phe Lys
210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
            245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
        275                 280                 285

Lys Asp Gly Asp Gly Thr Ile Thr Thr Lys Glu Leu Gly Thr Val Met
        290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Phe Pro Glu Phe
            325                 330                 335

Leu Thr Met Met Ala Arg Lys Met Asn Asp Thr Asp Ser Glu Glu Glu
            340                 345                 350

Ile Arg Glu Ala Phe Arg Val Phe Asp Lys Asp Gly Asn Gly Tyr Ile
        355                 360                 365

Gly Ala Ala Glu Leu Arg His Val Met Thr Asn Leu Gly Glu Lys Leu
        370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
            405                 410                 415

<210> SEQ ID NO 25
<211> LENGTH: 418
<212> TYPE: PRT
<213> ORGANISM: Artificial sequence
<220> FEATURE:
<223> OTHER INFORMATION: Synthetic polypeptide

<400> SEQUENCE: 25

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
                20                  25                  30

Asp Glu Gln Lys Asn Gly Ile Lys Ala Tyr Phe Lys Ile Arg His Asn
            35                  40                  45

Ile Glu Gly Gly Gly Val Gln Leu Ala Tyr His Tyr Gln Gln Asn Thr
 50                  55                  60

Pro Ile Gly Asp Gly Pro Val Leu Leu Pro Asp Asn His Tyr Leu Ser
 65                  70                  75                  80

Val Gln Ser Met Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Glu Ser Met Val Ser Lys
        115                 120                 125

Gly Glu Glu Leu Phe Thr Gly Val Val Pro Ile Gln Val Glu Leu Asp
130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Thr Tyr Gly
            180                 185                 190

Val Gln Cys Phe Ser Arg Tyr Pro Asp His Met Lys Gln His Asp Phe
        195                 200                 205

Phe Lys Ser Ala Met Pro Glu Gly Tyr Ile Gln Glu Arg Thr Ile Phe
210                 215                 220

Phe Lys Gly Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Thr Arg Asp
            260                 265                 270

Gln Leu Thr Glu Glu Gln Ile Ala Glu Phe Lys Glu Ala Phe Ser Leu
        275                 280                 285

Phe Asp Lys Asp Gly Asp Gly Thr Ile Thr Thr Lys Glu Leu Gly Thr
290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Arg Lys Met Lys Asp Thr Asp Ser Glu
            340                 345                 350

Glu Glu Ile Arg Glu Ala Phe Arg Val Phe Asp Lys Asp Gly Asn Gly
        355                 360                 365

Tyr Ile Gly Ala Ala Glu Leu Arg His Val Met Thr Asn Leu Gly Glu
370                 375                 380

Lys Leu Thr Asp Glu Glu Val Asp Glu Met Ile Arg Val Ala Asp Ile
385                 390                 395                 400

Asp Gly Asp Gly Gln Val Asn Tyr Glu Glu Phe Val Gln Met Met Thr
                405                 410                 415

Ala Lys

<210> SEQ ID NO 26

<211> LENGTH: 619
<212> TYPE: PRT
<213> ORGANISM: Artificial sequence
<220> FEATURE:
<223> OTHER INFORMATION: Synthetic polypeptide

<400> SEQUENCE: 26

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala Arg Met Leu Ser Glu Glu Glu Leu Ala Asn Cys Phe
225                 230                 235                 240

Arg Ile Phe Asp Lys Asp Ala Asn Gly Phe Ile Asp Ile Glu Glu Leu
                245                 250                 255

Gly Glu Ile Leu Arg Ala Thr Gly Glu His Val Thr Glu Glu Asp Ile
            260                 265                 270

Glu Asp Leu Met Lys Asp Ser Asp Lys Asn Asn Asp Gly Arg Ile Asp
        275                 280                 285

Phe Asp Glu Phe Leu Lys Met Met Glu Gly Val Gln Gly Thr Ser Glu
290                 295                 300

Glu Glu Leu Ala Asn Cys Phe Arg Ile Phe Asp Lys Asp Ala Asn Gly
305                 310                 315                 320

Phe Ile Asp Ile Glu Glu Leu Gly Glu Ile Leu Arg Ala Thr Gly Glu
                325                 330                 335

His Val Thr Glu Glu Asp Ile Glu Asp Leu Met Lys Asp Ser Asp Lys
            340                 345                 350

Asn Asn Asp Gly Arg Ile Asp Phe Asp Glu Phe Leu Lys Met Met Glu
        355                 360                 365

Gly Val Gln Glu Leu Met Gly Gly Val Gln Leu Ala Asp His Tyr Gln
370                 375                 380
```

```
Gln Asn Thr Pro Ile Gly Asp Gly Pro Val Leu Leu Pro Asp Asn His
385                 390                 395                 400

Tyr Leu Ser Tyr Gln Ser Lys Leu Ser Lys Asp Pro Asn Glu Lys Arg
                405                 410                 415

Asp His Met Val Leu Leu Glu Phe Val Thr Ala Ala Gly Ile Thr Leu
            420                 425                 430

Gly Met Asp Glu Leu Tyr Lys Gly Gly Thr Gly Gly Ser Met Val Ser
            435                 440                 445

Lys Gly Glu Glu Leu Phe Thr Gly Val Val Pro Ile Leu Val Glu Leu
450                 455                 460

Asp Gly Asp Val Asn Gly His Lys Phe Ser Val Arg Gly Glu Gly Glu
465                 470                 475                 480

Gly Asp Ala Thr Asn Gly Lys Leu Thr Leu Lys Phe Ile Cys Thr Thr
                485                 490                 495

Gly Lys Leu Pro Val Pro Trp Pro Thr Leu Val Thr Thr Leu Gly Tyr
            500                 505                 510

Gly Leu Met Cys Phe Ala Arg Tyr Pro Asp His Met Lys Gln His Asp
            515                 520                 525

Phe Phe Lys Ser Ala Met Pro Glu Gly Tyr Val Gln Glu Arg Thr Ile
530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
                565                 570                 575

Lys Glu Asp Gly Asn Ile Leu Gly His Lys Leu Glu Tyr Asn Tyr Asn
            580                 585                 590

Ser His Asn Val Tyr Ile Met Ala Asp Lys Gln Lys Asn Gly Ile Lys
            595                 600                 605

Ala Asn Phe Lys Ile Arg His Asn Ile Glu Asp
    610                 615

<210> SEQ ID NO 27
<211> LENGTH: 673
<212> TYPE: PRT
<213> ORGANISM: Artificial sequence
<220> FEATURE:
<223> OTHER INFORMATION: Synthetic polypeptide

<400> SEQUENCE: 27

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

-continued

```
Ile Asp Phe Lys Glu Asp Gly Asn Ile Leu Gly His Lys Leu Glu Tyr
    130                 135                 140
Asn Tyr Ile Ser His Asn Val Tyr Ile Thr Ala Asp Lys Gln Lys Asn
145                 150                 155                 160
Gly Ile Lys Ala His Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Arg Met His Asp Gln Leu Thr Glu Glu Gln Ile Ala
225                 230                 235                 240
Glu Phe Lys Glu Ala Phe Ser Leu Phe Asp Lys Asp Gly Asp Gly Thr
                245                 250                 255
Ile Thr Thr Lys Glu Leu Gly Thr Val Met Arg Ser Leu Gly Gln Asn
            260                 265                 270
Pro Thr Glu Ala Glu Leu Gln Asp Met Ile Asn Glu Val Asp Ala Asp
        275                 280                 285
Gly Asn Gly Thr Ile Tyr Phe Pro Glu Phe Leu Thr Met Met Ala Arg
    290                 295                 300
Lys Met Lys Asp Thr Asp Ser Glu Glu Glu Ile Arg Glu Ala Phe Arg
305                 310                 315                 320
Val Phe Asp Lys Asp Gly Asn Gly Tyr Ile Ser Ala Ala Gln Leu Arg
                325                 330                 335
His Val Met Thr Asn Leu Gly Glu Lys Leu Thr Asp Glu Glu Val Asp
            340                 345                 350
Glu Met Ile Arg Glu Ala Asp Ile Asp Gly Asp Gly Gln Val Asn Tyr
        355                 360                 365
Glu Glu Phe Val Gln Met Met Thr Ala Lys Gly Gly Lys Arg Arg Trp
    370                 375                 380
Lys Lys Asn Phe Ile Ala Val Ser Ala Ala Asn Arg Phe Lys Lys Ile
385                 390                 395                 400
Ser Ser Ser Gly Ala Leu Glu Leu Met Asp Gly Gly Val Gln Leu Ala
                405                 410                 415
Asp His Tyr Gln Gln Asn Thr Pro Ile Gly Asp Gly Pro Val Leu Leu
            420                 425                 430
Pro Asp Asn His Tyr Leu Ser Tyr Gln Ser Ala Leu Ser Lys Asp Pro
        435                 440                 445
Asn Glu Lys Arg Asp His Met Val Leu Leu Glu Phe Val Thr Ala Ala
    450                 455                 460
Gly Ile Thr Leu Gly Met Asp Glu Leu Tyr Lys Gly Gly Ser Gly Gly
465                 470                 475                 480
Met Val Ser Lys Gly Glu Glu Leu Phe Thr Gly Val Val Pro Ile Leu
                485                 490                 495
Val Glu Leu Asp Gly Asp Val Asn Gly His Lys Phe Ser Val Ser Gly
            500                 505                 510
Glu Gly Glu Gly Asp Ala Thr Tyr Gly Lys Leu Thr Leu Lys Leu Ile
        515                 520                 525
Cys Thr Thr Gly Lys Leu Pro Val Pro Trp Pro Thr Leu Val Thr Thr
    530                 535                 540
```

```
Leu Gly Tyr Gly Leu Gln Cys Phe Ala Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
                580                 585                 590

Val Lys Phe Glu Gly Asp Thr Leu Val Asn Arg Ile Glu Leu Lys Gly
            595                 600                 605

Ile Asp Phe Lys Glu Asp Gly Asn Ile Leu Gly His Lys Leu Glu Tyr
            610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu Leu Ser Arg
                645                 650                 655

Gly Pro Gly Thr Ser Ala Glu Ile Tyr Ala Cys Arg Leu Glu Ile Ser
                660                 665                 670

Asn

<210> SEQ ID NO 28
<211> LENGTH: 653
<212> TYPE: PRT
<213> ORGANISM: Artificial sequence
<220> FEATURE:
<223> OTHER INFORMATION: Synthetic polypeptide

<400> SEQUENCE: 28

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Arg Met His Asp Gln Leu Thr Glu Glu Gln Ile Ala
```

```
                225                 230                 235                 240
Glu Phe Lys Glu Ala Phe Ser Leu Leu Asp Lys Asp Gly Asp Gly Thr
                245                 250                 255

Ile Thr Thr Lys Glu Leu Gly Thr Ala Leu Arg Ser Leu Gly Gln Asn
                260                 265                 270

Pro Thr Glu Ala Glu Leu Gln Asp Met Ile Asn Glu Val Asp Ala Asp
                275                 280                 285

Gly Asn Gly Thr Ile Tyr Phe Pro Glu Phe Leu Thr Met Met Ala Arg
                290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Glu Leu Arg
                325                 330                 335

His Val Met Thr Asn Leu Gly Glu Lys Leu Thr Asp Glu Glu Val Asp
                340                 345                 350

Glu Met Ile Arg Glu Ala Asp Ile Asp Gly Asp Gly Gln Val Asn Tyr
                355                 360                 365

Glu Glu Phe Val Gln Met Met Thr Ala Lys Gly Gly Lys Arg Arg Trp
                370                 375                 380

Gln Lys Thr Gly His Ala Val Arg Ala Phe Gly Arg Leu Lys Lys Ile
385                 390                 395                 400

Ser Ser Ser Gly Ala Leu Glu Leu Met Asp Gly Gly Val Gln Leu Ala
                405                 410                 415

Asp His Tyr Gln Gln Asn Thr Pro Ile Gly Asp Gly Pro Val Leu Leu
                420                 425                 430

Pro Asp Asn His Tyr Leu Ser Tyr Gln Ser Ala Leu Ser Lys Asp Pro
                435                 440                 445

Asn Glu Lys Arg Asp His Met Val Leu Leu Glu Phe Val Thr Ala Ala
                450                 455                 460

Gly Ile Thr Leu Gly Met Asp Glu Leu Tyr Lys Gly Gly Ser Gly Gly
465                 470                 475                 480

Met Val Ser Lys Gly Glu Glu Leu Phe Thr Gly Val Val Pro Ile Leu
                485                 490                 495

Val Glu Leu Asp Gly Asp Val Asn Gly His Lys Phe Ser Val Ser Gly
                500                 505                 510

Glu Gly Glu Gly Asp Ala Thr Tyr Gly Lys Leu Thr Leu Lys Leu Ile
                515                 520                 525

Cys Thr Thr Gly Lys Leu Pro Val Pro Trp Pro Thr Leu Val Thr Thr
530                 535                 540

Leu Gly Tyr Gly Leu Gln Cys Phe Ala Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
                580                 585                 590

Val Lys Phe Glu Gly Asp Thr Leu Val Asn Arg Ile Glu Leu Lys Gly
                595                 600                 605

Ile Asp Phe Lys Glu Asp Gly Asn Ile Leu Gly His Lys Leu Glu Tyr
                610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu
                645                 650
```

<210> SEQ ID NO 29
<211> LENGTH: 344
<212> TYPE: PRT
<213> ORGANISM: Chlamydomonas reinhardtii

<400> SEQUENCE: 29

| Met | Ser | Arg | Arg | Pro | Trp | Leu | Leu | Ala | Leu | Ala | Leu | Ala | Val | Ala | Leu |
|---|---|---|---|---|---|---|---|---|---|---|---|---|---|---|---|
| 1 | | | | 5 | | | | | 10 | | | | | 15 | |

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp
            340

<210> SEQ ID NO 30
<211> LENGTH: 310
<212> TYPE: PRT

<213> ORGANISM: Chlamydomonas reinhardtii

<400> SEQUENCE: 30

| | | | | | | | | | | | | | | | |
|---|---|---|---|---|---|---|---|---|---|---|---|---|---|---|---|
| Met | Asp | Tyr | Gly | Gly | Ala | Leu | Ser | Ala | Val | Gly | Arg | Glu | Leu | Leu | Phe |
| 1 | | | | 5 | | | | | 10 | | | | | 15 | |
| Val | Thr | Asn | Pro | Val | Val | Asn | Gly | Ser | Val | Leu | Val | Pro | Glu | Asp | |
| | | | 20 | | | | | 25 | | | | | 30 | | |
| Gln | Cys | Tyr | Cys | Ala | Gly | Trp | Ile | Glu | Ser | Arg | Gly | Thr | Asn | Gly | Ala |
| | | | 35 | | | | | 40 | | | | | 45 | | |
| Gln | Thr | Ala | Ser | Asn | Val | Leu | Gln | Trp | Leu | Ala | Ala | Gly | Phe | Ser | Ile |
| | 50 | | | | | 55 | | | | | 60 | | | | |
| Leu | Leu | Leu | Met | Phe | Tyr | Ala | Tyr | Gln | Thr | Trp | Lys | Ser | Thr | Cys | Gly |
| 65 | | | | | 70 | | | | | 75 | | | | | 80 |
| Trp | Glu | Glu | Ile | Tyr | Val | Cys | Ala | Ile | Glu | Met | Val | Lys | Val | Ile | Leu |
| | | | | 85 | | | | | 90 | | | | | 95 | |
| Glu | Phe | Phe | Phe | Glu | Phe | Lys | Asn | Pro | Ser | Met | Leu | Tyr | Leu | Ala | Thr |
| | | | 100 | | | | | 105 | | | | | 110 | | |
| Gly | His | Arg | Val | Gln | Trp | Leu | Arg | Tyr | Ala | Glu | Trp | Leu | Leu | Thr | Cys |
| | | 115 | | | | | 120 | | | | | 125 | | | |
| Pro | Val | Ile | Leu | Ile | His | Leu | Ser | Asn | Leu | Thr | Gly | Leu | Ser | Asn | Asp |
| | 130 | | | | | 135 | | | | | 140 | | | | |
| Tyr | Ser | Arg | Arg | Thr | Met | Gly | Leu | Leu | Val | Ser | Asp | Ile | Gly | Thr | Ile |
| 145 | | | | | 150 | | | | | 155 | | | | | 160 |
| Val | Trp | Gly | Ala | Thr | Ser | Ala | Met | Ala | Thr | Gly | Tyr | Val | Lys | Val | Ile |
| | | | | 165 | | | | | 170 | | | | | 175 | |
| Phe | Phe | Cys | Leu | Gly | Leu | Cys | Tyr | Gly | Ala | Asn | Thr | Phe | Phe | His | Ala |
| | | | 180 | | | | | 185 | | | | | 190 | | |
| Ala | Lys | Ala | Tyr | Ile | Glu | Gly | Tyr | His | Thr | Val | Pro | Lys | Gly | Arg | Cys |
| | | 195 | | | | | 200 | | | | | 205 | | | |
| Arg | Gln | Val | Val | Thr | Gly | Met | Ala | Trp | Leu | Phe | Phe | Val | Ser | Trp | Gly |
| | 210 | | | | | 215 | | | | | 220 | | | | |
| Met | Phe | Pro | Ile | Leu | Phe | Ile | Leu | Gly | Pro | Glu | Gly | Phe | Gly | Val | Leu |
| 225 | | | | | 230 | | | | | 235 | | | | | 240 |
| Ser | Val | Tyr | Gly | Ser | Thr | Val | Gly | His | Thr | Ile | Ile | Asp | Leu | Met | Ser |
| | | | | 245 | | | | | 250 | | | | | 255 | |
| Lys | Asn | Cys | Trp | Gly | Leu | Leu | Gly | His | Tyr | Leu | Arg | Val | Leu | Ile | His |
| | | | 260 | | | | | 265 | | | | | 270 | | |
| Glu | His | Ile | Leu | Ile | His | Gly | Asp | Ile | Arg | Lys | Thr | Thr | Lys | Leu | Asn |
| | | 275 | | | | | 280 | | | | | 285 | | | |
| Ile | Gly | Gly | Thr | Glu | Ile | Glu | Val | Glu | Thr | Leu | Val | Glu | Asp | Glu | Ala |
| | 290 | | | | | 295 | | | | | 300 | | | | |
| Glu | Ala | Gly | Ala | Val | Pro | | | | | | | | | | |
| 305 | | | | | 310 | | | | | | | | | | |

<210> SEQ ID NO 31
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 31

| | | | | | | | | | | | | | | | |
|---|---|---|---|---|---|---|---|---|---|---|---|---|---|---|---|
| Met | Asp | Tyr | Gly | Gly | Ala | Leu | Ser | Ala | Val | Gly | Arg | Glu | Leu | Leu | Phe |
| 1 | | | | 5 | | | | | 10 | | | | | 15 | |
| Val | Thr | Asn | Pro | Val | Val | Asn | Gly | Ser | Val | Leu | Val | Pro | Glu | Asp | |
| | | | 20 | | | | | 25 | | | | | 30 | | |

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                    85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 32
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 32

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

-continued

```
Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 33
<211> LENGTH: 300
<212> TYPE: PRT
<213> ORGANISM: Volvox carteri

<400> SEQUENCE: 33

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
```

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 34
<211> LENGTH: 300
<212> TYPE: PRT
<213> ORGANISM: Artificial sequence
<220> FEATURE:
<223> OTHER INFORMATION: Synthetic polypeptide

<400> SEQUENCE: 34

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
        50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Ser Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg

```
            195                 200                 205
Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Glu Asp
    290                 295                 300

<210> SEQ ID NO 35
<211> LENGTH: 300
<212> TYPE: PRT
<213> ORGANISM: Artificial sequence
<220> FEATURE:
<223> OTHER INFORMATION: Synthetic polypeptide

<400> SEQUENCE: 35

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Ala Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
```

```
                    260                 265                 270
Tyr Gly Asp Ile Arg Lys Lys Gln Lys Ile Thr Ile Ala Gly Gln Glu
            275                 280                 285

Met Glu Val Glu Thr Leu Val Ala Glu Glu Asp
    290                 295                 300

<210> SEQ ID NO 36
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 36

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
```

Thr Leu Val Ala Glu Glu Asp
        340

<210> SEQ ID NO 37
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 37

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Val Tyr Gly Ser Thr Val Gly His
        275                 280                 285

Thr Ile Ile Asp Leu Met Ser Lys Asn Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340

<210> SEQ ID NO 38
<211> LENGTH: 316
<212> TYPE: PRT
<213> ORGANISM: Artificial sequence
<220> FEATURE:
<223> OTHER INFORMATION: Synthetic polypeptide

<400> SEQUENCE: 38

```
Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Glu Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
    130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
    290                 295                 300

Asp Val Leu Ala Phe Val Thr Glu Glu Asp Lys Val
305                 310                 315
```

<210> SEQ ID NO 39
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 39

```
Met Glu Pro Val Leu Gly Leu Ala Ser Thr Ala Val Arg Glu Leu Thr
1               5                   10                  15

Ala Gly Gly Ser Gly Asn Pro Tyr Glu Ser Tyr Lys Pro Pro Glu Asp
            20                  25                  30

Pro Cys Ala Leu Thr Pro Phe Gly Cys Leu Thr Asn Phe Trp Cys Asp
        35                  40                  45

Pro Gln Phe Gly Leu Ala Asp Ala Lys Tyr Asp Tyr Cys Tyr Val Lys
    50                  55                  60

Ala Ala Tyr Gly Glu Leu Ala Ile Val Glu Thr Ser Arg Leu Pro Trp
65                  70                  75                  80

Leu Tyr Ser His Gly Ser Asp Ala Glu His Gln Gly Ala Leu Ala Met
                85                  90                  95

Gln Trp Met Ala Phe Ala Leu Cys Ile Ile Cys Leu Val Phe Tyr Ala
            100                 105                 110

Tyr His Ser Trp Lys Ala Thr Thr Gly Trp Glu Glu Val Tyr Val Cys
        115                 120                 125

Val Val Glu Leu Val Lys Val Leu Leu Glu Ile Tyr Lys Glu Phe Glu
    130                 135                 140

Ser Pro Ala Ser Ile Tyr Leu Pro Thr Ala Asn Ala Ala Leu Trp Leu
145                 150                 155                 160

Arg Tyr Gly Glu Trp Leu Leu Thr Cys Pro Val Ile Leu Ile His Leu
                165                 170                 175

Ser Asn Ile Thr Gly Leu Lys Asp Asp Tyr Asn Lys Arg Thr Met Gln
            180                 185                 190

Leu Leu Val Ser Asp Ile Gly Cys Val Val Trp Gly Ile Thr Ala Ala
        195                 200                 205

Phe Ser Val Gly Trp Leu Lys Trp Val Phe Phe Val Leu Gly Leu Leu
    210                 215                 220

Tyr Gly Ser Asn Thr Tyr Phe His Ala Ala Lys Val Tyr Ile Glu Ser
225                 230                 235                 240

Tyr His Thr Val Pro Lys Gly His Cys Arg Leu Ile Val Arg Leu Met
                245                 250                 255

Ala Tyr Cys Phe Tyr Val Ala Trp Thr Met Tyr Pro Ile Leu Phe Ile
            260                 265                 270

Leu Gly Pro Glu Gly Leu Gly His Met Ser Ala Tyr Met Ser Thr Ala
        275                 280                 285

Leu His Gly Val Ala Asp Met Leu Ser Lys Gln Ile Trp Gly Leu Leu
    290                 295                 300

Gly His His Leu Arg Val Lys Ile Phe Glu His Ile Leu Ile His Gly
305                 310                 315                 320

Asp Ile Arg Lys Thr Thr Met Gln Val Gly Gln Met Val Gln
                325                 330                 335

Val Glu Glu Met Val Asp Glu Glu Asp Thr Ile
            340                 345
```

<210> SEQ ID NO 40
<211> LENGTH: 345
<212> TYPE: PRT
<213> ORGANISM: Artificial sequence
<220> FEATURE:
<223> OTHER INFORMATION: Synthetic polypeptide

<400> SEQUENCE: 40

Met Ser Arg Leu Val Ala Ala Ser Trp Leu Ala Leu Leu Leu Cys
1               5                   10                  15

Gly Ile Thr Ser Thr Thr Ala Ser Ser Ala Pro Ala Ser Ser
            20                  25                  30

Thr Asp Gly Thr Ala Ala Ala Val Ser His Tyr Ala Met Asn Gly
            35                  40                  45

Phe Asp Glu Leu Ala Lys Gly Ala Val Pro Glu Asp His Phe Val
        50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
        130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
                260                 265                 270

Gly Leu Leu Lys Leu Ser Pro Tyr Ala Asn Ser Ile Gly His Ser Ile
                275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
                325                 330                 335

Val Glu Glu Glu Asp Glu Asp Thr Val
                340                 345

<210> SEQ ID NO 41
<211> LENGTH: 325
<212> TYPE: PRT
<213> ORGANISM: Artificial sequence
<220> FEATURE:
<223> OTHER INFORMATION: Synthetic polypeptide

<400> SEQUENCE: 41

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325

<210> SEQ ID NO 42
<211> LENGTH: 258
<212> TYPE: PRT
<213> ORGANISM: Halorubrum sodomense

<400> SEQUENCE: 42

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

```
Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
             85                      90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 43
<211> LENGTH: 248
<212> TYPE: PRT
<213> ORGANISM: Halorubrum sp. TP009

<400> SEQUENCE: 43

Met Asp Pro Ile Ala Leu Gln Ala Gly Tyr Asp Leu Leu Gly Asp Gly
 1               5                  10                  15

Arg Pro Glu Thr Leu Trp Leu Gly Ile Gly Thr Leu Leu Met Leu Ile
             20                  25                  30

Gly Thr Phe Tyr Phe Ile Val Lys Gly Trp Gly Val Thr Asp Lys Glu
         35                  40                  45

Ala Arg Glu Tyr Tyr Ser Ile Thr Ile Leu Val Pro Gly Ile Ala Ser
     50                  55                  60

Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
             85                      90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175
```

-continued

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 44
<211> LENGTH: 223
<212> TYPE: PRT
<213> ORGANISM: Guillardia theta

<400> SEQUENCE: 44

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
    50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
        115                 120                 125

Phe Phe Gly Met Cys Trp Phe Leu His Ile Ile Phe Ala Leu Gly Lys
    130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
        195                 200                 205

Gly Leu Ile Leu Met Ser Gly Ala Ala Thr Gly Tyr Glu Ser Ile
    210                 215                 220

<210> SEQ ID NO 45
<211> LENGTH: 262
<212> TYPE: PRT
<213> ORGANISM: Oxyrrhis marina

<400> SEQUENCE: 45

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

```
Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
        195                 200                 205

Tyr Ile Val Lys Asn Ile Gly Leu Ala Gly Ser Thr Ala Thr Met Tyr
    210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
            260

<210> SEQ ID NO 46
<211> LENGTH: 313
<212> TYPE: PRT
<213> ORGANISM: Leptosphaeria maculans

<400> SEQUENCE: 46

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
```

```
            130                 135                 140
Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
                180                 185                 190

Tyr Thr Ile Ala Cys Ile Ala Tyr Ile Phe Val Val Trp His Leu Val
                195                 200                 205

Leu Asn Gly Gly Ala Asn Ala Arg Val Lys Gly Glu Lys Leu Arg Ser
            210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
                260                 265                 270

Phe Gly Ala Trp Leu Leu Val Thr His Ala Asn Leu Arg Glu Ser Asp
                275                 280                 285

Val Glu Leu Asn Gly Phe Trp Ala Asn Gly Leu Asn Arg Glu Gly Ala
            290                 295                 300

Ile Arg Ile Gly Glu Asp Asp Gly Ala
305                 310

<210> SEQ ID NO 47
<211> LENGTH: 273
<212> TYPE: PRT
<213> ORGANISM: Natronomonas Pharaonis

<400> SEQUENCE: 47

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
                20                  25                  30

Leu Phe Val Phe Met Thr Arg Gly Leu Asp Asp Pro Arg Ala Lys Leu
                35                  40                  45

Ile Ala Val Ser Thr Ile Leu Val Pro Val Val Ser Ile Ala Ser Tyr
            50                  55                  60

Thr Gly Leu Ala Ser Gly Leu Thr Ile Ser Val Leu Glu Met Pro Ala
65              70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
                100                 105                 110

Thr Pro Met Ile Leu Leu Ala Leu Gly Leu Leu Ala Gly Ser Asn Ala
                115                 120                 125

Thr Lys Leu Phe Thr Ala Ile Thr Phe Asp Ile Ala Met Cys Val Thr
            130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
                180                 185                 190
```

```
Phe Asn Thr Leu Lys Leu Leu Thr Val Val Met Trp Leu Gly Tyr Pro
            195                 200                 205

Ile Val Trp Ala Leu Gly Val Glu Gly Ile Ala Val Leu Pro Val Gly
210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
            245                 250                 255

Ser Gly Ser Ile Leu Asp Val Pro Ser Ala Ser Gly Thr Pro Ala Asp
            260                 265                 270

Asp

<210> SEQ ID NO 48
<211> LENGTH: 365
<212> TYPE: PRT
<213> ORGANISM: Dunaliella salina

<400> SEQUENCE: 48

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
    130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220

Pro Pro Asn His Val Lys Val Ile Leu Phe Thr Ile Gly Leu Leu Tyr
225                 230                 235                 240

Gly Leu Phe Thr Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285
```

```
Gly Arg Glu Gly Phe Gly His Ile Thr Tyr Phe Gly Ser Ser Ile Gly
        290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
                340                 345                 350

Glu Glu Tyr Val Asp Ser Asn Asp Lys Asp Ser Asp Val
                355                 360                 365

<210> SEQ ID NO 49
<211> LENGTH: 1083
<212> TYPE: PRT
<213> ORGANISM: Artificial sequence
<220> FEATURE:
<223> OTHER INFORMATION: Synthetic polypeptide

<400> SEQUENCE: 49

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Lys Ser Arg Ile Thr Ser Glu Gly Glu Tyr Ile Pro Leu Asp
            260                 265                 270

Gln Ile Asp Ile Asn Val Gly Ala Pro Gly Ser Gly Ala Thr Asn Phe
        275                 280                 285
```

```
Ser Leu Leu Lys Gln Ala Gly Asp Val Glu Glu Asn Pro Gly Pro Met
290                 295                 300

Asp Leu Lys Glu Ser Pro Ser Glu Gly Ser Leu Gln Pro Ser Ser Ile
305                 310                 315                 320

Gln Ile Phe Ala Asn Thr Ser Thr Leu His Gly Ile Arg His Ile Phe
            325                 330                 335

Val Tyr Gly Pro Leu Thr Ile Arg Arg Val Leu Trp Ala Val Ala Phe
        340                 345                 350

Val Gly Ser Leu Gly Leu Leu Val Glu Ser Ser Glu Arg Val Ser
            355                 360                 365

Tyr Tyr Phe Ser Tyr Gln His Val Thr Lys Val Asp Glu Val Val Ala
370                 375                 380

Gln Ser Leu Val Phe Pro Ala Val Thr Leu Cys Asn Leu Asn Gly Phe
385                 390                 395                 400

Arg Phe Ser Arg Leu Thr Thr Asn Asp Leu Tyr His Ala Gly Glu Leu
                405                 410                 415

Leu Ala Leu Leu Asp Val Asn Leu Gln Ile Pro Asp Pro His Leu Ala
            420                 425                 430

Asp Pro Thr Val Leu Glu Ala Leu Arg Gln Lys Ala Asn Phe Lys His
        435                 440                 445

Tyr Lys Pro Lys Gln Phe Ser Met Leu Glu Phe Leu His Arg Val Gly
    450                 455                 460

His Asp Leu Lys Asp Met Met Leu Tyr Cys Lys Phe Lys Gly Gln Glu
465                 470                 475                 480

Cys Gly His Gln Asp Phe Thr Thr Val Phe Thr Lys Tyr Gly Lys Cys
                485                 490                 495

Tyr Met Phe Asn Ser Gly Glu Asp Gly Lys Pro Leu Leu Thr Thr Val
            500                 505                 510

Lys Gly Gly Thr Gly Asn Gly Leu Glu Ile Met Leu Asp Ile Gln Gln
        515                 520                 525

Asp Glu Tyr Leu Pro Ile Trp Gly Glu Thr Glu Thr Thr Phe Glu
    530                 535                 540

Ala Gly Val Lys Val Gln Ile His Ser Gln Ser Glu Pro Pro Phe Ile
545                 550                 555                 560

Gln Glu Leu Gly Phe Gly Val Ala Pro Gly Phe Gln Thr Phe Val Ala
                565                 570                 575

Thr Gln Glu Gln Arg Leu Thr Tyr Leu Pro Pro Trp Gly Glu Cys
            580                 585                 590

Arg Ser Ser Glu Met Gly Leu Asp Phe Phe Pro Val Tyr Ser Ile Thr
        595                 600                 605

Ala Cys Arg Ile Asp Cys Glu Thr Arg Tyr Ile Val Glu Asn Cys Asn
610                 615                 620

Cys Arg Met Val His Met Pro Gly Asp Ala Pro Phe Cys Thr Pro Glu
625                 630                 635                 640

Gln His Lys Glu Cys Ala Glu Pro Ala Leu Gly Leu Leu Ala Glu Lys
                645                 650                 655

Asp Ser Asn Tyr Cys Leu Cys Arg Thr Pro Cys Asn Leu Thr Arg Tyr
            660                 665                 670

Asn Lys Glu Leu Ser Met Val Lys Ile Pro Ser Lys Thr Ser Ala Lys
        675                 680                 685

Tyr Leu Glu Lys Lys Phe Asn Lys Ser Glu Lys Tyr Ile Ser Glu Asn
    690                 695                 700

Ile Leu Val Leu Asp Ile Phe Phe Glu Ala Leu Asn Tyr Glu Thr Ile
```

```
                705                 710                 715                 720
            Glu Gln Lys Lys Ala Tyr Glu Val Ala Ala Leu Leu Gly Asp Ile Gly
                            725                 730                 735

Gly Gln Met Gly Leu Phe Ile Gly Ala Ser Leu Leu Thr Ile Leu Glu
                            740                 745                 750

Leu Phe Asp Tyr Ile Tyr Glu Leu Ile Lys Glu Lys Leu Leu Asp Leu
                            755                 760                 765

Leu Gly Lys Glu Glu Glu Gly Ser His Asp Glu Asn Met Ser Thr
                            770                 775                 780

Cys Asp Thr Met Pro Asn His Ser Glu Thr Ile Ser His Thr Val Asn
            785                 790                 795                 800

Val Pro Leu Gln Thr Ala Leu Gly Thr Leu Glu Glu Ile Ala Cys Ala
                            805                 810                 815

Ala Ala Lys Ser Arg Ile Thr Ser Glu Gly Glu Tyr Ile Pro Leu Asp
                            820                 825                 830

Gln Ile Asp Ile Asn Val Val Ser Lys Gly Glu Glu Leu Phe Thr Gly
                            835                 840                 845

Val Val Pro Ile Leu Val Glu Leu Asp Gly Asp Val Asn Gly His Lys
                            850                 855                 860

Phe Ser Val Ser Gly Glu Gly Glu Gly Asp Ala Thr Tyr Gly Lys Leu
            865                 870                 875                 880

Thr Leu Lys Phe Ile Cys Thr Thr Gly Lys Leu Pro Val Pro Trp Pro
                            885                 890                 895

Thr Leu Val Thr Thr Phe Gly Tyr Gly Leu Gln Cys Phe Ala Arg Tyr
                            900                 905                 910

Pro Asp His Met Lys Gln His Asp Phe Phe Lys Ser Ala Met Pro Glu
                            915                 920                 925

Gly Tyr Val Gln Glu Arg Thr Ile Phe Phe Lys Asp Asp Gly Asn Tyr
                            930                 935                 940

Lys Thr Arg Ala Glu Val Lys Phe Glu Gly Asp Thr Leu Val Asn Arg
            945                 950                 955                 960

Ile Glu Leu Lys Gly Ile Asp Phe Arg Glu Asp Gly Asn Ile Leu Gly
                            965                 970                 975

His Lys Leu Glu Tyr Asn Tyr Asn Ser His Asn Val Tyr Ile Met Ala
                            980                 985                 990

Asp Lys Gln Lys Asn Gly Ile Lys Val Asn Phe Lys Ile Arg His Asn
                            995                 1000                1005

Ile Glu Asp Gly Ser Val Gln Leu Ala Asp His Tyr Gln Gln Asn
                            1010                1015                1020

Thr Pro Ile Gly Asp Gly Pro Val Leu Leu Pro Asp Asn His Tyr
                            1025                1030                1035

Leu Ser Tyr Gln Ser Ala Leu Ser Lys Asp Pro Asn Glu Lys Arg
                            1040                1045                1050

Asp His Met Val Leu Leu Glu Phe Val Thr Ala Ala Gly Ile Thr
                            1055                1060                1065

Leu Gly Met Asp Glu Leu Tyr Lys Phe Cys Tyr Glu Asn Glu Val
                            1070                1075                1080
```

METHOD AND SYSTEMS FOR MEASURING NEURAL ACTIVITY

CROSS-REFERENCE

This application is a continuation of U.S. application Ser. No. 15/749,052, which is a U.S. National Phase application under 35 U.S.C. § 371 of PCT Application No. PCT/US2016/062314, filed Nov. 16, 2016, which claims the benefit of U.S. Provisional Patent Application No. 62/257,140, filed Nov. 18, 2015, which applications are incorporated herein by reference in their entirety.

INTRODUCTION

Genetically-encoded $Ca^{2+}$ indicators (GECIs) are polypeptides whose fluorescence is modulated by intracellular concentration of calcium ions. GECIs are used to optically measure neuronal activity at single resolution and to study in vivo dynamics and population coding under a microscope system.

Optogenetic refers to methods of manipulating the activity of excitable cells, such as neurons, by altering the membrane potential of excitable cells expressing light-activated proteins that depolarize or hyperpolarize cells in response to light.

Optical fibers, which bi-directionally transmit light between separate sites, can be used for optical imaging and/or manipulating neural activity relevant to behavioral circuitry mechanisms.

SUMMARY

Provided herein is a method including a) illuminating one or more regions of a target tissue with a light stimulus comprising light pulses of a plurality of wavelengths, wherein each of the one or more regions comprises one or more collections of a plurality of neurons, or a subcellular portion thereof, labeled with one or more neural activity-dependent fluorescent moieties; the light pulses comprise: i) a first set of light pulses at a first wavelength; and ii) a second set light pulses at one or more wavelengths, wherein each of the one or more wavelengths are different from the first wavelength and are at an excitation wavelength of the one or more neural activity-dependent fluorescent moieties, and wherein each light pulse of the first set are interleaved among light pulses of the second set, thereby generating fluorescence from each of the one or more regions, wherein a multimode optical fiber is configured to direct the light stimulus to, and collect the fluorescence from, each of the one or more regions; b) recording, onto independent frames of an image detector for each light pulse, an image of a cross-section of the multimode optical fiber for each of the one or more regions, wherein a cross-sectional average of the fluorescence generated in response to the second set of light pulses is representative of an aggregate neural activity of the one or more regions; and c) analyzing the recorded image, to generate an output comprising a measure of the aggregate neural activity in each of the one or more regions. In some embodiments, the multimode optical fiber has a diameter in the range of 100 to 1000 µm. In some embodiments, the one or more collections include one or more functionally-defined collections of a plurality of neurons.

In any embodiment, the one or more regions may include: a first collection of a plurality of neurons, each neuron of the first collection containing a first neural activity-dependent fluorescent moiety; and a second collection of a plurality of neurons, each neuron of the second collection containing a second neural activity-dependent fluorescent moiety, and wherein the second set of light pulses include: a third set of light pulses at a second wavelength, different from the first wavelength, wherein the second wavelength is at an excitation wavelength of the first neural activity-dependent fluorescent moiety; and a fourth set of light pulses at a third wavelength, different from the first and second wavelengths, wherein the third wavelength is at an excitation wavelength of the second neural activity-dependent fluorescent moiety, and wherein the recording includes recording a first image and a second image of the terminal cross-section of the multimode optical fiber from each of the one or more regions, wherein a cross-sectional average of the fluorescence generated in response to the third set of light pulses in the first image is representative of an aggregate neural activity of the first collection of a plurality of neurons, and a cross-sectional average of the fluorescence generated in response to the fourth set of light pulses in the second image is representative of an aggregate neural activity of the second collection of a plurality of neurons. In some cases, the first collection and the second collection are distinct collections of a plurality of neurons. In some cases, the first collection and the second collection are non-overlapping collections of a plurality of neurons. In some embodiments, the light pulses of the third set and light pulses of the fourth set are synchronous.

In any embodiment, the light stimulus may include an alternating order of a light pulse from the first set of light pulses and one or more light pulses from the second set of light pulses.

In any embodiment, the analyzing may include: 1) demarcating the cross-section of the multimode optical fiber from each of the one or more regions in the recorded image; and 2) calculating an average of the fluorescence across each of the cross-sections.

In any embodiment, the analyzing may include 3) calculating a normalized change in the fluorescence over a baseline fluorescence for each cross-section of the multimode optical fibers in the recorded image. In some cases, the baseline fluorescence is a median of the average fluorescence within each cross-section of the multimode optical fibers across a plurality of recorded images.

In any embodiment, a neural activity-independent fluorescence may be generated in response to the first set of light pulses. In some embodiments, the first wavelength is at an isosbestic point of at least one of the one or more neural activity-dependent fluorescent moieties. In some cases, the analyzing includes 4) subtracting an average of the neural activity-independent fluorescence across a cross-section from an average of the neural activity-dependent fluorescence across the cross-section, to obtain a motion-corrected measure of the aggregate neural activity.

In any embodiment, at least one of the one or more regions includes a third collection of a plurality of neurons, or a subcellular portion thereof, each neuron of the third collection containing a light-activated polypeptide configured to modulate the electrical activity of the neuron in response to the light stimulus, wherein the first wavelength is at an activation wavelength of the light-activated polypeptide. In some embodiments, the third collection comprises a functionally-defined collection of a plurality of neurons. In some cases, the third collection includes the same neurons as at least one of the one or more collections of a plurality of neurons. In some embodiments, the light pulses of the second set have a power of 50 µW or less. In some embodiments, light pulses in the first set are pulsed at a first frequency less than a second frequency at which light pulses of the second set are pulsed. In some embodiments, the light pulses of the first set have a power sufficient to approximate neural activity-dependent fluorescence generated by a natural stimulus. In some embodiments, the light-activated polypeptide is a depolarizing or hyperpolarizing light-activated polypeptide. In some embodiments, the light-activated polypeptide is an ion channel or an ion pump. In some cases, the light-activated polypeptide is selected from: ChR2, iC1C2, C1C2, GtACR2, NpHR, eNpHR3.0, C1V1, VChR1, VChR2, SwiChR, Arch, ArchT, KR2, ReaChR, ChIEF, Chronos, ChRGR, CsChrimson, bReaCh-ES, and variants thereof.

In any embodiment, the target tissue may be an in vivo tissue. In some embodiments, the target tissue is in a freely moving animal.

In any embodiment, the method may include illuminating two or more regions of the target tissue. In some cases, the two or more regions include functionally distinct regions of the target tissue. In some embodiments, the two or more regions comprise anatomically distinct regions of the target tissue. In some embodiments, the two or more regions comprise functionally connected regions of the target tissue.

In any embodiment, the one or more regions may include one or more mammalian brain regions. In some cases, the one or more mammalian brain regions is selected from at least a portion of the ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyrus, entorhinal cortex, olfactory cortex, sensory cortex, thalamus, primary motor cortex, and cerebellum.

In any embodiment, one or more regions may include neuronal projections of the one or more collections of a plurality of neurons. In some cases, the neuronal projections are axonal projections.

In any embodiment, the one or more neural activity-dependent fluorescent moieties may include a genetically-encoded indicator dye.

In any embodiment, the one or more collections may include a plurality of dopaminergic, cholinergic, GABAergic, glutamatergic, or peptidergic neurons.

In any embodiment, the one or more neural activity-dependent fluorescent moieties may include a calcium- and/or a voltage-sensitive indicator dye.

In any embodiment, the one or more collections may include genetically modified neurons expressing the one or more activity-dependent fluorescent moieties. In some cases, expression of each of the one or more neural activity-dependent fluorescent moieties is regulated under a cell-specific promoter. In some cases, expression of each of the one or more neural activity-dependent fluorescent moieties is regulated in a Cre-dependent manner. In some embodiments, the method further includes, before the illuminating, genetically modifying neurons of the one or more regions of the target tissue to express the one or more neural activity-dependent fluorescent moieties.

In any embodiment, the image detector may be a charge-coupled device (CCD) or a complementary metal oxide semiconductor (CMOS) camera.

In any embodiment, the recording may include recording the image synchronously with the second set of light pulses.

In any embodiment, the recording comprises recording the image synchronously with the first set and second set of light pulses.

Also provided herein is a system that includes a) an illumination unit; b) an objective, wherein the objective is configured to receive light from the illumination unit and to focus the light at a working distance from the objective; c) a plurality of light conduits, each light conduit containing one or more multimode optical fibers and defining a first end, a second end opposite the first, and a light conduit numerical aperture, wherein a terminus at the first end of each of the light conduits is at the working distance from the objective; a terminal cross-section of a multimode optical fiber at the first end of each of the light conduits is in a field of view of the objective; and the light conduit numerical aperture is less than a numerical aperture of the objective; and d) an image detector; wherein the system is configured to: generate a light stimulus including light pulses of a plurality of wavelengths; illuminate a region in a target tissue at the second end of each of the plurality of light conduits, the region containing one or more collections of a plurality of neurons, or a subcellular portion thereof, labeled with one or more neural activity-dependent fluorescent moieties, wherein the plurality of wavelengths comprises one or more wavelengths at an excitation wavelength of the one or more neural activity-dependent fluorescent moieties; collect fluorescence from the region at the second end of the same light conduit of the plurality of light conduits used to illuminate the region; and record an image including all of the terminal cross-sections of the multimode optical fibers at the first end of the light conduits onto a frame of the image detector. In some embodiments, the one or more multimode optical fibers have a diameter in the range of 100 to 1000 µm. In some embodiments, the numerical aperture of the multimode optical fiber is 0.30 or greater. In some embodiments, the second end is configured to be implanted in the target tissue.

In any embodiment, each of the light conduits may include: an implantable fiber-optic element including an attachment element; and one or more multimode optical fibers configured to attach to the attachment element.

In any embodiment, the plurality of wavelengths may include a wavelength at an isosbestic point of the one or more neural activity-dependent fluorescent moieties.

In any embodiment, the plurality of wavelengths may include a plurality of wavelengths at an excitation wavelength of a plurality of neural activity-dependent fluorescent moieties.

In any embodiment, the plurality of wavelengths may include one or more wavelengths at an activation wavelength of one or more light-activated polypeptides.

In any embodiment, the light source may be a light-emitting diode (LED) or a laser.

In any embodiment, the image detector may be a charge-coupled device (CCD) or a complementary metal oxide semiconductor (CMOS) camera.

In any embodiment, the system further may include an image splitter positioned in front of the image detector.

In any embodiment, the system may further include: e) a processor; and f) a computer-readable medium containing instructions that, when executed by the processor, causes the system to: generate a light stimulus containing i) a first set of light pulses at a first wavelength; and ii) a second set of light pulses at one or more wavelengths, each of the one or more wavelengths different from the first wavelength, using the illumination unit, wherein the one or more wavelengths are each at the excitation wavelength of the one or more neural activity-dependent fluorescent moieties, and wherein each light pulse of the first set are interleaved among light pulses of the second set, thereby generate fluorescence from each of the one or more regions; and record the image onto independent frames of the image detector per each light pulse. In some cases, the one or more wavelengths include two or more wavelengths.

BRIEF DESCRIPTION OF THE DRAWINGS

FIGS. 2A-2H are a collection of diagrams and graphs showing dual-color imaging of different populations and simultaneous recording and perturbation of neural activity according to embodiments of the present disclosure.

FIGS. 3A-3C are a collection of diagrams and graphs showing synchronous camera and photoreceiver measurements of reward-related photometry signals in the VTA, according to embodiments of the present disclosure.

FIG. 12A-12F provide amino acid sequences of ReaChR and bReachES polypeptides.

FIG. 13A-13S provide amino acid sequences of single-fluorescent protein genetically encoded calcium indicators.

FIG. 14A-14C provide amino acid sequences of multi-fluorescent protein genetically encoded calcium indicators.

FIG. 15A-15U provide amino acid sequences of various light-responsive polypeptides.

DEFINITIONS

Figure 1A:
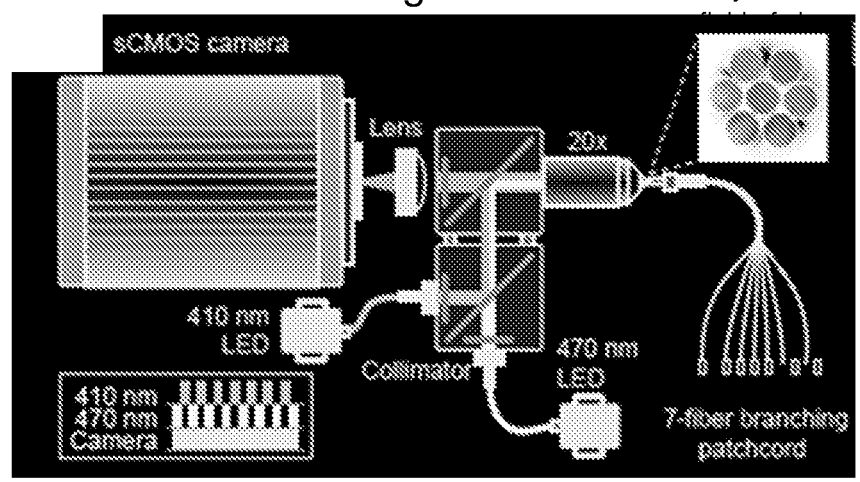
FIGS. 1A-1H are a collection of diagrams and graphs showing simultaneous calcium measurements from multiple deep brain regions using an sCMOS camera, according to embodiments of the present disclosure.
Figure 1B:
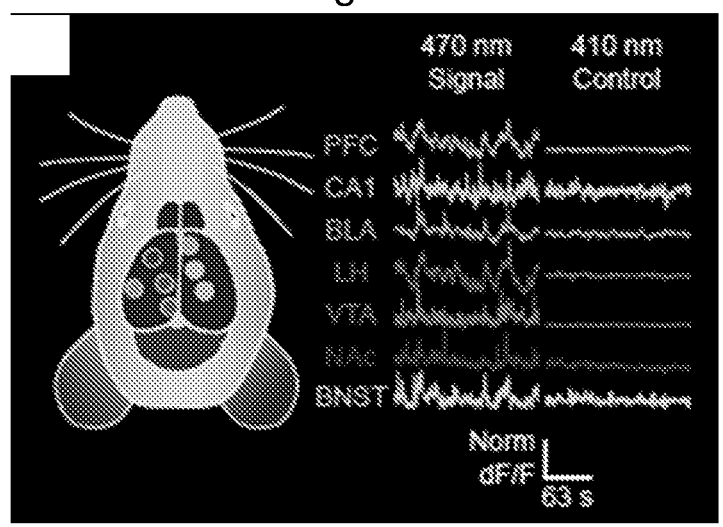

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Substantially" as used herein, may be applied to modify any quantitative representation that could permissibly vary without resulting in a change in the basic function to which it is related.

"Representative" as used herein, may be used to indicate that a variation in an underlying phenomenon is related to a quantity, e.g., a measured quantity by an experimentally-defined relationship.

"Cellular electrical activity" as used herein, refers to activity of cells that are related to changes in the concentration of ionic species (e.g., sodium ions, potassium ions, calcium ions, etc.) within the cell. Electrical activity may include changes in the intracellular concentration of ions, such as calcium ions caused by, e.g., opening or closing of ion channels in the plasma membrane, endoplasmic reticulum; activation or inactivation of ion pumps or transporters; etc. Electrical activity may include changes in membrane potential caused by changes in the concentration gradient of ionic species across the plasma membrane. Cellular electrical activity may include neural activity, i.e., cellular electrical activity of a neuron or a collection of neurons.

"Interleaved" as used herein, may be used to describe a relationship between a first event and two second events, where the first event occurs in between the two second events, and where the first event does not overlap with either of the two second events. In some cases, any two consecutive events may occur substantially immediately one after another.

A "wavelength" as used herein, may include a band of wavelength values centered on a specific wavelength value. The width of the band of wavelength values may vary and may depend on the desired and/or practical level of differentiation between different excitation and emission lights used in the present optical method and system.

"Excitation wavelength" as used in reference to a neural-activity dependent fluorescent moiety, refers to the wavelength by which the fluorescent moiety is excited generates an emission that is representative of neural activity. In some cases, the excitation wavelength is the optimal wavelength at which neural-activity dependent fluorescence is emitted by the fluorescent moiety.

"Isosbestic point" as used herein, may refer to a wavelength at which the total absorbance (i.e., fluorescence) of a neural-activity dependent fluorescent moiety does not change regardless of the electrophysiological state of the cellular milieu. Thus, a calcium indicator in a neuron stimulated by light having a wavelength substantially at the isosbestic point of the calcium indicator will emit the same intensity of fluorescence regardless of the concentration of calcium in the neuron, within the physiological range.

"Working distance" as used herein, refers to the distance between the front edge of the objective lens (e.g. the surface of the front lens closest to the sample being observed in a typical light microscope setup) and the surface of the sample being observed (i.e. the surface of the cover glass) when the observed sample is in focus. Working distance may also indicate the location in front of the objective where a sample would be in focus.

"Terminus" as used in reference to an optical fiber, refers to an end where light enters or exits the optical fiber.

"Cross-section" as used in reference to an optical fiber, refers to an area defined by an intersection between the optical fiber and a plane substantially perpendicular to the direction of travel of bulk light through the optical fiber.

An "image detector," as used herein, refers to an optical detection and/or recording device that measures light intensity across individual pixels of an optical sensor, where the spatial distribution of the individual pixels corresponds to a spatial distribution of the source of the light. Thus, an image detector may simultaneously capture the spatial distribution of light intensities in a light pattern emitted from a sample.

"Frame" as used herein, may refer to a single two-dimensional image captured by exposing the image sensor of an image detector to light collected onto the image sensor for a desired amount of time.

"Aggregate" as used herein, may be used to indicate a property or characteristic of a population without regard to the individual contributions to the property or characteristic. Thus, an aggregate neural activity may indicate the neural activity of a population of neurons without providing any underlying information about the activity of any one of the individual neurons in the population, except in the case where the population is a single neuron.

"Synchronous" as used herein, may be applied to any two or more sequences of events that occur with a temporal pattern that is substantially the same. Events in the two or more sequences that are synchronous may start at substantially the same times, may have a midpoint within events that are at substantially the same times, and/or end at substantially the same times. "Simultaneous" may indicate two events that are synchronous and substantially coextensive in duration.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an image" includes a plurality of such images and reference to "the region of a target tissue" includes reference to one or more regions of a target tissue and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, methods and systems optically recording cellular electrical activity, e.g., intracellular calcium dynamics, in one or more regions of a target tissue are provided. The present methods and systems provide for rapid, simultaneous optical recording of cellular electrical activity-dependent fluorescence emitted by a collection of electrically excitable cells, e.g., neurons, that are labeled with a cellular electrical activity-dependent fluorescent moiety in one or more regions of a target tissue. The simultaneous recording may be scaled to a number of regions within a target tissue, such that the cellular electrical activity-dependent fluorescence emitted by a collection of electrically excitable cells in two or more regions may be recorded simultaneously. In some embodiments, the present methods and systems provide for simultaneous recording of cellular electrical activity-dependent fluorescence emitted by a plurality of collections of electrically excitable cells in a region, using a plurality of cellular electrical activity-dependent fluorescent moieties. In some embodiments, the present methods and systems provide for optically modulating the electrical activity of cells that contain a light-activated polypeptide in conjunction with recording electrical activity. Further aspects of the present methods and systems are now described in detail.

Systems

A system of the present disclosure may be described with reference to the accompanying figures. However, it is noted that the figures may show an example of the specific components of an embodiments of the present system, and that other embodiments of the present system is envisioned to be within the scope of this disclosure, by substituting the specific components with equivalent structural and/or equivalent functional components known in the art.

Figure 8A:
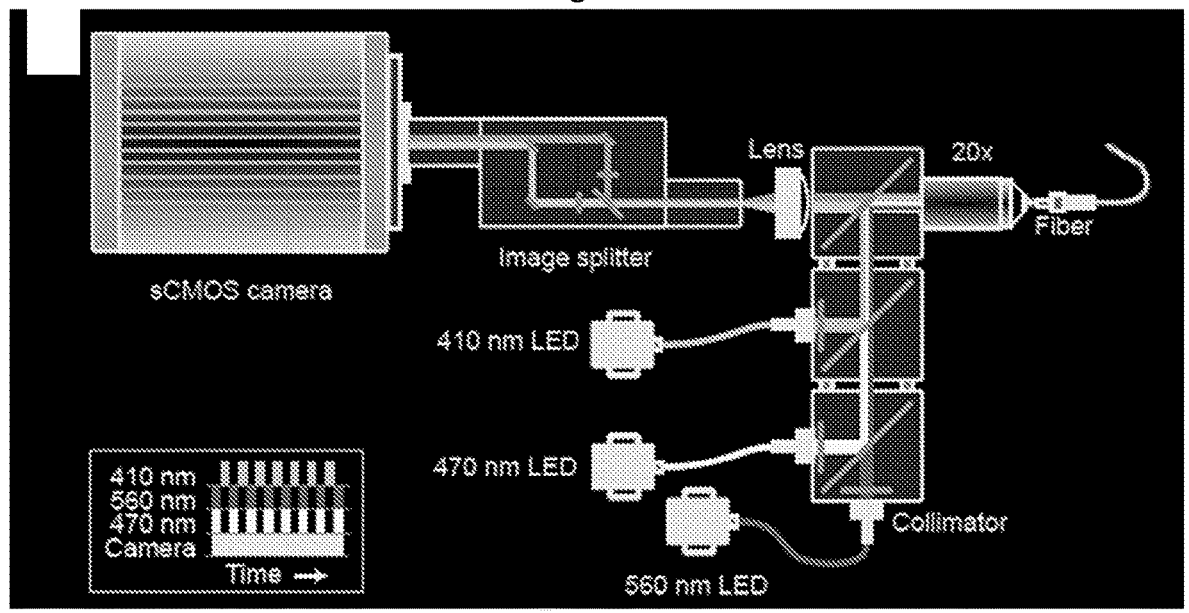
FIGS. 8A and 8B are a collection of diagrams showing microscope configurations used for dual-color imaging and simultaneous imaging and perturbation experiments, according to embodiments of the present disclosure.
Figure 8B:
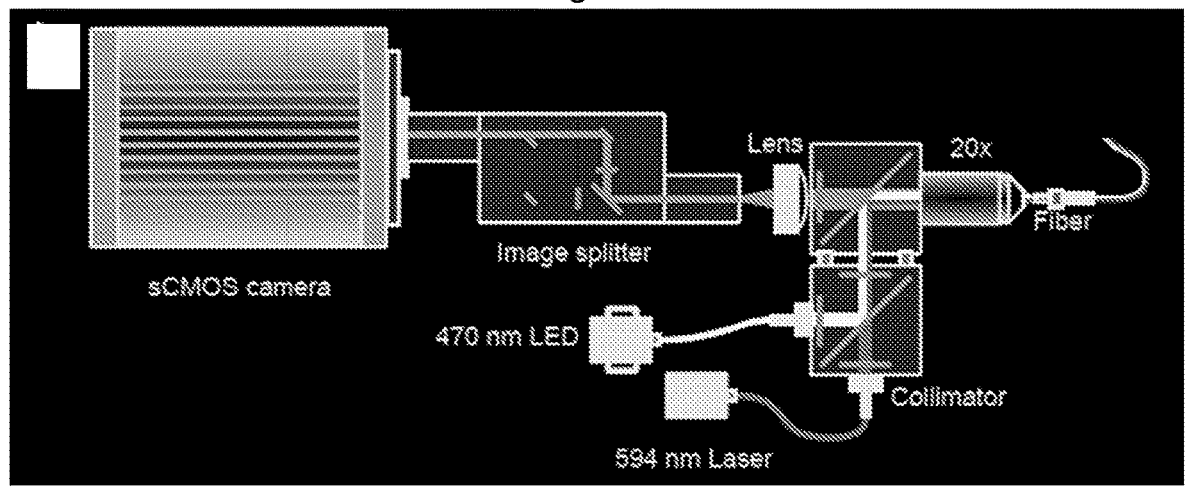

A system of the present disclosure includes an illumination unit, including one or more light sources, e.g., a light-emitting diode (LED) and/or a laser light source, that may be configured to emit light at a suitable wavelength (FIGS. 1A, 8A and 8B). Having multiple light sources can allow the user to control the illumination pattern, e.g., the timing of light pulses, for each light source independently of each other. The illumination unit may also include any other suitable optical components to direct, focus and otherwise control the light being generated by the light source. Suitable optical components include, but are not limited to, lenses, tube lenses, collimators, dichroic mirrors, filters, shutters, etc. Thus, the illumination unit may be configured to project a light stimulus that includes light pulses of a number of wavelengths. A controller may be in communication with the illumination unit so as to control the timing, duration, and/or wavelength of the light pulse generated by the illumination unit.

The present system may also include an objective placed in the optical path of the system so as to focus light from the illumination unit at the working distance of the objective. In front of the object, a bundle of optical fibers, e.g., multimode optical fibers, is positioned such that the terminal cross-sections of some or all of the optical fibers are focused and in the field of view of the objective (FIG. 1A, top right inset). The numerical aperture of the optical fiber can be less than the numerical aperture of the objective. The bundle of optical fibers may be part of a multi-fiber branching patchcord that terminates in a number of separate optic fiber branches. The ends of the optic fiber branches may be equipped with a ferrule, e.g., a stainless steel ferrule, to allow attachment to optic fibers that are implanted in a tissue, e.g., implanted to position the fiber ends in different regions of a brain in a subject, such as a mouse or rat (see FIGS. 1B, 1F, 2A and 2E). Thus, the light stimulus generated by the light sources and projected to the back of the objective through the optical light path can be directed into the optical fibers and simultaneously illuminate multiple, distinct regions of the brain where the branched optic fiber ends are implanted.

The same optical fibers used to deliver the light stimulus to the target regions of a tissue are also configured to collect fluorescence that is emitted from the target areas. Thus, the target regions may contain a population of neurons that are genetically modified to express a neural activity-dependent fluorescent moiety, such as a genetically encoded calcium indicator. When a target region is stimulated with a light stimulus having a wavelength at or around the excitation wavelength of the neural activity-dependent fluorescent moiety, the illuminated neurons may emit fluorescence that is representative of the level of neural activity in the region. The fluorescence from an individual neuron may be representative of the activity level of the individual neuron. The fluorescence collected from two or more neurons may be representative of the average activity level of the neurons. By "average" is meant the arithmetic mean.

The fluorescence emitted from the target tissue and collected by the optical fibers is directed back to and collected by the objective, and further directed to an image sensor of an image detector, e.g. a digital camera. The optical path of the collected fluorescence may include any suitable components, such as a dichroic mirror and lenses, to form an image of the terminal cross-sections of the optical fibers onto the image sensor and capture the image with the image detector. In some cases, an image splitter may be positioned in the light path before, e.g., in front of, the image detector (FIG. 8A). In such cases, an appropriate configuration of the image splitter can divide the fluorescence emitted from the tissue based on the wavelength and separate images for different wavelengths of fluorescence may be captured by the image detector simultaneously.

The light source of a system of the present disclosure may include any suitable light source. In some cases, the light source is an LED, an LED array or a laser. The light source may emit light having a wavelength in the infrared range, near-infrared range, visible range, and/or ultra-violet range. The light source may emit a light at a wavelength around 350 nm or more, e.g., around 380 nm or more, around 410 nm or more, around 440 nm or more, around 470 nm or more, around 500 nm or more, around 560 nm or more, around 594 nm or more, around 600 nm or more, around 620 nm or more, around 650 nm or more, around 680 nm or more, around 700 nm or more, around 750 nm or more, around 800 nm or more, including around 900 nm or more, and may emit a light at a wavelength around 2,000 nm or less, e.g., around 1,500 nm or less, 1,000 nm or less, 800 nm or less, 700 nm or less, 650 nm or less, including 620 nm or less, or 600 nm or less. In some cases, the light source may emit a light at a wavelength in the range of about 350 nm to about 2,000 nm, e.g., about 410 nm to about 2,000 nm, about 440 nm to about 1,000 nm, about 440 nm to about 800 nm, including about 440 nm to about 620 nm. The light source may be configured to produce a continuous wave, a quasi-continuous wave, or a pulsed wave light beam. In certain embodiments, a laser light source is a gas laser, solid state laser, a dye laser, semiconductor laser (e.g., a diode laser), or a fiber laser.

The number of wavelengths produced by the light source may be any suitable number of wavelengths. In some cases, the light source produces light with 1 or more, e.g., 2 or more, 3 or more, including 4 or more, or 5 or more, or 6 or more, or 7 or more, or 8 or more, or 9 or more, or 10 or more, distinct wavelengths of light, and produces light with 10 or fewer, e.g., 9 or fewer, 8 or fewer, 7 or less, 6 or fewer, including 5 or fewer distinct wavelengths of light. In some embodiments, the light source produces light in the range of 1 to 10, e.g., 1 to 8, 2 to 6, 2 to 5, including 2 to 4 distinct wavelengths.

The objective may be any suitable objective for use in the present system. The objective may be an air objective, oil objective, water objective, a water and air objective, etc. The objective may have any suitable numerical aperture for use in the present system. In some cases, the objective has a numerical aperture of 0.3 or more, e.g., 0.4 or more, 0.5 or more, including 0.6 or more, and has a numerical aperture of 1.6 or less, e.g., 1.4 or less, 1.2 or less, 1.0 or less, 0.9 or less, including 0.8 or less. In some cases, the objective has a numerical aperture in the range of 0.3 to 1.6, e.g., 0.3 to 1.4, 0.4 to 1.2, 0.5 to 1.0, including 0.5 to 0.9. In some cases, the numerical aperture of the objective is greater than the numerical aperture of an individual optical fiber that is used to probe a single region in the tissue.

The magnification of the objective may be any suitable magnification, and may be 4× or more, e.g., 10× or more, 20× or more, 40× or more, including 60× or more, and may be 100× or less, 80× or less, 60× or less, including 20× or less. In certain embodiments, the magnification of the objective may be in the range of 4× to 100×, e.g., 10× to 60×, including 10× to 40×.

Any suitable optical fibers may be used in the present system. The optical fiber may be a multimode optical fiber. In some instances, a multimode optical fiber supports more than one propagation mode. For example, a multimode optical fiber may be configured to carry a range of wavelengths of light, where each wavelength of light propagates at a different speed.

The optical fiber may include a core defining a core diameter, where light from the light source passes through the core. The core may be further surrounded by a cladding. The core diameter of an individual optical fiber that is used to probe a single region in the tissue may vary, and may be any suitable core diameter. In some cases, the core diameter is greater than the wavelength of light carried by the optical fiber. For example, the core diameter of an optical fiber may be 10 μm or more, e.g., 50 μm or more, 100 μm or more, 200 μm or more, including 300 μm or more, and may be 1,000 μm or less, e.g., 900 μm or less, 800 μm or less, 700 μm or less, including 600 μm or less. In some embodiments, the core diameter of the individual optical fiber may be in the range of 10 to 1,000 μm, e.g., 50 to 1,000 μm, 100 to 1,000 μm, 200 to 800 μm, including 300 to 600 μm.

In some instances, the cladding surrounds at least a portion of the core of the optical fiber. For instance, the cladding may surround substantially the entire outer circumferential surface of the optical fiber. In some cases, the cladding is not present on the ends of the optical fiber, such as at the end of the optical fiber that receives and transmits light to and from the illuminating unit, and the opposite end of the optical fiber that receives and transmits light to and from the neurons in the target region of interest in the subject. The cladding may be any suitable type of cladding. In some cases, the cladding has a lower refractive index than the core of the optical fiber. Suitable materials for the cladding include, but are not limited to, plastic, resin, and the like, and combinations thereof.

In some cases, the optical fiber includes an outer coating. The outer coating may be disposed on the surface of the cladding. The coating may surround substantially the entire outer circumferential surface of the optical fiber. In some cases, the coating is not present on the ends of the optical fiber, such as at the end of the optical fiber that receives and transmits light to and from the illuminating unit, and the opposite end of the optical fiber that receives and transmits light to and from the neurons in the target region of interest in the subject. The coating may be a biologically compatible coating. A biologically compatible coating includes coatings that do not significantly react with tissues, fluids, or other substances present in the subject into which the optical fiber is inserted. In some cases, a biologically compatible coating is composed of a material that is inert (i.e., non-reactive) with respect to the surrounding environment in which the optical fiber is used.

The numerical aperture of an individual optical fiber that is used to probe a single region in the tissue may vary, and can be less than the numerical aperture of the objective. Stated another way, the numerical aperture of the objective can be greater than the numerical aperture of an individual optical fiber that is used to probe a single region in the tissue. In some cases, the numerical aperture of the individual optical fiber is 90% or less, e.g., 80% or less, 75% or less, 70% or less, 65% or less, and is 10% or more, 20% or more, 30% or more, 40% or more, 50% or more, including 60% or more, of the objective numerical aperture. In some cases, the numerical aperture of the individual optical fiber is in the range of 10% to 90%, e.g., 20% to 80%, 30% to 75%, 40% to 70%, including 50% to 65%, of the objective numerical aperture. In some cases, the numerical aperture of the individual optical fiber is 0.01 or more, e.g., 0.1 or more, 0.2 or more, 0.3 or more, including 0.4 or more, and is 1.4 or less, e.g., 1.2 or less, 1.0 or less, 0.8 or less, 0.6 or less, including 0.5 or less. In certain embodiments, the numerical aperture of the individual optical fiber is in the range of 0.01 to 1.4, e.g., 0.1 to 1.0, 0.2 to 0.8, including 0.3 to 0.6.

The number of optical fibers that form the optical fiber bundle, each of which are used to direct light stimulus from the objective and to provide illumination to an individual region of the target tissue, may vary, and may be any suitable number. In some cases, the number of optical fibers in the optical fiber bundle is one or more, e.g., 2 or more, 3 or more, 4 or more, 5 or more, 6 or more, 7 or more, including 10 or more, and is 100 or less, e.g., 80 or less, 60 or less, 40 or less, 20 or less, 15 or less, 10 or less, 8 or less, 7 or less, 6 or less, including 5 or less. In certain embodiments, the number of optical fibers is in the range of 1 to 100, e.g., 2 to 60, 3 to 40, 4 to 20, including 4 to 10.

The optical fiber end that is implanted into the target tissue may have any suitable configuration suitable for illuminating a region of the tissue with a light stimulus delivered through the optical fiber and for collecting fluorescence from the illuminated region.

In some cases, the optical fiber patchcord that directs the light stimulus from the objective ends with an attachment device at each of the branched ends, where the attachment device is configured to connect to an optical fiber that is implanted in the target tissue. Any suitable attachment device may be used. In some cases, the attachment device includes a ferrule, e.g., a metal, ceramic or plastic ferrule. The ferrule may have any suitable dimensions. In some cases, the ferrule has a diameter in the range of 0.5 to 3 mm, e.g., 0.75 to 2.5 mm, or 1 to 2 mm.

The image detector may be any suitable image detector. In some instances, the image detector is a digital camera, such as a complementary metal-oxide-semiconductor (CMOS) camera (e.g., a scientific CMOS (sCMOS) camera), or a charge-coupled device (CCD) camera (e.g., an electron-multiplying CCD (EMCCD) camera). In some cases, the image detector includes an image sensor, which is configured to detect light directed to the image detector by the optical fiber.

The present system may include any suitable electronic components to control and/or coordinate the various optical components. The optical components of the present system may be controlled by a controller, e.g., to coordinate the illumination unit illuminating the sample with light pulses of different wavelengths and/or the recording of the image with the image detector. The controllers may include a driver for the light sources that control the intensity and/or frequency of the light pulses. The controller (e.g., the driver for the light sources) may also be configured to control the wavelength of light emitted from an individual light source. The controllers may be in communication with components of the illumination unit (e.g. the light sources, collimators, shutters, filter wheels, moveable mirrors, lenses, etc.) and the image detector.

In some embodiments, the present system includes a computational unit configured to control and/or coordinate the light stimulus and image capture through one or more controllers, and to analyze images recorded by the image detector. A computational unit of the present system may include any suitable components to analyze the recorded images. Thus, the system may include one or more of the following: a processor; a non-transient, computer-readable memory, such as a computer-readable medium; an input unit, such as a keyboard, mouse, touchscreen, etc.; an output unit, such as a monitor, screen, speaker, etc.; a network interface, such as a wired or wireless network interface; and the like.

In some cases, the system may include a computer-readable medium containing instructions that can be executed by a processor, which in turn causes the system to perform any suitable portion of a method of the present disclosure, using components of the system.

Methods

A general implementation of a method of the present disclosure may include first illuminating a region or several regions of a target tissue (e.g., several distinct regions of the target tissue) with a light stimulus. The light stimulus includes light centered around a suitable wavelength and pulsed at a known interval to generate a generally intermittent pattern of illumination for a particular wavelength. The light may be pulsed at a regular interval, defined by a frequency and a pulse length. The light pattern may also be defined by a duty cycle, where the duty cycle is the percentage of a time period during which a signal, i.e., the light, is on.

The light stimulus may include a first set of light pulses at a first wavelength, and a second set of light pulses at one or more wavelengths. In some cases, the first wavelength is different from the one or more wavelengths in the second set of light pulses. The second set of light pulses may include one or more subsets of light pulses, each subset having a wavelength. In some instances, the second set of light pulses includes two or more subsets of light pulses, each subset having a different wavelength. The second set of light pulses may include a first subset of light pulses at a second wavelength, and the second set of light pulses may further include a second subset of light pulses at a third wavelength, and so on up until any suitable number of subsets of light pulses. In some cases, the wavelength of the light pulses of the first set is a different wavelength from the one or more wavelengths of light pulses of the second set. For example, the wavelength of the light pulses of the first set is a different wavelength from the second wavelength, and the wavelength of the light pulses of the first set is a different wavelength from the third wavelength.

The light pulses of the first set and the light pulses of the second set may be timed so that they do not overlap with each other. Thus, in some cases, each light pulse of the first set is interleaved among light pulses of the second set. In some cases, light pulses of the first set and light pulses of the second set alternate one after another (FIG. 1A, lower left inset, where 410 nm light pulses alternate with 470 nm light pulses). In some cases, the light pulses of the first set are timed to be at every other interval between light pulses of the second set (i.e., at half the frequency of the light pulses of the second set). Any other suitable relative timing of light pulses of the first set and second set may be used, where the light pulses of the first set and the light pulses of the second set do not overlap with each other. Light pulses of different subsets of the second set may be timed to be synchronous, simultaneous, and/or may be overlapping, or may not be overlapping.

The light stimulus is delivered to a region in a tissue of interest by a light conduit that includes one or more optical fibers, e.g., one or more multimode optical fibers, where one end of the conduit collects the light stimulus (e.g., light stimulus generated by an illumination unit and focused with an objective, as described above) and the other end is configured to illuminate the region in the tissue with the light stimulus. For example, the other end of the conduit may be configured to be implanted into the tissue at the region to illuminate the region with the light stimulus.

Each region illuminated by the light stimulus may contain excitable cells, e.g., neurons that contain one or more cellular electrical activity-dependent fluorescent moieties, e.g., neural activity-dependent fluorescent moieties, such as a genetically-encoded calcium indicator. Thus, the cells labeled with a cellular electrical activity-dependent fluorescent moiety may emit fluorescent when stimulated by a light stimulus of an appropriate wavelength and intensity, where the intensity of the fluorescence depends on the electrical activity of the cell. In some cases, an electrically active cell, e.g., a more depolarized cell, labeled with a cellular electrical activity-dependent fluorescent moiety will emit a stronger fluorescence when stimulated by a light stimulus at the excitation wavelength of the activity-dependent fluorescent moiety and having sufficient intensity compared to a cell that is not electrically active, e.g., a more hyperpolarized cell, labeled with the activity-dependent fluorescent moiety and stimulated by the same light stimulus. Depending on the wavelength of the light pulses, the region may emit fluorescence that is activity-dependent, or activity-independent.

The wavelength of light pulses of the second set may be at an excitation wavelength of a cellular electrical activity-dependent fluorescent moiety in the cells of the region illuminated by the light stimulus. Thus, a labeled cell in a region can emit a fluorescence that is representative of the activity level of the cell when the region is illuminated by at least some of the light pulses of the second set.

The fluorescence emitted by the illuminated region can be collected by the same optical fiber used to deliver the light stimulus, e.g., the same optical fiber implanted at the illuminated region. Thus, a single optical fiber illuminates cells in a single region of the tissue of interest, and collects the fluorescence emitted by the labeled cells in the region. When the region is illuminated by a light pulse having a wavelength at the excitation wavelength of the activity-dependent fluorescent moiety, the collected fluorescence may be representative of an average level of activity of the cells in the region.

The present method can include recording, at the end of the optical fiber opposite the implanted end, the fluorescence collected at the implanted end of the optical fiber. The recording may be done by an image detector (e.g., a digital camera) configured to capture an image of the cross-section of the terminal end of the optical fiber. As the optical fiber collects fluorescence representative of an average level of activity of the cells in the region at the implanted end, the fluorescence emitted at the recording end is also representative of an average level of cellular activity of the region.

In some instances, the fluorescence emitted at the recording end of the optical fiber does not preserve the spatial information about the origin of fluorescence with respect to individual cells within the region illuminated by the optical fiber. Thus, the average level of fluorescence across the terminal cross-section of the optical fiber recorded by the image detector may be indicative of the aggregate activity of labeled cells in the illuminated region.

The image detector may be controlled to separately record at least one image for the duration of each light pulse. In other words, a set of one or more images may be recorded for fluorescence emitted in response to a light pulse of the first set of light pulses, and a separate set of one or more images may be recorded for fluorescence emitted in response to a light pulse (which may include one or more wavelengths of light pulses from one or more subset of light pulses) of the second set of light pulses. In some cases, a single image is recorded for each light pulse. In some cases, a single image is recorded for each light pulse of the second set of light pulses. Any other suitable timing of recording may be used. Any number of images may be recorded to obtain an image stack that shows a change in fluorescence emitted by the region of the target tissue over time.

The present method can include analyzing the recorded image, or a portion thereof, to obtain a measure of the cellular electrical activity level of the region of the target tissue. Any suitable method may be used to analyze the image. In some cases, the analyzing includes selecting a region of interest within which region the level of fluorescence is to be measured. As the images can contain the terminal cross-section of the optical fibers, the analyzing may include demarcating the terminal cross-section as the region of interest and measuring the fluorescence intensity within the terminal cross-section. The analyzing may include calculating the average intensity of fluorescence over the region of interest. The analyzing may include any other suitable data processing procedures, including, but limited to, background subtracting, normalizing, thresholding, curve fitting, subtracting bleaching artifacts, smoothing, etc., and combinations thereof.

The target tissue may be any suitable target tissue that contains one or more regions with electrically excitable cells. In some cases, the target tissue includes a plurality of regions with electrically excitable cells that are functionally interconnected, such that electrical activity in one region can modulate the electrical activity in another region. The electrically excitable cell may be any suitable electrically excitable cell, including, but not limited to a neuron or muscle cell. In some cases, the target tissue is neural tissue, e.g., brain, spinal cord, etc. In some cases, the target tissue is the heart, gastrointestinal tract, lung, skeletal muscle, etc.

In some cases, the method further includes illuminating a region in a target tissue with a first set of light pulses at the isosbestic point of a cellular electrical activity-dependent fluorescent moiety used to label the excitable cells in the region. The fluorescence signal emitted in response to the first set of light pulses may then be independent of the level of electrical activity of the excitable cell. Thus, the recorded trace of the fluorescence signal obtained at the isosbestic point of the cellular electrical activity-dependent fluorescent moiety may serve as a control to correct for, e.g., subtract out, the non-cellular electrical activity-related component in the measured cellular electrical activity-dependent fluorescence level.

In certain embodiments, the present method further includes illuminating a region in a target tissue, where the region includes neurons that contain either one or both of two cellular electrical activity-dependent fluorescent moieties and the two activity-dependent fluorescent moieties have different (and distinguishable) excitation and emission wavelengths. Thus, the second set of light pulses used to illuminate the region may include two subsets of light pulses at different wavelengths, each of which is at the excitation wavelength of one or the other activity-dependent fluorescent moiety. Light pulses of the two subsets may be simultaneous, synchronous, or non-overlapping. The fluorescence emitted from the illuminated region may include fluorescence at two wavelengths, each of which may be representative of cellular electrical activity in the cell that is labeled with the activity-dependent fluorescent moiety that produced the respective fluorescence. Thus, in some cases, a first collection of cells may be labeled with a first activity-dependent fluorescent moiety, which emits fluorescence at a first wavelength that is representative of cellular electrical activity in the first collection of cells, and a second collection of cells may be labeled with a second activity-dependent fluorescent moiety, which emits fluorescence at a second wavelength that is representative of cellular electrical activity in the second collection of cells. The activity-dependent fluorescence at the two different wavelengths can be collected simultaneously with the optical fiber (e.g., multimode optical fiber) that illuminated the region, and the combined fluorescence can be directed to the image detector and recorded. In some cases, the fluorescence emitted from the region is split, e.g., using an image splitter, to from separate images for the fluorescence emitted by the cells expressing the first activity-dependent fluorescent moiety and for the fluorescence emitted by the cells expressing the second activity-dependent fluorescent moiety. Thus, the method may include recording a first image of the terminal cross-section of the optical fiber for a region, where the a cross-sectional average of the fluorescence is representative of an aggregate neural activity of a first collection of neurons labeled with the first neural activity-dependent fluorescent moiety, and a second image of the terminal cross-section of the optical fiber for a region, where the a cross-sectional average of the fluorescence is representative of an aggregate neural activity of a second collection of neurons labeled with the second neural activity-dependent fluorescent moiety. As such, the aggregate neural activities of the first collection of neurons and the second collection of neurons measured by the present method are contemporaneous aggregate neural activities. Where a region in a target tissue contains neurons that are labeled with multiple neural activity-dependent fluorescent moieties, all or at least some of the fluorescent moieties may share the same isosbestic point.

In some cases, the method includes illuminating a plurality of regions of a target tissue using a plurality of optical fibers, where each region contains a plurality of excitable cells, e.g., neurons, labeled with a cellular electrical activity-dependent fluorescent moiety, and where one optical fiber illuminates and collects fluorescence from one region. The recording may include simultaneously recording onto a frame of the image detector the terminal cross-sections of each of the optical fibers, where each optical fiber terminal cross-section conveys fluorescence that is representative of a corresponding region in the tissue at which the optical fiber is implanted. For example, the recording may include simultaneously detecting using the image sensor of the image detector light from the terminal cross-sections of each of the optical fibers. As described herein, the light detected by the image sensor may include fluorescence generated in response to the light pulses used to excite the neural activity-dependent fluorescent moieties in the region of interest.

The number of optical fibers used in the present method may vary, and may be any suitable number. In some cases, the number of optical fibers used to excite and image different regions of the target tissue is one or more, e.g., 2 or more, 3 or more, 4 or more, 5 or more, 6 or more, 7 or more, including 10 or more, and is 100 or less, e.g., 80 or less, 60 or less, 40 or less, 20 or less, 15 or less, 10 or less, 8 or less, 7 or less, 6 or less, including 5 or less. In certain embodiments, the number of optical fibers is in the range of 1 to 100, e.g., 2 to 60, 3 to 40, 4 to 20, including 4 to 10.

Any suitable optical fibers may be used in the present method. The optical fiber may be a multimode optical fiber. The optical fiber may include a core defining a core diameter, where light passes through the core. The core may be further surrounded by a cladding. The core diameter of an individual optical fiber that is used to probe a single region in the tissue may vary, and may be 10 µm or more, e.g., 50 µm or more, 100 µm or more, 200 µm or more, including 300 µm or more, and may be 1,000 µm or less, e.g., 900 µm or less, 800 µm or less, 700 µm or less, including 600 µm or less. In some embodiments, the core diameter of the individual optical fiber may be in the range of 10 to 1,000 µm, e.g., 50 to 1,000 µm, 100 to 1,000 µm, 200 to 800 µm, including 300 to 600 µm.

The numerical aperture of an individual optical fiber that is used to probe a single region in the tissue may vary, and can be less than the numerical aperture of the objective. In some cases, the numerical aperture of the individual optical fiber is 90% or less, e.g., 80% or less, 75% or less, 70% or less, 65% or less, and is 10% or more, 20% or more, 30% or more, 40% or more, 50% or more, including 60% or more, of the objective numerical aperture. In some cases, the numerical aperture of the individual optical fiber is in the range of 10% to 90%, e.g., 20% to 80%, 30% to 75%, 40% to 70%, including 50% to 65%, of the objective numerical aperture. In some cases, the numerical aperture of the individual optical fiber is 0.01 or more, e.g., 0.1 or more, 0.2 or more, 0.3 or more, including 0.4 or more, and is 1.4 or less, e.g., 1.2 or less, 1.0 or less, 0.8 or less, 0.6 or less, including 0.5 or less. In certain embodiments, the numerical aperture of the individual optical fiber is in the range of 0.01 to 1.4, e.g., 0.1 to 1.0, 0.2 to 0.8, including 0.3 to 0.6.

The present method may use any suitable image detector. In some instances, the image detector is a digital camera, such as a CMOS camera (e.g., a sCMOS camera), or a charge-coupled device (CCD) camera (e.g., an electron-multiplying CCD (EMCCD) camera).

The collection of neurons whose activity is to be measured by the present method may be any suitable collection of neurons. In some cases, a collection of neurons is defined by a known functional classification. Any convenient functional classification may be used to define the collection of neuron. In some cases, the collection of neurons includes excitatory neurons, inhibitory neurons, sensory neurons, motor neurons, interneurons, etc. In some cases, the collection of neurons includes dopaminergic, cholinergic, GABAergic, glutamatergic, or peptidergic neurons. In some cases, the collection of neurons includes Purkinje cells, pyramidal cells, golgi cells, Lugaro cells, basket cells, candelabrum cells, granule cells, stellate cells, unipolar brush cells, medium spiny neurons, Renshaw cells, spindle cells, etc. The different functional cells may be labeled specifically with a cellular electrical activity-dependent fluorescent moiety using any suitable method. In some cases, a cell-specific promoter, or a combination of different cell-specific promoters, may be used to control expression of a genetically-encoded cellular electrical activity-dependent fluorescent moiety, e.g., a genetically-encoded calcium indicator, specifically in a functionally-defined collection of neurons.

The target tissue can be a human target tissue (e.g., an in vivo, in vitro, or ex vivo target tissue). The target tissue can be a non-human animal target tissue (e.g., an in vivo, in vitro, or ex vivo target tissue). Non-human animals include non-human primates, murines (e.g., rats, mice), lagomorphs (e.g., rabbits), ungulates, felines, canines, and the like. The target tissue can be in a live human or non-human animal. The target tissue can be in a freely-moving human or non-human animal.

The present method may include illuminating any suitable region of the target tissue, e.g., the brain. In some cases, the method includes illuminating a functionally and/or anatomically defined region of a brain, e.g., a amphibian brain, a reptile brain, a bird brain, a marsupial brain, mammalian brain, etc. In some cases, the method includes illuminating at least of portion of the ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyrus, entorhinal cortex, olfactory cortex, sensory cortex, thalamus, primary motor cortex, and cerebellum, etc., of a mammalian brain. Any other suitable functionally and/or anatomically defined region of a mammalian brain may be illuminated in the present method.

In some cases, the method includes illuminating a region of the brain where the cell body of labeled neurons is present. In some cases, the method includes illuminating a region of the brain where the neuronal projections, e.g., axonal projections, dendritic projections, etc., of labeled neurons are present.

In some cases, where two or more regions are illuminated and whose cellular electrical activities are recorded, the method includes illuminating regions that are functionally distinct. Two regions may be functionally distinct by being two distinct anatomical regions. Two regions may be functionally distinct by containing different functional types of population of neurons. Two regions may be functionally distinct by having distinct types of inputs or outputs to other regions of the brain, and/or different functional types of neurons. Two regions may be functionally distinct by any other suitable criteria.

In some cases, two or more regions that are illuminated and whose cellular electrical activity is recorded by the present method may be functionally connected regions of the target tissue, e.g., the brain. A functionally connected regions of the brain may have neurons from one region that are connected on average to neurons of a second region by a minimum number of synaptic connections of one or more, e.g., two or more, 3 or more, 4 or more, including 5 or more, and by a minimum number of synaptic connections of 10 or less, 9 or less, 8 or less, 7 or less, 6 or less 5 or less, 4 or less, including 3 or less.

In some embodiments, the target tissue whose region(s) are illuminated and whose cellular electrical activity is recorded by the present method is an in vivo tissue, or an ex vivo tissue (e.g., a tissue slice). In some cases, the target tissue is in a freely moving animal, or is in a head-fixed animal. In some cases, the target tissue is in an animal that has been exposed to an environmental manipulation. In some cases, the target tissue is in an animal that has been conditioned to respond, behaviorally and/or neurologically, more reliably to a stimulus compared to an animal that has not been conditioned. In some cases, the animal is a water-deprived animal; a water-deprived animal rewarded with water; a food-deprived animal; a food-deprived animal rewarded with food; a solitary animal; an animal in the presence of another animal of the same species; an animal presented with an aversive stimulus, e.g., an electric shock, aversive sounds, such as a loud noise, extreme temperatures, repulsive odors, etc.; an animal presented with a novel object; an animal navigating a maze; an animal performing a memory/recollection task; etc.

The present method may employ any suitable frequency of light pulses. In some cases, the frequency of the light pulses is 0.1 Hz or more, e.g., 1 Hz or more, 5 Hz or more, 10 Hz or more, 15 Hz or more, 20 Hz or more, including 25 Hz or more, and is 1,000 Hz or less, e.g., 500 Hz or less, 200 Hz or less, 100 Hz or less, 80 Hz or less, including 60 Hz or less. In certain embodiments, the frequency of the light pulses is in the range of 0.1 to 1,000 Hz, e.g., 1 to 500 Hz, 1 to 200 Hz, 5 to 80 Hz, 10 to 60 Hz, including 15 to 60 Hz.

The present method may employ any suitable duration of a pulse of light to illuminate a region in a target tissue. In some cases, the duration of a light pulse is 1.0 ms or more, e.g., 2.0 ms or more, 5.0 ms or more, 10.0 ms or more, 15 ms or more, 20 ms or more, including 25 ms or more, and is 1,000 ms or less, e.g., 500 ms or more, 300 ms or less, 200 ms or less, 100 ms or less, 50 ms or less, including 40 ms or less. In some embodiments, the duration of a light pulse is in the range of 1.0 to 1,000 ms, e.g., 2.0 to 500 ms, 5.0 to 200 ms, 10.0 to 100 ms, including 15 to 50 ms.

The present method may employ any suitable duty cycle for the pulse of light used to illuminate a region in a target tissue. In some cases, the duty cycle of the light pulse is 5% or more, such as 10% or more, or 15% or more or 20% or more, or 25% or more, or 30% or more, or 35% or more, or 40% or more, or 45% or more, or 50% or more, or 55% or more, or 60% or more, or 65% or more, or 70% or more, or 75% or more, including 100% or less, such as 95% or less, or 90% or less, or 85% or less, or 80% or less, or 75% or less, or 70% or less, or 65% or less, or 60% or less, or 55% or less, or 50% or less. In some embodiments, the duty cycle of the light pulse is in the range of 5% to 75%, such as 10% to 70%, or 10% to 65%, or 10% to 60%, or 10% to 55%, or 10% to 50%, or 15% to 45%, or 15% to 40%, or 15% to 35%, or 20% to 30%. In certain instances, the duty cycle of the light pulse is 25%.

The power of the light pulses used to illuminate a region of a target tissue may be any suitable power. The power of the light pulse may be the power measured at the end of the patchcord, i.e., at the end of the optical fiber at the surface of the target tissue. In some cases, a light pulse for exciting a cellular electrical activity-dependent fluorescent moiety has a power of 0.5 µW or more, e.g., 1.0 µW or more, 2.0 µW or more, 3.0 µW or more, 5 µW or more, 10 µW or more, 15 µW or more, including 20 µW or more, and has a power of 500 µW or less, e.g., 250 µW or less, 200 µW or less, 150 µW or less, 100 µW or less, 50 µW or less, including 30 µW or less. In some cases, a light pulse for exciting a cellular electrical activity-dependent fluorescent moiety has a power in the range of 0.5 to 500 µW, e.g., 1.0 to 250 µW, 1.0 to 200 µW, 2.0 to 100 µW, 3.0 to 50 µW, including 3.0 to 30 µW. In some cases, a light pulse for exciting a cellular electrical activity-dependent fluorescent moiety has a power of 0.5 mW or more, e.g., 1.0 mW or more, 2.0 mW or more, including 5.0 mW or more, and has a power of 10 mW or less, e.g., 8.0 mW or less, 6.0 mW or less, 4.0 mW or less, including 3.0 mW or less. In some cases, a light pulse for exciting a cellular electrical activity-dependent fluorescent moiety has a power in the range of 0.5 to 10 mW, e.g., 1.0 to 8.0 mW, including 1.0 to 6.0 mW.

In some embodiments, a region illuminated by the light stimulus may contain excitable cells, e.g., neurons, that contain one or more light-activated polypeptides, e.g., light-activated ion channels or ion pumps, which, when activated by a light pulse at the activation wavelength, can modulate the electrical activity of the cells. The light-activated polypeptide may be any suitable light-activated polypeptide for modulating the activity of an excitable cell in a light-dependent manner, as described further below. The light-activated polypeptide may be a genetically encoded light-activated polypeptide expressed in the cell.

The region that is illuminated by an optical fiber, according to embodiments of the present method, may contain cells that contain both a cellular electrical activity-dependent fluorescent moiety and a light-activated polypeptide, or may contain cells that have either one of the two. Thus, the region may contain a first collection of cells that are labeled with the cellular electrical activity-dependent fluorescent moiety, and a second collection of cells that contain the light-activated polypeptide. The first collection of cells and the second collection of cells may be substantially the same collection of cells (i.e., the cells in the region contain both the cellular electrical activity-dependent fluorescent moiety and the light-activated polypeptide, if any). Alternatively, the first collection of cells and the second collection of cells may be distinct but overlapping collections of cells (i.e., some cells in the region contain both the cellular electrical activity-dependent fluorescent moiety and the light-activated polypeptide, while other cells in the region contain either the cellular electrical activity-dependent fluorescent moiety or the light-activated polypeptide, if any). In some cases, the first collection of cells and the second collection of cells may be substantially non-overlapping collections of cells (i.e., the cells in the region contain either the cellular electrical activity-dependent fluorescent moiety or the light-activated polypeptide, if any). The cells expressing the light-activated polypeptide may be a functionally-defined population of cells, as described elsewhere.

Where the region contains a collection of cells containing a light-activated polypeptide, the wavelength of the first set of light pulses may be at the activation wavelength of the light-activated polypeptide. The power of the light pulses at the activation wavelength of the light-activated polypeptide may be any suitable power for activating the light-activated polypeptide and modulating cellular electrical activity in the region. In some cases, the power of the light pulses at the activation wavelength of the light-activated polypeptide is 0.01 mW or more, e.g., 0.05 mW or more, 0.1 mW or more, 0.5 mW or more, 1.0 mW or more, 5.0 mW or more, including 10.0 mW or more, and is 50 mW or less, e.g., 40 mW or less, 30 mW or less, 20 mW or less, 10 mW or less, 5.0 mW or less, 4.0 mW or less, 3.0 mW or less, 2.0 mW or less, including 1 mW or less. In some cases, the power of the light pulses at the activation wavelength of the light-activated polypeptide is in the range of 0.01 to 50 mW, e.g., 0.05 to 5.0 mW, 0.1 mW to 4.0 mW, including 0.1 mW to 3 mW.

In some cases, the power of the light pulses at the activation wavelength of the light-activated polypeptide is sufficient to generate electrical activity in the cell that approximates electrical activity that is generated by a natural stimulus, i.e., a stimulus that is provided to the animal in which the target tissue resides as a whole, rather than specifically only to those cells that contain the light-activated polypeptide in the form of a light pulse. A natural stimulus may be a sensory stimulus provided to a sensory organ of the animal, such as, but not limited to, light to the visual system, tactile stimulus to the somatosensory system, sound to the auditory system, tastant to the gustatory system, odor to the olfactory system, etc. In some cases the natural stimulus is a reward stimulus, e.g., a water reward and/or food reward. In some cases, the natural stimulus is an aversive stimulus, e.g., an electric shock, aversive sounds, such as a loud noise, extreme temperatures, repulsive odors, etc. In some cases, the natural stimulus is a novel object. In some cases, the natural stimulus is a social cue. In some cases, the natural stimulus is a task, such as navigating a maze or performing a memory/recollection task, etc.

The activation of the light-activated polypeptide using the appropriate wavelength and power of light pulse may induce electrical activity in the cell that has a similar maximum magnitude of response as the electrical activity induced by a natural stimulus, as measured by the level of fluorescence from a neural activity-dependent fluorescent moiety expressed in the same cell. The cellular electrical activity induced by activation of the light-activated polypeptide may have a maximum magnitude that is 50% or more, e.g., 60% or more, 70% or more, 80% or more, 90% or more, 95% or more, including 100% or more, and is 200% or less, e.g., 150% or less, 120% or less, 110% or less, including 100% or less than the maximum magnitude of the cellular electrical activity induced by a natural stimulus. In some cases, the cellular electrical activity induced by activation of the light-activated polypeptide may have a maximum magnitude in the range of 50 to 200%, e.g., 60 to 150%, 70 to 120%, including 80 to 110% of the maximum magnitude of the cellular electrical activity induced by a natural stimulus. In some cases, the cellular electrical activity induced by activation of the light-activated polypeptide may have a duration of response above background that is 50% or more, e.g., 60% or more, 70% or more, 80% or more, 90% or more, 95% or more, including 100% or more, and is 200% or less, e.g., 150% or less, 120% or less, 110% or less, including 100% or less than the duration of response above background of the cellular electrical activity induced by a natural stimulus. In some cases, the cellular electrical activity induced by activation of the light-activated polypeptide may have a duration of response above background in the range of 50 to 200%, e.g., 60 to 150%, 70 to 120%, including 80 to 110% of the duration of response above background of the cellular electrical activity induced by a natural stimulus. In some cases, the cellular electrical activity induced by activation of the light-activated polypeptide may have a response latency that is 50% or more, e.g., 60% or more, 70% or more, 80% or more, 90% or more, 95% or more, including 100% or more, and is 200% or less, e.g., 150% or less, 120% or less, 110% or less, including 100% or less than the response latency of the cellular electrical activity induced by a natural stimulus. In some cases, the cellular electrical activity induced by activation of the light-activated polypeptide may have a response latency in the range of 50 to 200%, e.g., 60 to 150%, 70 to 120%, including 80 to 110% of the response latency of the cellular electrical activity induced by a natural stimulus.

In some cases, where the region contains a first collection of cells containing a light-activated polypeptide and a second collection of cells labeled with an electrical activity-dependent fluorescent moiety, the light pulse having a wavelength at the excitation wavelength of the electrical activity-dependent fluorescent moiety has a power that is sufficiently low that the light pulse does not cause activation of the light-activated polypeptide to significantly modulate electrical activity of the cell, as measured by the fluorescence from the electrical activity-dependent fluorescent moiety. In some cases, the light pulse having a wavelength at the excitation wavelength of the electrical activity-dependent fluorescent moiety has a power of 50 µW or less, e.g., 30 µW or less, 15 µW or less, 10 µW or less, including 8.0 µW or less, and has a power of 0.5 µW or more, e.g., 1.0 µW or more, 2.0 µW or more, including 3.0 µW or more. In some cases, the light pulse having a wavelength at the excitation wavelength of the electrical activity-dependent fluorescent moiety has a power in the range of 0.5 to 50 µW, e.g., 1.0 to 30 µW, 1.0 to 15 µW, 1.0 to 10 µW, including 1.0 to 8 µW.

The region may contain any suitable number of distinct collections of cells, where each collection of cells is labeled with a different electrical activity-dependent fluorescent moiety. In some cases, the region contains 1 or more, e.g., 2 or more, 3 or more, including 4 or more, distinct collections of cells, and contains 10 or fewer, e.g., 9 or fewer, 8 or fewer, 7 or less, 6 or fewer, including 5 or fewer distinct collections of cells. In some cases, the region contains in the range of 1 to 10, e.g., 1 to 8, 2 to 6, 2 to 5, including 2 to 4 collections of cells. In some cases, the method includes illuminating the region with a light stimulus containing light pulses at an excitation wavelength for some or all of the different electrical activity-dependent fluorescent moieties in the region. For example, a multimode optical fiber as described herein may be used to illuminate the region with a light stimulus containing two or more light pulses at different excitation wavelengths for different electrical activity-dependent fluorescent moieties in the region.

The present method can be a rapid method of measuring cellular electrical activity, e.g., neural activity, in one or more regions of a target tissue, e.g., a brain. In some cases, the present method provides real-time measurement of cellular electrical activity, in one or more regions of a target tissue. In some cases, the method can be performed in 20 ms or less, e.g., 10 ms or less, 8 ms or less, 6 ms or less, 5 ms or less, 4 ms or less, including 3 ms or less, and can be performed in 1 ms or more, 2 ms or more, 3 ms or more, including 4 ms or more. In some cases, the method can be performed in a range of 1 to 20 ms, e.g., 1 to 10 ms, 2 to 8 ms, including 2 to 6 ms. In some cases, the aggregate neural activity of 2 or more, e.g., 3 or more, 5 or more, 7 or more, including 10 or more, and 50 or less, e.g., 30 or less, 20 or less, including 15 or less regions of a target tissue can be analyzed synchronously using the present method in 20 ms or less, e.g., 10 ms or less, 8 ms or less, 6 ms or less, 5 ms or less, 4 ms or less, including 3 ms or less, and can be performed in 1 ms or more, 2 ms or more, 3 ms or more, including 4 ms or more. In some cases, the aggregate neural activity of 2 or more, e.g., 3 or more, 5 or more, 7 or more, including 10 or more, and 50 or less, e.g., 30 or less, 20 or less, including 15 or less regions of a target tissue can be analyzed synchronously using the present method in 1 to 20 ms, e.g., 1 to 10 ms, 2 to 8 ms, including 2 to 6 ms.

In some embodiments, the method is a method for closed-loop control of cellular electrical activity in a target tissue. In some cases, where a first region of the target tissue contains a collection of cells containing a light-activated polypeptide, the method further includes illuminating the first region with the cells containing a light-activated polypeptide with a light pulse at the activation wavelength of the light-activated polypeptide, where the timing and/or power of the illuminating the first region with the cells containing a light-activated polypeptide is based on an recorded image of a terminal cross-section of an optical fiber from a second region and the analysis of the aggregate neural activity in the second region. Thus, in some cases, the analysis of the aggregate neural activity in the second region may indicate that first region should be illuminated by a light pulse to activate a depolarizing light-activated polypeptide at a certain intensity and for a specific duration, e.g., to compensate for a lack of activity in the second region. In some cases, the analysis of the aggregate neural activity in the second region may indicate that first region should be illuminated by a light pulse to activate a hyperpolarizing light-activated polypeptide at a certain intensity and for a specific duration, e.g., to reduce hyperactivity in the second region.

Cellular Electrical Activity-Dependent Fluorescent Moieties

The cellular electrical activity-dependent fluorescent moieties, e.g., the neural activity-dependent fluorescent moieties, may include any suitable fluorescent moiety whose fluorescence properties are responsive to the electrical activity of the cell in which it resides. Fluorescent moieties whose fluorescence properties are sensitive to cellular electrical activity include ratiometric/non-ratiometric dyes and fluorescent proteins. Fluorescent moieties whose fluorescence properties are sensitive to cellular electrical activity may be a fluorescence resonance energy transfer (FRET)-based reporter. Fluorescent moieties whose fluorescence properties are sensitive to cellular electrical activity may be sensitive to changes in intracellular concentration of ions such as calcium, sodium and protons or to changes in membrane potential. In such cases, fluorescent dyes of interest include, but are not limited to, calcium indicator dyes (Indo-1, Fura-2, and Fluo-3, Calcium Green®, Fluo-4, etc.); sodium indicator dyes (sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.).

Cellular electrical activity-dependent fluorescent proteins of interest include, but are not limited to, genetically encoded calcium indicators (Cameleon, Pericam, TN-XXL, Twitch, GECO, GCaMP1, GCaMP2, GCaMP3, GCaMP6 and derivatives thereof, as well as those cited in U.S. Pat. No. 8,629,256, and Tian et al. 2012 Prog Brain Res, 196:79, which are incorporated herein by reference); and genetically encoded voltage indicators (QuasAr1, QuasAr2, VSFP, and derivatives thereof, as well as those cited in US App. Pub. No. 2013/0224756, Hochbaum et al., Nat Methods 2014 11:825, Baker et al. Brain Cell Biol 2008 36:53; and Mutoh et al., Exp Physiol 2011 96:13, each of which are incorporated herein by reference). Other suitable GCaMP-based genetically encoded calcium indicators include GCaMP2.1, GCaMP2.2a, GCaMP2.2b, GCaMP2.3, GCaMP2.4, GCaMP3, GCaMP5g, GCaMP6m, GCaMP6s, GCaMP6f, etc. Suitable GECO-based genetically encoded calcium indicators include G-GECO1, G-GECO1.1 and G-GECO1.2, the red fluorescing indicator R-GECO1, the blue fluorescing indicator B-GECO1, the emission ratiometic indicator GEM-GECO1, and the excitation ratiometric GEX-GECO1, etc.

A suitable genetically encoded calcium indicator polypeptide can comprise an amino acid sequence having at least 75%, at least 80%, at least 85%, at least 90%, at least 95%, at least 98%, at least 99%, or 100%, amino acid sequence identity with an amino acid sequence set forth in FIG. 13A-13S. A suitable genetically encoded calcium indicator polypeptide can comprise an amino acid sequence having at least 75%, at least 80%, at least 85%, at least 90%, at least 95%, at least 98%, at least 99%, or 100%, amino acid sequence identity with an amino acid sequence set forth in FIGS. 14A-14C.

In some cases, the fluorescent moiety may be sensitive to biochemical changes in the excitable cell, such as changes in enzymatic activity (e.g., activation of kinases); changes in binding interactions (e.g., binding of transcription factors to DNA); changes in subcellular localization of proteins; etc. Exemplary fluorescent moieties are further described in, e.g, Mehta et al., Annu Rev Biochem. 2011; 80: 375, which is incorporated herein by reference.

Light-Activated Polypeptides

Where region of the target tissue includes cells that contain a light-activated polypeptide, the light-activated polypeptide may be any suitable light-activated polypeptide for modulating the electrical activity of the cell with a light stimulus. In some instances, the light-activated polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-activated polypeptide depolarizes the cell when activated by light of an activating wavelength. In some embodiments, the light-activated polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChIEF, Chronos, ChRGR, CsChrimson, and the like. In some cases, the light-activated polypeptide includes bReaCh-ES, as described herein and described further in, e.g., Rajasethupathy et al., Nature. 2015 Oct. 29; 526(7575):653, which is incorporated by reference. Hyperpolarizing and depolarizing opsins have been described in various publications; see, e.g., Berndt and Deisseroth (2015) Science 349:590; Berndt et al. (2014) Science 344:420; and Guru et al. (Jul. 25, 2015) Intl. J. Neuropsychopharmacol. 18:pyv079 (PMID 26209858).

As non-limiting examples, a suitable light-activated polypeptide can comprise an amino acid sequence having at least 75%, at least 80%, at least 85%, at least 90%, at least 95%, at least 98%, at least 99%, or 100%, amino acid sequence identity with an amino acid sequence set forth in any one of FIG. 15A-15U. A bReaChES light-activated polypeptide can comprise an amino acid sequence having at least 75%, at least 80%, at least 85%, at least 90%, at least 95%, at least 98%, at least 99%, or 100%, amino acid sequence identity with an amino acid sequence set forth in any one of FIG. 12B-12F.

Cells in a region of the target tissue may be labeled with a cellular activity-dependent fluorescent moiety and/or the light-activated polypeptide may be introduced into the cells using any suitable method. In some cases, the cells in the region are genetically modified to express a genetically-encoded fluorescent moiety, e.g., a genetically-encoded calcium or voltage indicator, and/or a light-activated polypeptide. In some cases, the cells may be genetically modified using a viral vector, e.g., an adeno-associated viral vector, containing a nucleic acid having a nucleotide sequence that encodes the cellular activity-dependent fluorescent moiety and/or a light-activated polypeptide. The viral vector may include any suitable control elements (e.g., promoters, enhancers, recombination sites, etc.) to control expression of the cellular activity-dependent fluorescent moiety and/or a light-activated polypeptide according to cell type, timing, presence of an inducer, etc.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) *Cell* 51:7-19; and Llewellyn et al. (2010) *Nat. Med.* 16:1161); a serotonin receptor promoter (see, e.g., GenBank S62283); a tyrosine hydroxylase promoter (TH) (see, e.g., *Nucl. Acids. Res.* 15:2363-2384 (1987) and *Neuron* 6:583-594 (1991)); a GnRH promoter (see, e.g., Radovick et al., *Proc. Natl. Acad. Sci. USA* 88:3402-3406 (1991)); an L7 promoter (see, e.g., Oberdick et al., *Science* 248:223-226 (1990)); a DNMT promoter (see, e.g., Bartge et al., *Proc. Natl. Acad. Sci. USA* 85:3648-3652 (1988)); an enkephalin promoter (see, e.g., Comb et al., *EMBO J.* 17:3793-3805 (1988)); a myelin basic protein (MBP) promoter; a CMV enhancer/platelet-derived growth factor-β promoter (see, e.g., Liu et al. (2004) *Gene Therapy* 11:52-60); a motor neuron-specific gene Hb9 promoter (see, e.g., U.S. Pat. No. 7,632,679; and Lee et al. (2004) *Development* 131:3295-3306); and an alpha subunit of $Ca^{2+}$-calmodulin-dependent protein kinase II (CaMKIIα) promoter (see, e.g., Mayford et al. (1996) *Proc. Natl. Acad. Sci. USA* 93:13250). Other suitable promoters include elongation factor (EF) 1α and dopamine transporter (DAT) promoters.

In some cases, cell type-specific expression of the cellular activity-dependent fluorescent moiety and/or a light-activated polypeptide may be achieved by using recombination systems, e.g., Cre-Lox recombination, Flp-FRT recombination, etc. Cell type-specific expression of genes using recombination has been described in, e.g., Fenno et al., *Nat Methods.* 2014 July; 11(7):763; and Gompf et al., *Front Behav Neurosci.* 2015 Jul. 2; 9:152, each of which are incorporated by reference herein.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Ø denotes the core diameter. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Materials and Methods

The following materials and methods were used in the Examples.

Core Frame-Projected Independent-Fiber Photometry (FIP) Platform Setup and Modifications The main FIP platform included a widefield microscope imaging a bundle of one or more (up to 7 in this example) fiber faces, with a series of dichroic mirrors integrated in the microscope to be able to simultaneously couple in various wavelength excitation light sources. Custom MATLAB® (Mathworks) software was used to control the timing of the various excitation light sources, to synchronously acquire camera frames, and to digitally sum and compute the total fluorescence from each of the fibers in each camera frame in real-time. The excitation light sources, dichroics, and acquisition timing protocols were reconfigurable to support combinations of dual-color recording, simultaneous recording and stimulation, and concurrent acquisition of isosbestic control signals.

A custom patchcord of 7 bundled 400 µm Ø 0.48 numerical aperture (NA) fibers (Doric Lenses) was used for FIP experiments. One end of the patchcord terminated in a SubMiniature version A (SMA) connector mounted (Thorlabs, SM1SMA) at the working distance of the objective, while the other end terminated in 7 individual 1.25 mm Ø stainless steel ferrules. These ferrules were coupled via ceramic sleeves (Thorlabs, ADAL1) to 1.25 mm Ø ferrules implanted into a mouse.

The fiber faces were imaged through a 20×/0.75 NA objective (Nikon, CFI Plan Apo Lambda 20×) through a series of reconfigurable dichroic mirrors. Fluorescence emission from the fibers passed through a 535 nm bandpass fluorescence emission filter (selected for GCaMP recording; Semrock FF01-535/22-25). The fluorescence image was focused onto the sensor of a scientific complementary metal-oxide semiconductor (sCMOS) camera (Hamamatsu ORCA®-Flash4.0) through a tube lens (Thorlabs AC254-035-A-ML). The reconfigurable dichroic mirrors were mounted in removable dichroic cube holders (Thorlabs, DFM1), and enabled two total light sources to be coupled in. In the standard configuration, a 470 nm light emitting diode (LED) (Thorlabs, M470F1), was fiber coupled into the dichroic cube holder by using a 1000 µm Ø, 0.48 NA fiber (Thorlabs, M71L01) and a 405 nm, f=4.02 mm, 0.6 NA collimator (Thorlabs, F671SMA-405 and AD11F) with a 495 nm longpass dichroic mirror (Semrock, FF495-Di02-25×36). This produced an excitation spot of ~2.5 mm Ø (10 mm÷4.02 mm×1000 µm) at the working distance of the 20× objective (focal length of ~10 mm). This spot was sufficiently large to fill all of the fibers of the 7-fiber branching patchcord. Typically the light powers emitted from the different fibers were within 25-50% of each other. All of the LEDs used were controlled by a driver enabling digital modulation up to 1 kHz (Thorlabs, LEDD1B). See Example 2 for additional system design, alignment, and calibration considerations.

Time-division multiplexing. To enable the concurrent recording of multiple channels per fiber (or for simultaneous optogenetic stimulation), a time-division multiplexing strategy was used to time-sequentially sample each channel individually. Schematics of the time-division multiplexing strategy used for each experiment are shown in FIG. 1A, FIG. 8B, and FIG. 2F. Briefly, for GCaMP6 imaging, consecutive camera frames were captured using alternating 470 nm and 410 nm excitation sources; i.e., every other camera frame was captured using either 470 nm or 410 nm light. For example if the camera is capturing images at 40 Hz, the individual 470 nm and 410 nm signals are sampled at 20 Hz. For simultaneous GCaMP6 and R-CaMP2 imaging, camera frames were captured using alternating excitation sources of either 470 nm+560 nm or 410 nm alone. For simultaneous GCaMP6 imaging and optogenetic stimulation, camera frames were captured only with 470 nm excitation light, and additional 470 nm or 594 nm stimulation light pulses were independently controlled.

Setup for concurrent acquisition of isosbestic control. For measurements of GCaMP6 emission, both a 405 nm LED and a 470 nm LED (Thorlabs, M405F1 and M470F1) were used as excitation sources for the calcium-dependent and calcium-independent isosbestic control measurements, respectively. The two LEDs were filtered with a 410-10 nm and 470-10 nm 1" Ø bandpass filters (Thorlabs, FB410-10 and FB470-10), fiber coupled as described above, combined using a 425 nm longpass dichroic mirror (Thorlabs, DMLP425R) and coupled into the microscope using a 495 nm longpass dichroic mirror (Semrock, FF495-Di02-25×36).

Dual-color recording setup. To enable simultaneous GCaMP6 and R-CaMP2 recording, the 535 nm bandpass emission filter was removed and an image splitter (Photometrics, DualView-Lambda®) was introduced in between the camera and the tube lens, enabling us to record the GCaMP6 and R-CaMP2 emission onto separate halves of the same camera sensor. Inside the image splitter, a 555 nm dichroic mirror (Semrock, FF555-Di03-25×36) separates the emission into two channels, each of which are additionally filtered by a 600-37 nm (Semrock, FF01-600/37-25) and 520-35 nm emission filters (Semrock, FF01-520/35-25), respectively, and then projected onto the camera sensor. An additional dichroic cube allowed us to incorporate a 565 nm LED (Thorlabs, M565F1) for R-CaMP2 excitation with a 560-14 nm excitation filter (Semrock, FF01-560/14-25), in conjunction with the 410 nm and 470 nm LEDs as described previously for GCaMP6 recording. Each of the three LEDs was coupled via a 1000 µm Ø, 0.48 NA fiber (Thorlabs) to either a 405 nm f=4.02 mm, 0.6 NA collimator (410 nm and 470 nm LED; Thorlabs, F671SMA-405 and AD11F) or a 543 nm f=4.34 NA collimator (560 nm LED; Thorlabs, F230SMA-A). The 410 nm and 470 nm output from the collimators were first combined with a 425 nm longpass dichroic mirror (Thorlabs, DMLP425R), and then combined with the 560 nm light using a second 520 nm dichroic, (Semrock, FF520-Di02-25×36), before finally being coupled into the microscope using a third multi-band dichroic (Semrock, FF410/504/582/669-Di01-25×36).

Setup for simultaneous recording and stimulation. For combined imaging and optogenetic stimulation, the 565 nm LED used for dual-color recording was replaced with a 594 nm laser (Cobolt, Mambo 100 mW). The 594 nm laser was filtered with a 590-10 nm bandpass filter (Thorlabs FB590-10). An additional 525-39 nm green fluorescent protein (GFP) emission filter (Semrock, FF01-525/39-25) was placed in front of the tube lens, along with a 594 nm notch filter (Semrock, NF03-594E-25) to minimize direct laser emission detected by the camera. A multi-band dichroic (Semrock, Di01-R405/488/594-25×36) was used to reflect 470 nm and 594 nm excitation light into the back of the 20× objective. A high-speed shutter (Stanford Research Systems, SR474) was placed in front of the laser to modulate the emission in synchrony with the other LEDs and camera.

For 470 nm cross-stimulation experiments, to enable the delivery of 470 nm excitation light at two different power levels, the 594 nm laser was replaced with another 470 nm LED, and the dichroic combining the 470 nm and 594 nm light was replaced with a 50:50 beamsplitter. During the cross-stimulation experiments, one 470 nm LED was set to a lower power and activated for every camera exposure, while the other 470 nm LED was set to a similar or higher power and activated only during the stimulation periods.

Setup for sCMOS and lock-in amplifier photoreceiver comparison. In order to precisely replicate the previous photoreceiver lock-in detection approach, an optical chopping wheel was introduced after the collimated 470 nm LED (Thorlabs, MC1510 and MC2000), and coupled it to the microscope via a 200 µm Ø, 0.39 NA fiber (Thorlabs, M75L01) and a 543 nm, f=7.86 mm, 0.51 NA collimator (Thorlabs, F240FC-A and AD12F) to illuminate only the center~254 µm Ø region of the 400 µm Ø patchcord (~10 mm (objective focal length)÷7.86 mm×200 µm). This alignment was achieved by positioning the collimator using a 5-axis kinematic mount (Thorlabs, K5X1) and using the camera to visualize both the 400 µm Ø imaging patchcord, and the size of the excitation spot from the 200 µm Ø fiber-coupled LED using a fluorescent slide (Chroma, 92001) mounted at the working distance of the objective. For this experiment, the 470 nm LED was the only excitation light source used with a 470 nm 1" Ø bandpass filter (Thorlabs, FB470-10) and a 495 nm longpass dichroic mirror (Semrock, FF495-Di02-25×36). Lastly, the signal from the optical chopping wheel was synchronized to a lock-in amplifier (Stanford Research, SR810 DSP), the output of which was sampled and digitized at 10 kHz using data acquisition hardware (National Instruments, NI PCIe-6343-X).

Image Acquisition Using MATLAB®

Though the technique described here could be implemented using the standalone image acquisition software for the sCMOS camera and digital function generators to control the light sources, custom MATLAB® software was used to control all hardware and streamline data acquisition. All software ran on a Dell T5600 computer running Windows® 7 (64-bit). A custom Matlab® graphical user interface (GUI) controlled both the sCMOS camera through the MATLAB® Image Acquisition Toolbox and the LED light sources through a data acquisition hardware (DAQ) (National Instruments, NI PCIe-6343-X) and the MATLAB® Data Acquisition ToolBox. To minimize raw data volume for real-time applications, the camera was set to 4-by-4 pixel binning and semi-automatically located a subregion containing only each of the fiber ends from which to acquire data. Using this software, the 7 fiber signals from the raw camera frame can be calculated within ~2-3 ms (measured when collecting both calcium and isosbestic signals at 40 Hz, and given the computer's configurations). Separate scripts for each experiment generated digital control signals to operate any mouse behavior peripheral hardware. The GUI software and example behavior control scripts are available at https (colon)//github(dot)com/deisseroth-lab/multifiber.

Head-Fixed Apparatus and Stimulus Delivery

Except for during the freely moving 7-fiber recordings, mice were head-fixed above an animal running wheel (Ware, Small 6" wheel) using a custom machined head-plate holder. Custom-written Matlab® scripts delivered digital control signals to trigger water rewards and tail shocks synchronized to the camera imaging. Water rewards were delivered through a small animal feeding tube (Popper and Sons, 16 gauge) connected to a normally-closed solenoid (Valcor, SV74P61T-1). The solenoid was powered by a 12V DC battery, and the power was gated by a metal-oxide-semiconductor field-effect transistor (MOSFET) (Mouser Electronics). The solenoid was opened for 0.25-0.5 s, which resulted in water droplets a few 10 s of μL in size. Tail shocks were administered using a stimulus isolator (WPI, Isostim A320R). The positive and negative leads of the isolator were connected by lead wires (Roscoe Medical, WW3005) to two pre-gelled electrodes (Sonic Technology) that were attached to the mouse's tail.

Analysis

All analysis was performed using custom-written scripts in MATLAB®. Regions of interest (ROIs) were first manually drawn around the fiber(s) based on a mean image of the movie. The average fluorescence intensity was calculated for each fiber. A "dark frame" image was acquired by taking a movie with the patchcord attached to the mouse, but with no LEDs on. This offset value accounts for extraneous, non-genetically-encoded calcium indicator (GECI) related light contributing to the signal. This offset was subtracted from the fluorescence intensity for each fiber, and then the fluorescence time series was thresholded to remove large transients. A double exponential was then fit to the fluorescence time series, and the best fit was subtracted in order to account for slow bleaching artifacts. A single baseline fluorescence value was calculated, either as the median of the entire trace (which robustly estimated the baseline fluorescence), or by manually defining the baseline during visually-identified periods of rest. The normalized change in fluorescence (dF/F) was calculated by subtracting the baseline fluorescence from the fiber fluorescence at each time point, and dividing this value by the baseline fluorescence. For 7-fiber experiments, the dF/F was further normalized by the maximum value for each fiber. For analysis shown in FIGS. 1C-1E, the 410 nm reference trace was scaled to best fit the 470 nm signal using least-squares regression. The scaled 410 nm reference trace was then subtracted from the 470 nm signal to obtain the motion-corrected 470 nm signal. Other than the plots shown in FIG. 1B for the 7-fiber imaging, no additional smoothing or filtering was applied to fluorescence measurements. For FIG. 1B, a 1 s average sliding window was applied to the traces. To calculate correlation coefficients, MATLAB®'S "con" function was used. To ensure that the increase in correlation during the social interactions was significantly greater than what one would expect from merely increased activity, each fiber's trace was circularly permuted 1,000 times using a random shift between 0 and 5 minutes. For each shuffle, the pooled mean r value was calculated across all mice and unique brain region pairs. A p-value<0.001 means that none of the mean r values calculated from the 1,000 shuffled traces were greater than the actual calculated mean r value.

Experimental Parameters sCMOS and lock-in amplifier photoreceiver experiments. Mice were water deprived to ~80% of their starting weight. Head-fixed mice were trained to lick water rewards that were delivered through an animal feeding needle. Water rewards were given as a 0.25 s opening of the solenoid, and delivered at 10 s intervals. The SNR was calculated as the peak dF/F divided by the standard deviation of the baseline dF/F. Here, the peak dF/F was the maximum value during the first 2 s of reward, and the baseline dF/F was measured during the period 0.5 s prior to reward delivery. Only a single fiber was implanted in the VTA. A low imaging power of 2.5 μW (measured at the face of a 400 μm Ø patchcord) was used. For imaging parameters, see Example 6.

Multi-fiber experiments. For the 7-fiber experiment, the branching patchcord was coupled to the ferrules implanted in the mouse with ceramic sleeves. The mouse was allowed to freely navigate its cage and socialize with a novel mouse (of the same gender and age) while calcium signals were recorded. For 7-fiber experiments, alternating frames with excitation wavelengths of 470 nm and 410 nm were imaged at 40 Hz, resulting in frame rates of 20 Hz for both the GCaMP6 calcium and isosbestic control signals. For the 4-fiber experiments, mice were water-deprived and administered either water rewards or tail shocks while head-fixed and running on a wheel. Water rewards were given as a 0.5 s opening of the solenoid, and tail shock were given as 450 ms pulses spaced 5 ms apart for 2 s (4 shocks at 0.5 Hz). Water rewards and shocks were given at 10 s intervals. The response size to reward or shock was defined as the difference between the mean stimulus dF/F during the first 1 s of the reward or shock, and the mean baseline dF/F during the 2 s prior to the reward or shock. For 4-fiber experiments, alternating pulses with excitation wavelengths of 470 nm and 410 nm were imaged at 20 Hz, resulting in frame rates of 10 Hz for both the GCaMP6 calcium and isosbestic control signals. Typically 10-20 μW of 470 nm imaging light power was used, and 410 nm LED light power was adjusted to approximately match the GCaMP6 fluorescence emission produced by the 470 nm imaging light.

Dual-color experiments. Mice were water-deprived and administered either water rewards or tail shocks while head-fixed using the same parameters as in the multi-fiber experiments. Response sizes to reward or shock were calculated as described for the multi-fiber experiments. Alternating pulses of simultaneous 470 nm and 560 nm light, and 410 nm light, were imaged at 20 Hz, resulting in frame rates of 10 Hz for GCaMP6 and R-CaMP2, and for the control signals. 10-20 μW of 470 nm and 560 nm imaging light power was used, and the 410 nm LED light power was adjusted to approximately match the GCaMP6 and R-CaMP2 fluorescence emission produced by the 470 nm and 560 nm imaging light.

Combined imaging and stimulation experiments. Mice were water-deprived and administered either optogenetic stimulation or water rewards while head-fixed using the same parameters as in the multi-fiber experiments. The response size to optogenetic stimulation or reward was defined as the difference between the mean stimulus dF/F during the first 0.5 s of the light or reward, and the mean baseline dF/F during the 0.5 s prior to the light or reward. To sample calcium signals at 20 Hz, 470 nm excitation pulses that were 12.5 ms in length and spaced 50 ms apart were used for a 25% duty cycle. The camera exposed frames only during each 470 nm excitation pulse, resulting in 25% duty cycle imaging. Additional 470 nm or 594 nm stimulation pulses were delivered in between the 470 nm imaging excitation pulses, at a rate of 20 Hz for 0.5 s (10 pulses with 12.5 ms pulse width for a 25% duty cycle). Though longer exposure times could have been used to increase the amount of signal recorded, a larger separation between the stimulation periods and the camera exposure times was chosen, so that there was no question about whether signal artifacts were being measured, where the 470 nm or 594 nm stimulation pulses contributed additional excitation of GCaMP6 within a camera exposure. A 410 nm isosbestic GCaMP control signal was not recorded for these experiments. Identical light powers for the 470 nm imaging and stimulation pulses for the 5 μW and 10 μW experiments were used. However, for the 50 μW and 220 μW 470 nm stimulation pulses, the imaging 470 nm LED was kept at 10 μW to avoid unnecessary bleaching of the GCaMP6 fluorescence, and the additional stimulation 470 nm LED was set to 50 or 220 μW. For all 594 nm stimulation pulses and water reward measurements, the imaging 470 nm LED was kept at 5 µW. For the control mouse, GCaMP6 fluorescence was recorded with 20 µW pulses of 470 nm imaging light, and identical 20 µW pulses of 470 nm stimulation light and 0.5 mW pulses of 594 nm stimulation light. GCaMP6 fluorescence with 50 µW pulses of 470 nm imaging light, and identical 50 µW pulses of 470 nm simulation light and 0.5 mW pulses of 594 nm stimulation light, were also recorded.

Cultured Neuron Intracellular Patching and Imaging for GECI Isosbestic Wavelengths Dissociated rat hippocampal neurons were cultured and transfected with both GCaMP6m and R-CaMP2 as previously described. Coverslips of cultured neurons were transferred from the culture medium to a recording bath filled with Tyrode's solution (containing in mM: 125 NaCl, 2 KCl, 2 CaCl$_2$, 2 MgCl$_2$, 30 glucose, 25 HEPES). Whole-cell patch clamp recordings were performed on healthy GECI-expressing neurons at room temperature. Resistance of the glass patch pipettes was 3-4 MS2 (Sutter Instruments, P-2000) when filled with intracellular solution containing the following (in mM): 150 K-gluconate, 5 NaCl, 1 MgCl$_2$, 0.2 EGTA, 10 HEPES, 2 Mg-ATP, 0.3 Na-GTP, adjusted to pH 7.3 with KOH. Signals were amplified with a Multiclamp 700B amplifier, and acquired using a DigiData 1440A digitizer sampled at 10 kHz and filtered at 2 kHz (Molecular Devices). All electrophysiological data acquisition was performed using pCLAMP software (Molecular Devices). Imaging was performed using a 40×/0.8 NA objective (Olympus), Rolera XR camera (Q-Imaging), and Spectra X Light excitation source (Lumencor), all coupled to an Olympus BX51 WI microscope. The following bandpass filters were used with the Lumencor for excitation wavelengths: 405-10 nm (Thorlabs, FB405-10), 470-10 nm (Thorlabs, FB470-10), and 560-10 nm (Thorlabs, FB560-10). GCaMP6m emission was reflected off a 495 dichroic mirror (Semrock, FF495-Di03-25×36) and passed through a 535-30 nm emission filter (Chroma, ET535/30m), and R-CaMP2 fluorescence was reflected off a 585 nm dichroic (Chroma, T585LP) and passed through a 630-75 nm emission filter (Chroma, ET630/75m). Images were acquired at 10 Hz using QCapture Pro7 Software (Q-imaging). While synchronously measuring GCaMP6m or R-CaMP2 fluorescence from a neuron, action potentials were driven by injecting brief current pulses (5 ms, 1-2 nA) at 10 Hz for 3 s (resulting in 30 action potentials). The response size to the stimulation train was defined as the difference between the mean stimulus dF/F during the first 3 s of the stimulation train, and the mean baseline dF/F during the 3 s prior to the stimulation train.

bReaCh-ES Design and Characterization bReaCh-ES was generated by introducing a Glu123Ser mutation in the previously published ReaChR construct (see also, Example 8). Dissociated rat hippocampal neurons were cultured and transfected with either ReaChR or bReaCh-ES. The same intracellular recording procedures were used as for the GECI isosbestic cultured neuron intracellular recordings. Action potentials were elicited with a 4 s pulse train of 590 nm light (5 ms pulse width) delivered at various frequencies, using a Spectra X Light source and 590-10 nm excitation filter (Thorlabs). Steady-state current and tau-off kinetics were measured using a constant illumination of 4 s.

Animal Surgical Procedures and Viruses

All experimental and surgical protocols were approved by Stanford University's Institutional Animal Care and Use Committee. For all surgeries, stainless steel headplates and ferrules were fixed to the skull using Metabond (Parkell). Mice were anesthetized with 1.5-2.0% isoflurane and were placed on a heating pad in a stereotaxic apparatus (Kopf Instruments). All viruses were produced at the Stanford Viral and Vector Core—GVVC (Stanford University).

For the 7-fiber surgery, DAT::Cre B6.SJL-S1c6a3tm1.1 (cre)Bkmn/J (JAX® stock 006660) male or female transgenic mice were stereotaxically injected as previously described with 1000 nL of AAVDJ-CaMKIIα-GCaMP6f (2.7e12 vg/ml) at six locations: PFC, A/P +2.2, M/L +0.35, D/V −2.2; NAc, A/P +1.15, M/L −1.65, D/V −4.2; BLA, A/P −1.54, M/L −3.0, D/V −4.6; LH, A/P −0.9, A/P −1.1, D/V −5.0; BNST, A/P +0.9, M/L +0.1, D/V −4.4; and CA1, A/P −1.75, M/L +1.5, D/V −1.25. Mice were injected with 1000 nL of AAVDJ-EF1α-DIO-GCaMP6f (1.5e13 vg/ml) in the VTA: A/P −3.1, M/L −0.4, D/V −4.4. Custom 400 µm Ø 0.48 NA fibers attached to a 1.25 mm Ø stainless steel ferrule (Doric Lenses) were stereotaxically implanted at the same seven coordinates.

For 4 fiber surgeries, DAT::Cre male or female transgenic mice were used. Mice were stereotaxically injected as previously described with 1000 nL of AAVDJ-EF1α-DIO-GCaMP6f (1.5e13 vg/ml) at two locations in the VTA: A/P −3.3, M/L −0.3 and −0.5, D/V −4.2. Custom 400 µm Ø 0.48 NA fibers attached to a 1.25 mm Ø stainless steel ferrule (Doric Lenses) were stereotaxically implanted at 4 locations: VTA, A/P −3.3, M/L −0.4, D/V −4.2; PFC, A/P +2.2, M/L −0.35, D/V −2.0; NAc, A/P +1.2, M/L −1.75, D/V −4.0; and BLA, A/P −1.54, M/L −2.8, D/V −4.5.

For dual-color R-CaMP2 and GCaMP6 imaging, 1000 nL of a 1:1 mixture of AAVDJ-hSyn-DO-GCaMP6m (2.9e12 vg/ml) and AAVDJ-EF1α-DIO-RCaMP2 (8.0e12 vg/ml) was injected into the VTA at A/P −3.3, M/L −0.4, D/V −4.2. A custom 400 µm Ø 0.48NA fiber attached to a 1.25 mm Ø stainless steel ferrule was implanted at the same location.

For GCaMP6 imaging and bReaCh-ES stimulation, 1000 nL of a 1:1 mixture of AAVDJ-EF1α-DIO-GCaMP6f (1.5e13 vg/ml) and AAVDJ-EF1α-DIO-bReaCh-ES-TS-mCherry (5.8e12 vg/ml) was injected into the VTA of a DAT::Cre mouse at A/P −3.3, M/L −0.4, D/V −4.2. A custom 400 µm Ø 0.48 NA fiber attached to a 1.25 mm Ø stainless steel ferrule was implanted at the same location. As a control, a DAT::Cre mouse was injected with 1000 nL of a 1:1 mixture of AAVDJ-EF1α-DIO-GCaMP6f (5.8e12 vg/ml) and AAV8-EF1α-DIO-mCherry (1.7e13 vg/ml) into the VTA, and implanted with a 400 µm Ø 0.48 NA fiber at the same coordinates.

Histology

Mice were heavily anesthetized with isoflurane, and then perfused with 20 mL of cold phosphate buffered saline (PBS) followed by 20 mL of cold paraformaldehyde (PFA). The brain was extracted from the skull and kept in PFA for 24 hours, and then transferred to a 30% sucrose solution. After 48 hours, the brains were sliced into 50-100 µm thick sections using a vibratome (Leica VT1200S) in cold PBS. Slices were then washed in PBS at room temperature 3 times for 5 minutes each. For GCaMP6 and tyrosine hydroxylase (TH) staining, slices were incubated in a blocking solution of PBS+0.3% Triton®-X (polyethylene glycol p-(1,1,3,3-tetramethylbutyl)-phenyl ether) (PBST) with 5% normal donkey serum (NDS) for 1 hour. Slices were then incubated for 24 hours at 4° C. in PBST+NDS blocking solution containing a primary rabbit antibody against GFP conjugated to Alexa®488 (Life Technologies, A21311, 1:500) and a primary chicken antibody against TH (Ayes Lab, 1:500). Slices were washed 3 times for 10 minutes in PBST, and incubated in blocking solution containing a donkey anti-chicken Alexa® 647 secondary antibody (Millipore, AP194SA6) for 2 hours at room temperature. Slices were washed with PBST 3 times for 10 minutes each, and finally stained for (4',6-diamidino-2-phenylindole) DAPI (1:1000) for 10 minutes and mounted onto glass slides. For the TH staining in the dual-color mouse, normal goat serum (NGS) was used instead of NDS, and no Triton®-X (polyethylene glycol p-(1,1,3,3-tetramethylbutyl)-phenyl ether) was added at any step. The same TH antibody was used with a goat anti-chicken Alexa®647 secondary antibody (Life Technologies, A21449, 1:500). No DAPI or primary antibodies against GCaMP6 or R-CaMP2 were used.

Example 2: System Design, Alignment, and Calibration Considerations for FIP Microscopy A basic microscope consisting of the objective lens and tube lens was constructed, where the sCMOS camera was focused on the fiber(s) mounted at the working distance of the objective (FIG. 1A). Here, the objective and tube lens were chosen to set the magnification of the fibers onto the sensor, which determines the number of pixels on the camera that a given fiber tip is imaged onto. Note that the objective field of view and NA is larger than the fiber size and NA. Given that the dominant noise source of the sCMOS camera is read noise, the image may be sampled with as few sCMOS pixels as possible without saturating any pixels. However, for low light levels, photon shot noise may dominate the read noise, in which case more excitation light power may be used to generate more emission photons, and more camera pixels may be used to sample the emission without saturating. The excitation light sources were then added using dichroic mirrors between the tube lens and the objective. Similar to the tube lens of the camera, the focal length of the collimators for each excitation light source was chosen to set the magnification and NA to correctly fill the fiber(s). To align the relayed image of each excitation light source onto the previously aligned fiber(s), the position of the fiber(s) was annotated in the camera view and the excitation light sources were each positioned to be centered over the fiber(s) (FIG. 3A). Finally, in the dual-color imaging experiments with the image splitter, the image splitter was simply attached to the camera and positioned until the now two images of the fiber(s) were in focus again. The synchronization of the light sources to the sCMOS camera was tested using a fluorescent slide. The duty cycle and precise on-time of each light source was adjusted to accommodate the camera's rolling shutter and the off-slew-rate of each light source. This timing adjustment can be done once for each light source for each set of digital control waveforms.

Example 3: Simultaneous Calcium Measurements from Multiple Deep Brain Regions Using an sCMOS Camera To develop FIP microscopy, in vivo GCaMP6 recordings obtained with an sCMOS camera was compared to those obtained with a previously published design involving a photoreceiver and lock-in amplifier. The camera setup was modified to direct half the fluorescence emission from a single fiber onto a photoreceiver using a beamsplitter; excitation light was modulated for lock-in detection as previously described. The sCMOS camera measurement (even without lock-in detection) was found to be at least as sensitive as the measurement using a photoreceiver and lock-in amplifier (see Example 6; FIGS. 3A-3C).

The beamsplitter and photoreceiver was then removed to collect all fiber emissions onto the camera sensor. To control for non-$Ca^{2+}$ related fluorescence changes due to brain motion or fiber bending, camera frames corresponding to excitation of GCaMP6 and R-CaMP2 near their respective optical $Ca^{2+}$-dependent excitation wavelengths (470 nm or 560 nm), and also near the isosbestic wavelength (410 nm) were alternately acquired. Using simultaneous imaging paired with intracellular current injection-driven defined spiking patterns in cultured neurons, it was confirmed that GCaMP6 and R-CaMP2 increased fluorescence emission in response to action potentials when excited at 470 nm and 560 nm respectively, but exhibited virtually no change in emitted fluorescence when excited near 410 nm (see Example 7; FIGS. 4A-4F). Thus any changes observed while imaging either GCaMP6 or R-CaMP2 with 410 nm light were likely due to either motion-related artifacts or changes in intrinsic signals unrelated to neural activity. The ability to simultaneously record both the calcium-dependent signal and the 410 nm control signal allowed identification of artifacts that contaminate the signal in real-time, rather than in separate fluorophore-only cohorts. It was confirmed that large motion artifacts could be detected and corrected for in vivo when imaging GCaMP6 simultaneously with 470 nm and 410 nm light (FIG. 5).

Figure 5:
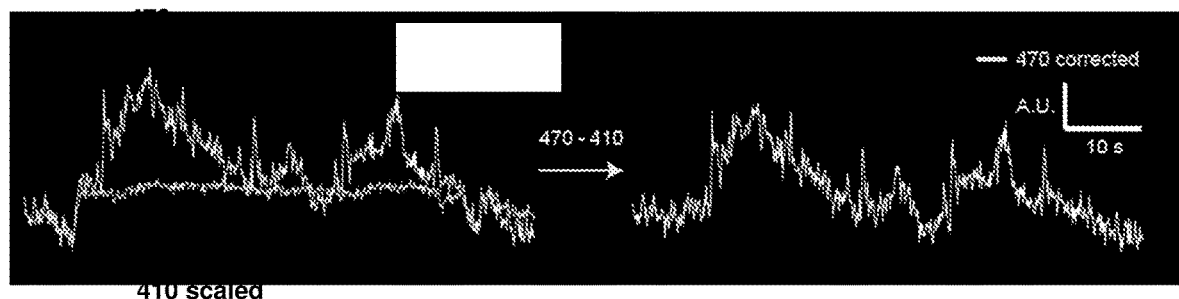
FIG. 5 is a collection of graphs showing an example of correcting motion-related artifacts present in the 410 nm isosbestic wavelength, according to embodiments of the present disclosure.

FIG. 5. Example of correcting motion-related artifacts present in the 410 nm isosbestic wavelength. Example of simultaneously recorded GCaMP6 signals using 470 nm and 410 nm excitation (left traces). The 410 nm signal has been scaled using least-squares regression to minimize the difference between the 410 and 470 nm signal. The scaled 410 nm trace from the 470 nm trace was then subtracted to generate the corrected 470 nm signal (right trace).

Figure 1C:
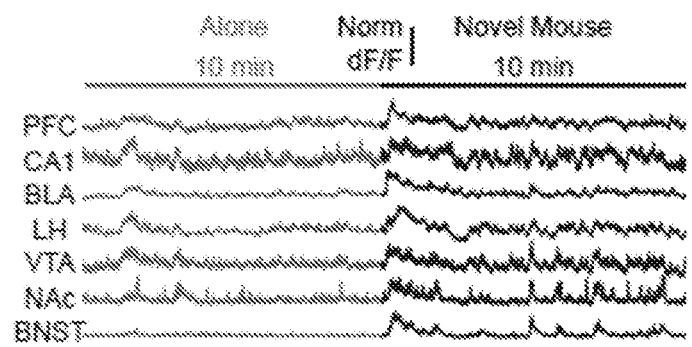
Figures 1D, 1E:
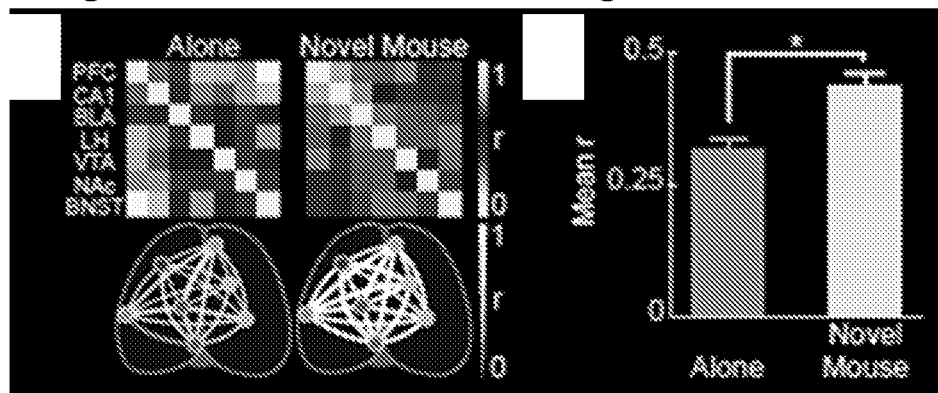

The FIP microscope's ability to simultaneously record GCaMP6 $Ca^{2+}$ signals from multiple fibers in vivo was then tested. A 7-fiber patchcord tightly bundled on one end and split into 7 separate branches on the other was used, to both deliver excitation light and collect emission light. Each of these 7 branches was coupled to a fiberoptic interface implanted into different widely-dispersed regions in an adult mouse; a single fast sCMOS camera then was interfaced to the output end, simultaneously measuring fluorescence emission from all 7 fibers by imaging the tightly bundled end of the patchcord (FIG. 1A). Using the FIP microscope, simultaneous and temporally registered GCaMP6f signals across the brain in a freely moving mouse was then measured. The targeted areas were 1) bed nucleus of the stria terminalis (BNST), 2) nucleus accumbens (NAc), 3) ventral tegmental area (VTA), 4) lateral hypothalamus (LH), 5) basolateral amygdala (BLA), 6) hippocampal region CA1, and 7) prefrontal cortex (PFC) in DAT::Cre driver mice. A Cre-dependent GCaMP6f virus was injected into the VTA to preferentially label dopamine (DA) neurons, while a CaMKIIα-GCaMP6f virus was injected in the other regions. GCaMP6f fluorescence signals that were present with 470 nm excitation, but absent with isosbestic-range 410 nm excitation (FIG. 1B) where only small, non-$Ca^{2+}$ dependent changes (likely due to motion or system-related artifacts; for example in CA1) were observed. The 470 nm signals were then normalized by the 410 nm control traces, and neural activity was measured across all 7 brain regions during naturalistic and freely-moving social interactions. Spontaneous activity could be robustly observed in all 7 brain regions, in addition to a time-locked increase in fluorescence activity upon the introduction of a novel mouse (FIG. 1C). Joint-statistical relationship among the brain regions was calculated using Pearson's correlation during periods when the mouse was alone versus when the mouse was socializing (FIG. 1D), and a global increase in pair-wise correlations across brain regions was observed when the mouse was socializing with a novel mouse (FIG. 1D). Shuffling analysis confirmed that this increase in pair-wise correlations was significantly greater than what would expected from simply increased activity in all of these regions (p<0.001, out of 1,000 shuffles).

FIG. 1. Simultaneous calcium measurements from multiple deep brain regions using an sCMOS camera. FIG. 1A) Schematic of microscope for simultaneous FIP calcium recordings. An example image of the bundled fiber faces is shown in the upper right inset. The lower left inset illustrates the time-division multiplexing scheme for simultaneously imaging GCaMP6 with 470 nm and 410 nm. FIG. 1B) Left: example image of a mouse implanted with 400 μm fibers in 7 different regions expressing GCaMP6f. Center: example calcium traces recorded from a freely moving mouse. Right: simultaneously recorded control traces. FIG. 1C) Example GCaMP6f fluorescence traces simultaneously acquired across the 7 different brain regions listed in FIG. 1B) when the mouse was alone versus when the mouse was placed with a novel mouse. The total imaging time was 10 min for each condition. Traces are plotted as dF/F normalized to each trace's maximum value. FIG. 1D) Top: Heat maps of the Pearson's correlation coefficients (r) calculated between all 7 brain regions for the example mouse shown in FIG. 1C). Bottom: Spatial representations of the Pearson's correlation coefficients between each brain region. Brain regions are plotted according to the anterior/posterior and medial/lateral coordinates where the fibers were implanted. The thickness of the lines connecting each brain region represents the magnitude of r. FIG. 1E) Summary of the mean r values between all brain regions calculated when the mouse was alone versus in the presence of a novel mouse. The mean r value significantly increased in the presence of a novel mouse compared to the baseline alone value (0.31±0.024 versus 0.43±0.024, p<0.001, n=84 pairs from 4 mice, Wilcoxon's rank-sum test). FIG. 1F) Schematic of surgery and recording setup for 4-fiber experiment. FIG. 1G) Example GCaMP6f fluorescence traces simultaneously acquired in each brain region in response to reward and tail shock. Solid lines denote calcium transients, dashed lines denote control signal (mean±S.E.M.; n=6 trials from one mouse). FIG. 1H) Summary of the mean responses to reward and shock in each brain region ($dF/F_{stimulus}-dF/F_{baseline}$). Asterisks indicate significant response (p<0.05, n=6 trials, Wilcoxon's signed-rank test).

Figure 1F:
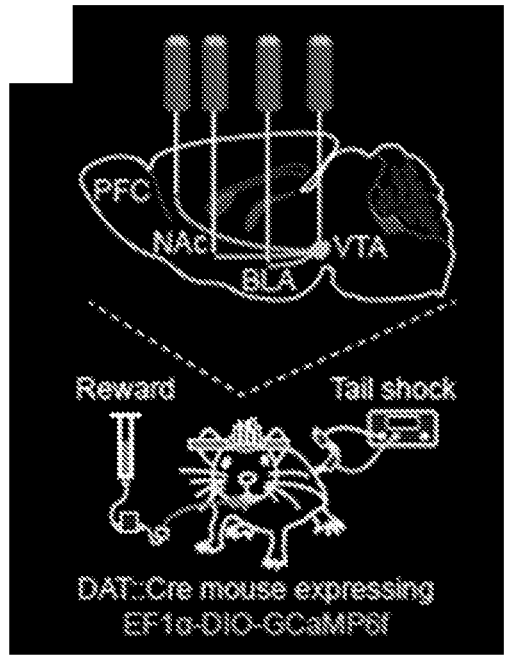
Figure 1G:
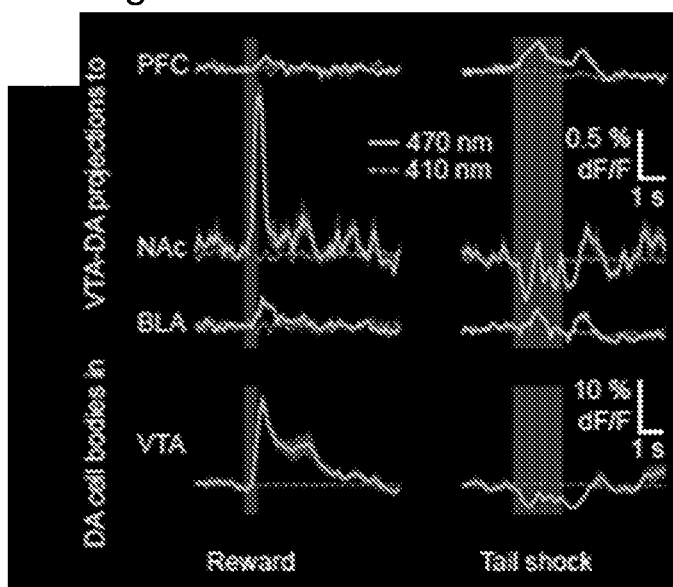

The sensitivity limits of the system were next tested by recording $Ca^{2+}$ signals not only from populations of cell bodies, but also from axonal projections to multiple independent regions. Here, a single injection of Cre-dependent GCaMP6f was made into the VTA of DAT::Cre driver mice. Optical fibers were then implanted in PFC, NAc, BLA, and VTA to simultaneously record from VTA-DA cell bodies or their axonal terminals in these downstream regions with the FIP microscope while administering controlled, time-locked water rewards or aversive tail shocks (FIG. 1F). It was found that the VTA-DA cell bodies exhibited increased activity during the rewarding stimulus, and decreased activity in response to the aversive tail shock, consistent with previous recordings from VTA-DA neurons. In contrast, the VTA-DA→BLA projection increased activity in response to both the reward and the tail shock. The VTA-DA→NAc projection showed a similar pattern compared with the VTA-DA cell bodies (increased activity in response to reward and decreased in response to tail shock), but activity in the VTA-DA→PFC projection exhibited yet a third pattern (increased response to tail shock but not reward; FIG. 1G, solid dark green). Supporting validity of the FIP approach, these results were consistent with previous studies that individually and separately tracked activity in different populations of VTA-DA neurons encoding rewarding or aversive stimuli depending on their projection target (though without the joint simultaneity of FIP during behavior).

Figure 1H:
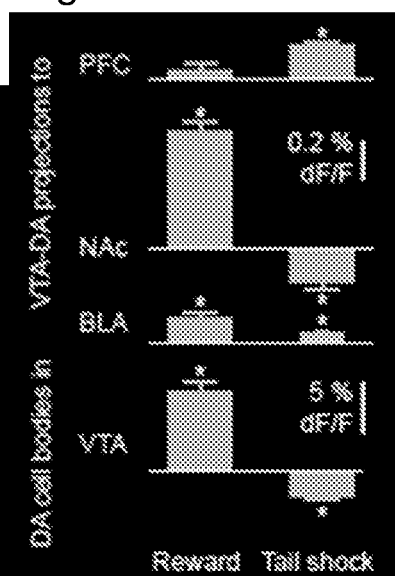
Figure 6A:
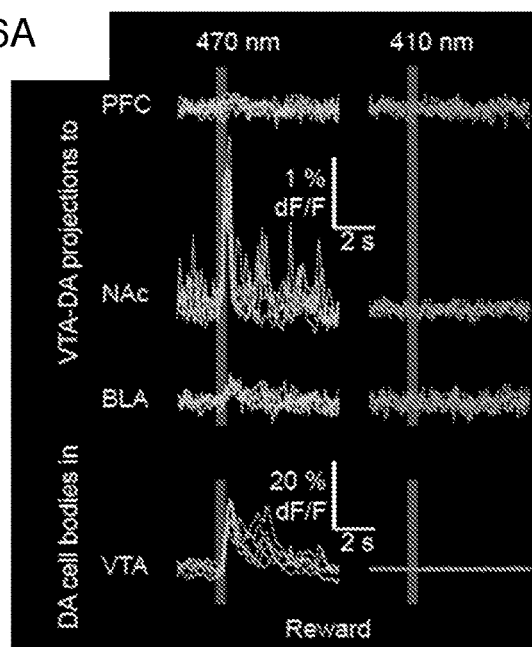
FIGS. 6A-6C are a collection of graphs showing example traces of simultaneous 4-fiber recordings of VTA-DA cell bodies and projections during reward and tail shock, according to embodiments of the present disclosure.
Figure 6B:
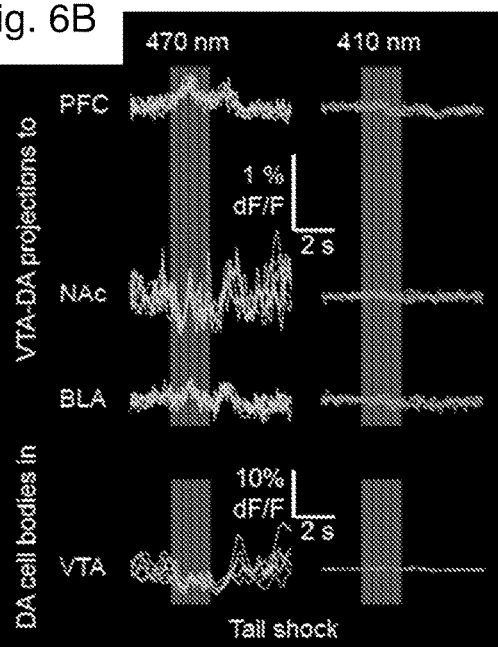
Figure 6C:
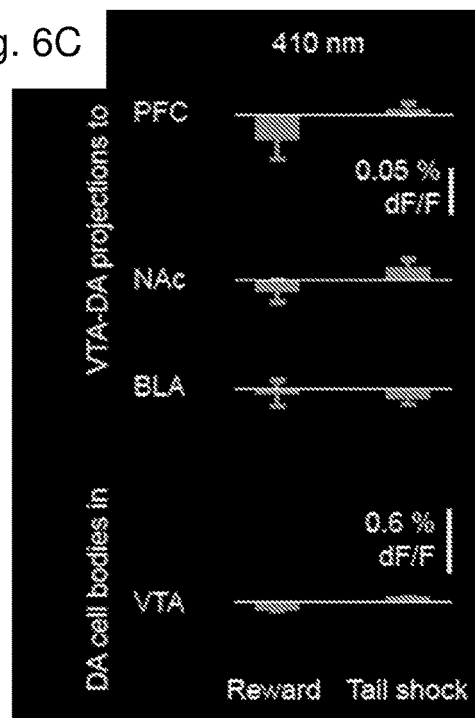

Response sizes are summarized in FIG. 1H; as expected, there was little change in the GCaMP6f control signal measured at 410 nm (FIG. 1G, dashed light green). Raw GCaMP6f fluorescence traces are shown in FIGS. 6A-6B, and mean changes for the control signals are plotted in FIG. 6C (all insignificant). Table 1 summarizes the significant GCaMP6f responses recorded during reward and shock (with insignificant changes in GCaMP6f isosbestic control fluorescence). Histology confirming locations of fibers and expression of GCaMP6f in cell bodies and terminals is provided in FIGS. 7A-7D. Note that very sparse GCaMP6f fibers localized to the amygdala regions surrounding the BLA was observed, and these fibers could also be contributing to the signal.

TABLE 1

Number of mice showing significant GCaMP responses to reward or tail shock with 470 nm light for 4-fiber experiment.

| Brain Region | Reward | Tail Shock |
| --- | --- | --- |
| VTA-DA in PFC | N.S. | 3 mice |
| VTA-DA in NAc | 7 mice | 4 mice |
| VTA-DA in BLA | 3 mice | 2 mice |
| VTA-DA | 6 mice | 5 mice | p < 0.05, Wilcoxon's signed-rank test, n = 6-12 trials for each mouse.
p > 0.05 for control GCaMP6 responses with 410 nm light for all mice.

Example 4: Dual Color Imaging of Different Populations

Figure 9A:
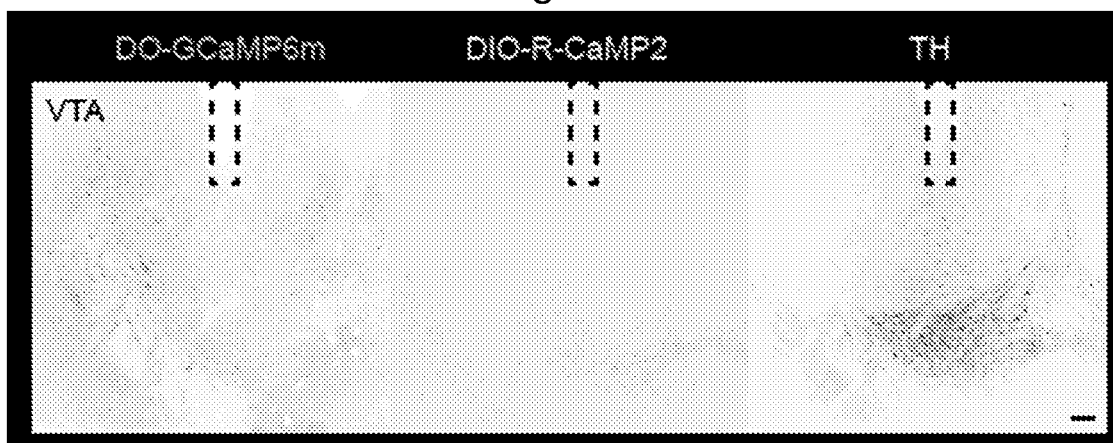
FIGS. 9A and 9B are a collection of images showing confirmation of fiber location and virus specificity for dual-color imaging, according to embodiments of the present disclosure.
Figure 9B:
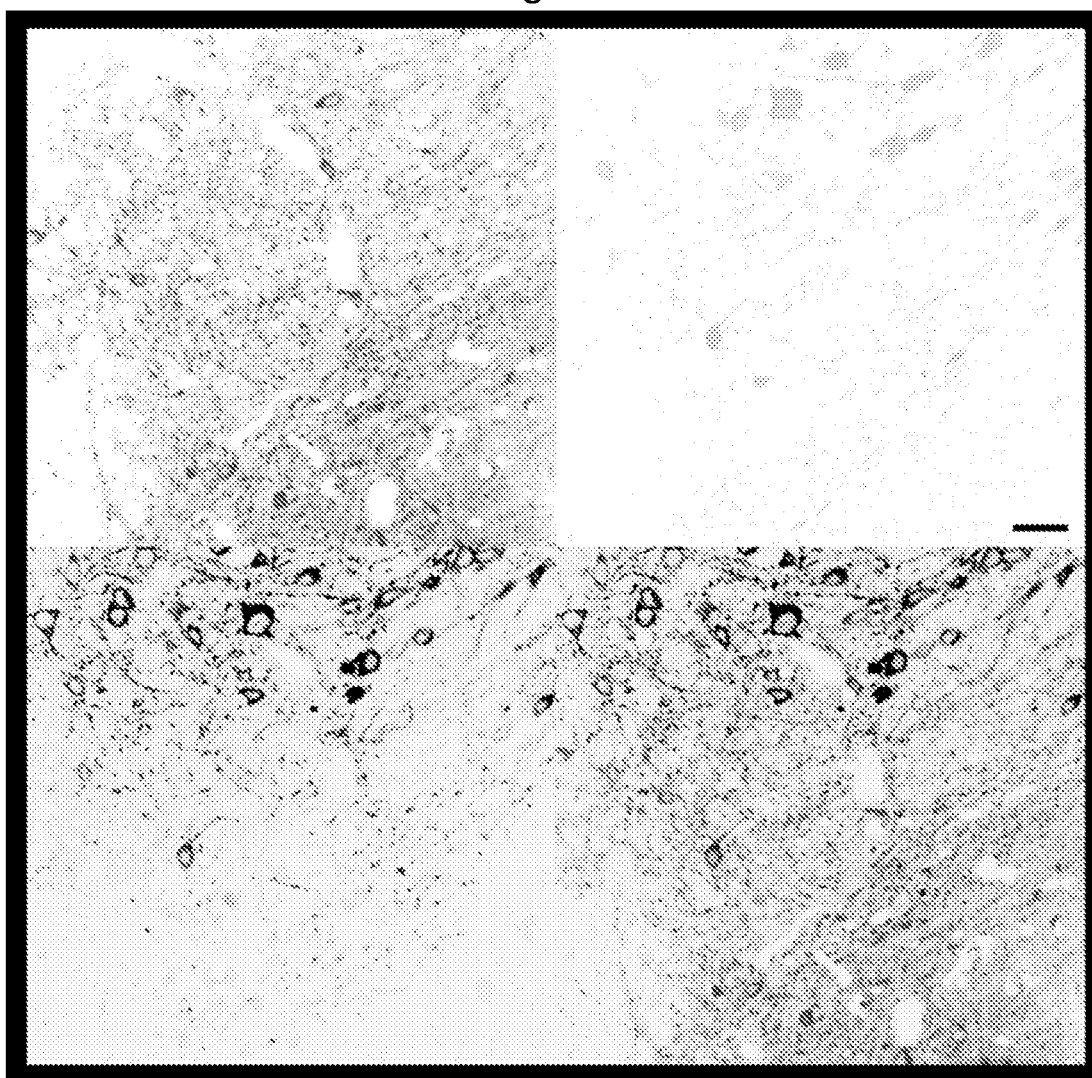

The FIP microscope was readily adaptable for dual-color imaging of different populations using two different $Ca^{2+}$ sensors (in this case GCaMP6 and R-CaMP2). By placing an image splitter in front of the camera sensor and adding an additional 560 nm excitation source (FIG. 8A), it was possible to simultaneously collect GCaMP6 and R-CaMP2 fluorescence emission through the same fiber. VTA-DA expressing and VTA-non-DA expressing neurons in DAT:: Cre mice was labeled using a Cre-activated (DIO) AAV:R-CaMP2 virus and a Cre-deactivated (DO) GCaMP6m virus, respectively (FIG. 2A). This viral strategy resulted in labeling of largely non-overlapping populations of R-CaMP2 and GCaMP6m neurons in the VTA (FIG. 2B), and expression of DIO:R-CaMP2 was found to co-localize with the tyrosine hydroxylase (TH) stain for DA-expressing neurons (FIGS. 9A-9B). While monitoring these neural populations with the FIP microscope, reward or tail shock stimuli was administered. Consistent with the earlier 4-fiber recordings, it was found that activity in VTA-DA neurons significantly increased in response to reward and significantly decreased in response to tail shock (FIG. 2C-2D). It was found that the VTA non-DA neurons exhibited a significant increase in fluorescence in response to both reward and tail shock (FIG. 2C-2D), consistent with previous electrical recordings. There was no significant change in R-CaMP2 or GCaMP6m control fluorescence in response to 410 nm excitation during reward or tail shock (FIG. 2C).

FIGS. 2A-2D. Dual-color imaging of different populations. FIG. 2A) Schematic of dual-color imaging surgery preparation. FIG. 2B) Non-overlapping populations of VTA-DA neurons and VTA-non-DA labeled with R-CaMP2 and GCaMP6m, respectively. Scale bar indicates 25 μm. FIG. 2C) VTA-DA and VTA-non-DA fluorescence traces in response to reward and tail shock (red, VTA-DA neurons; green, VTA-non-DA neurons; solid curves, calcium transients; dashed curves, control signals). FIG. 2D) Summary of the mean responses to reward and shock (dF/F$_{stimulus}$–dF/F$_{baseline}$). VTA-DA neural activity increased in response to reward (5.39±0.32% dF/F) and decreased in response to shock (−1.18±0.45% dF/F), while VTA-non-DA neural activity increased in response to both reward (3.26±0.14% dF/F) and shock (2.08±0.14% dF/F). Asterisks indicate p<0.05, n=10 trials, Wilcoxon's signed-rank test.

FIG. 8A. Microscope configuration used for dual-color imaging experiments. a) Schematic of setup for dual-color imaging. An image splitter was placed before the camera sensor, and an additional 560 nm LED was used to image R-CaMP2. The lower left inset represents the time-division multiplexing strategy used to simultaneously image GCaMP6 and R-CaMP2 at both their calcium sensitive and insensitive wavelengths.

Figures 7A, 7B:
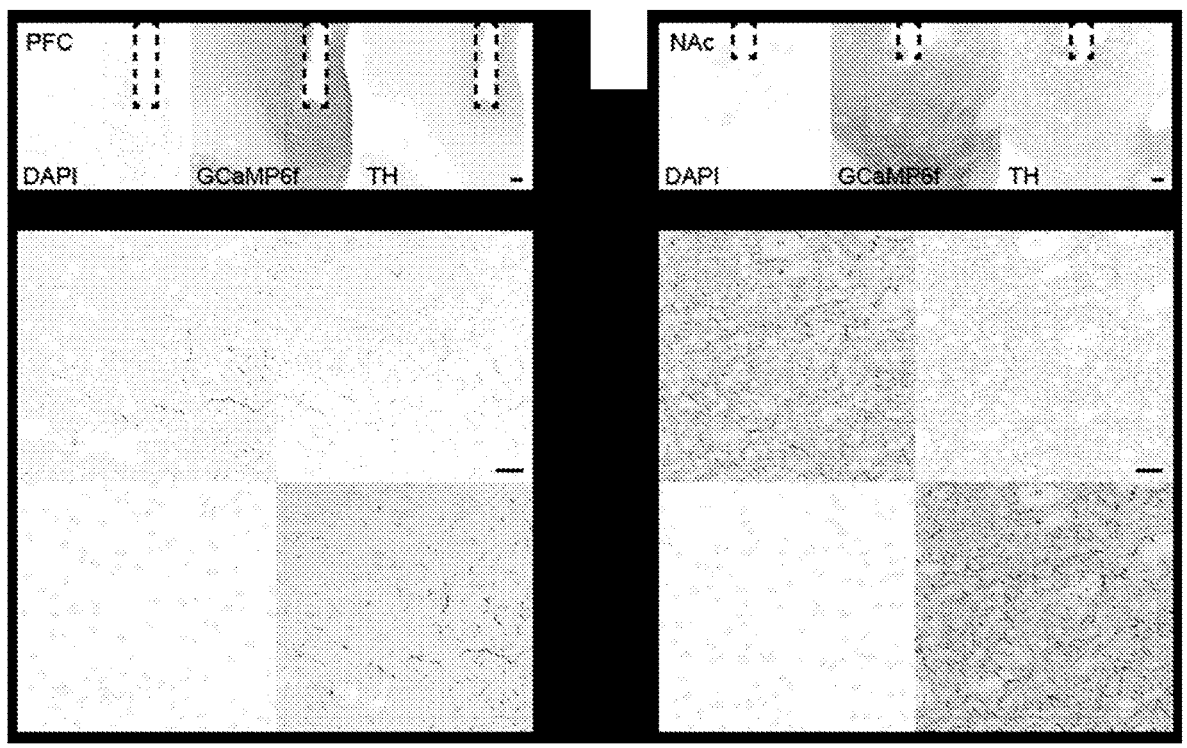
FIGS. 7A-7D are a collection of images showing confirmation of fiber location and virus expression for 4-fiber surgeries, according to embodiments of the present disclosure.
Figures 7C, 7D:
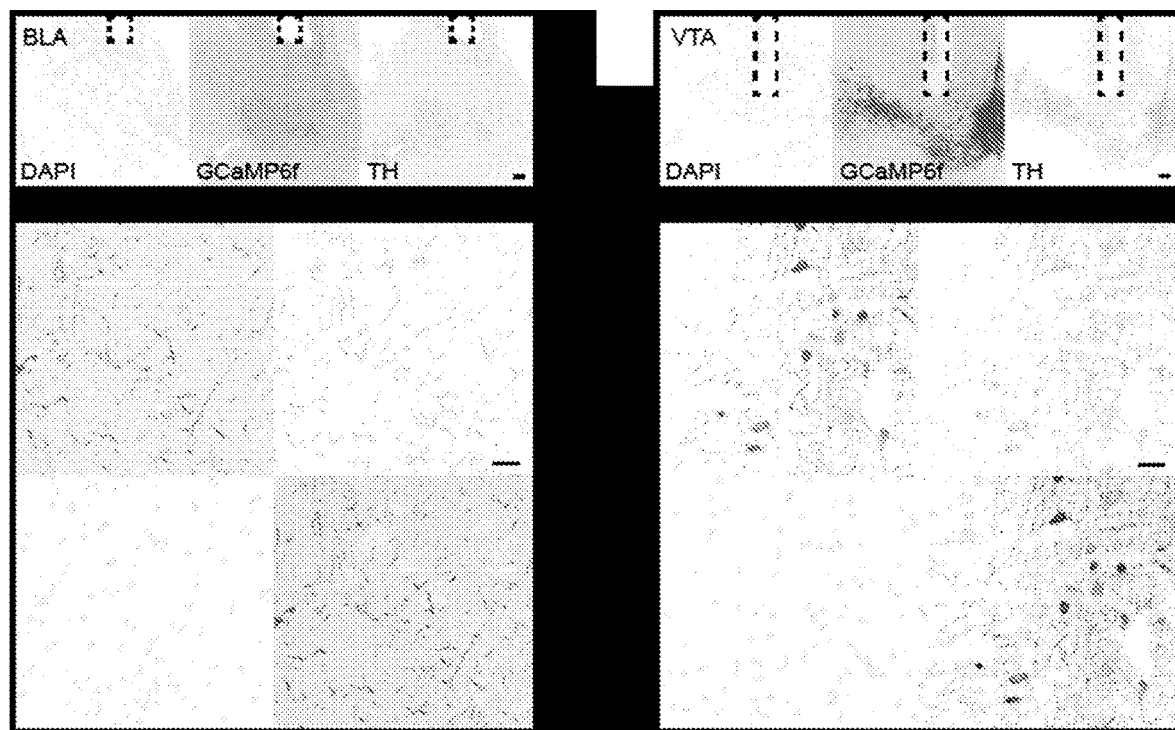

FIGS. 7A-7B. Confirmation of fiber location and virus specificity for dual-color imaging. FIG. 7A) 10× magnification images of a slice containing VTA. GCaMP6m fluorescence in VTA-non-DA neurons is shown in green, R-CaMP2 fluorescence in VTA-DA neurons is shown in red, and a TH stain is shown in white. Dashed white rectangle indicates fiber location. Scale bar indicates 100 μm. FIG. 7B) 63× magnification images of VTA slice with same staining. Bottom right image is a merge of all three channels. Scale bar indicates 25 μm.

Example 5: Dual Color Imaging of Different Populations

Figure 2E:
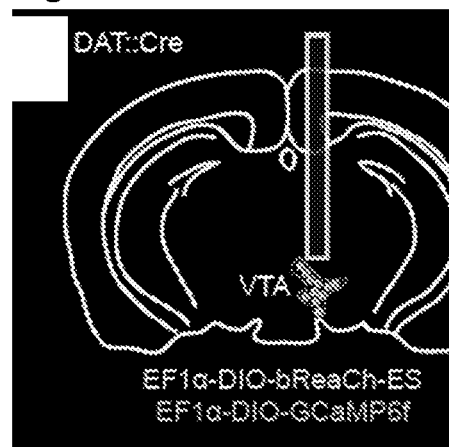
Figure 2F:
Figure 2G:
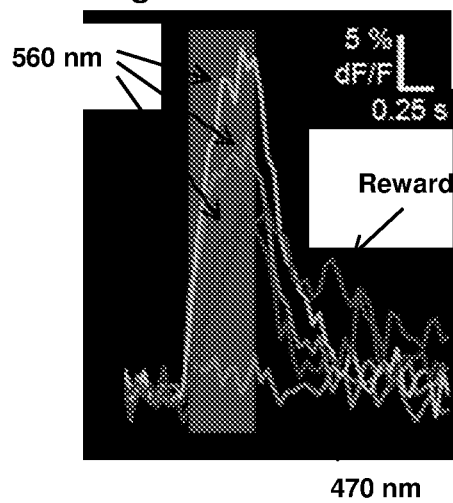
Figure 2H:
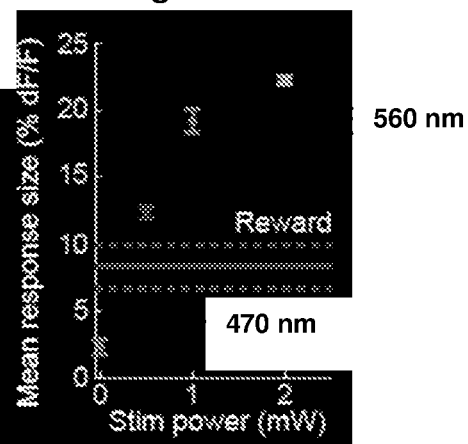
Figure 4A:
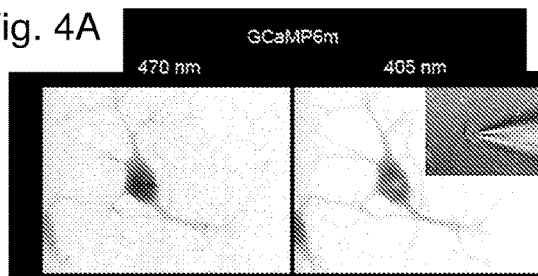
FIGS. 4A-4F are a collection of images and graphs showing GECI fluorescence emission to calcium-dependent excitation wavelengths and to a calcium-independent isosbestic wavelength, according to embodiments of the present disclosure.
Figure 4B:
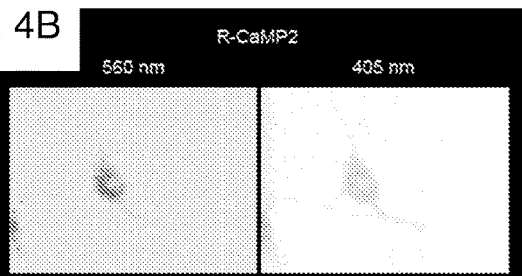
Figure 4C:
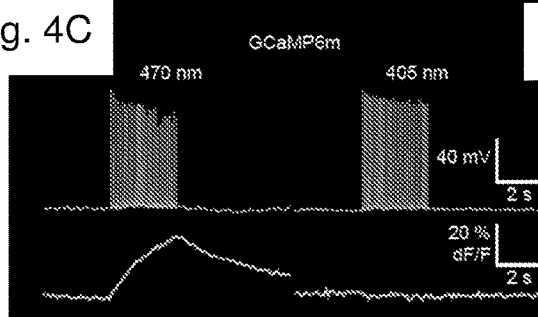
Figure 4D:
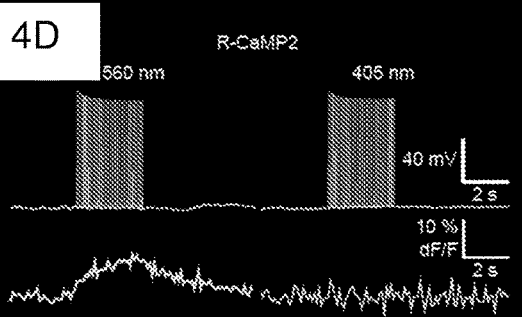
Figure 4E:
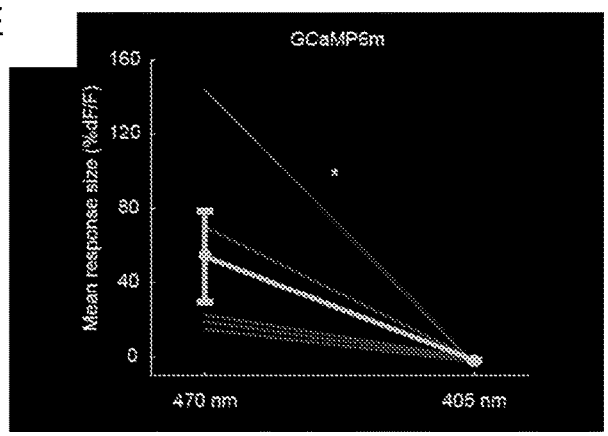
Figure 4F:
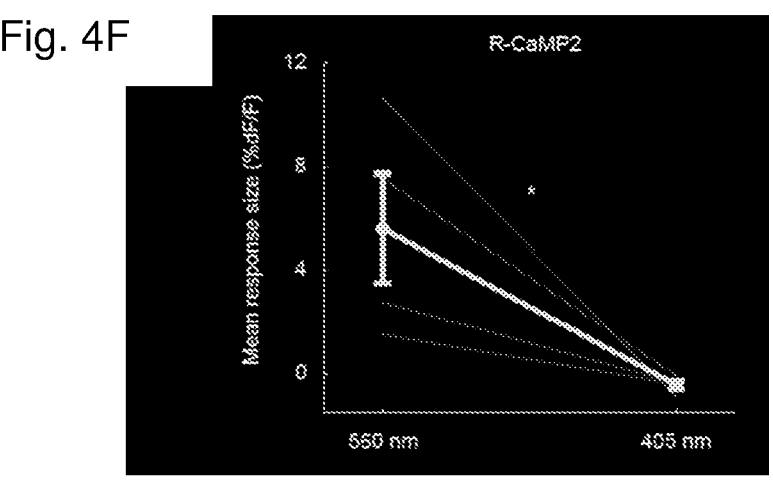

The FIP microscope readily allowed tuning optogenetic stimulation to match activity levels that naturally occurred with behaviorally-relevant timing within the very same targeted neural population at the same location in the same experimental subject (FIGS. 2E-2H). Simultaneous recording and perturbation of neural activity was performed using GCaMP6 and a potent and fast red-shifted channelrhodopsin, bReaCh-ES (Methods, Example 8, and FIGS. 10A-10F). The 560 nm LED used to image R-CaMP2 was replaced with a 594 nm laser for bReaCh-ES (FIG. 8B), and DIO-bReaCh-ES-TS-mCherry was virally expressed along with DIO-GCaMP6f in the VTA of DAT::Cre mice in order to both image and perturb VTA-DA neurons (FIG. 2E), anticipating that the high light sensitivity of the FIP microscope could allow recording of GCaMP6f signals under very low imaging power that would minimize cross-stimulation of bReaCh-ES by GCaMP6f excitation light (Example 9). GCaMP6f fluorescence responses to interleaved pulses of 470 nm stimulation light identical to the 470 nm pulses used to image GCaMP6 was measured; GCaMP6f responses to 594 nm pulses, and to a naturalistic water reward were also measured (FIG. 2F). It was found that using 5 μW of power (measured at the face of the 400 μm Ø patchcord, for 470 nm imaging and stimulation) resulted in minimal changes in GCaMP6f fluorescence (FIG. 2G), while higher light powers of 470 nm light elicited much larger GCaMP6f transients as a result of opsin cross-stimulation (FIGS. 11A-11B). Using only 5 μW of 470 nm imaging light power was still sufficient to observe VTA-DA responses to 594 nm bReaCh-ES stimulation that scaled with light intensity (FIG. 2G), and could be tuned to match amplitude of VTA-DA responses to water reward in the very same animal (FIG. 2G). A summary of the mean GCaMP6f response size to various stimulation wavelengths and powers is shown in FIG. 2H. A control DAT::Cre mouse expressing DIO-GCaMP6f and DIO-mCherry exhibited no significant changes in GCaMP6f fluorescence in response to interleaved 470 nm or 594 nm stimulation light, but did exhibit GCaMP6f transients as expected during interaction with a novel mouse, known to elicit VTA-DA activity (FIGS. 11C-11D).

FIGS. 2E-2H. Simultaneous recording and perturbation of neural activity. FIG. 2E) Schematic of combined imaging and optogenetics surgery preparation. FIG. 2F) Schematic of imaging paradigm. For experiments, 10 stimulation pulses were used. FIG. 2G) Example GCaMP6f fluorescence traces in response to bReaCh-ES cross-stimulation with with 5 μW of 470 nm light (light blue), bReaCh-ES stimulation with 594 nm light (light to dark orange denote 0.5 mW, 1 mW, and 2 mW of power), or a water reward (cyan). FIG. 2H) Summary of the mean responses to bReaCh-ES stimulation or reward (dF/F$_{stimulus}$–dF/F$_{baseline}$). The mean VTA-DA neuron response size to 5 μW 470 nm stimulation (n=6 trials, 2.27±0.57% dF/F) was significantly smaller than the response size to the reward (n=4 trials, 8.27±1.63% dF/F, p<0.05, Wilcoxon's rank-sum test).

FIG. 8B. Microscope configurations used for simultaneous imaging and perturbation experiments. b) Schematic of setup for simultaneous imaging and perturbation experiments. The 560 nm LED was replaced with a 594 nm laser for optogenetic stimulation. For cross-stimulation measurements, the 594 nm laser was replaced with an additional 470 nm LED, and the dichroic combining the 470 nm and 594 nm light was replaced with a 50:50 beamsplitter.

Figure 10A:
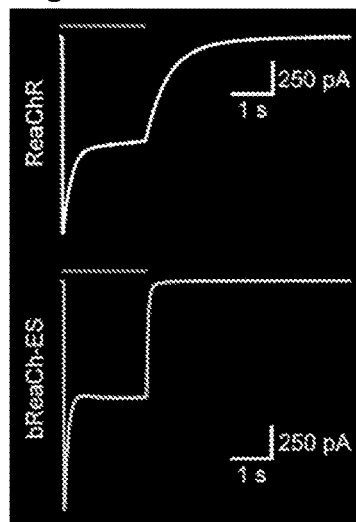
FIGS. 10A-10F are a collection of graphs showing the characterization of a bReaCh-ES opsin, according to embodiments of the present disclosure.
Figure 10B:
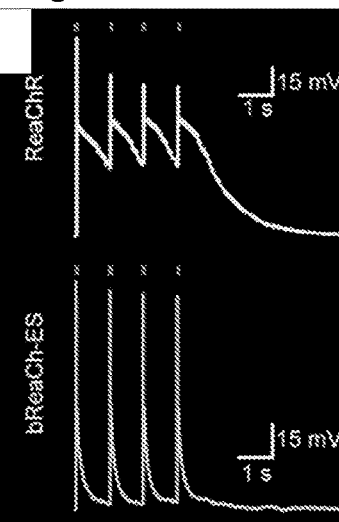
Figure 10C:
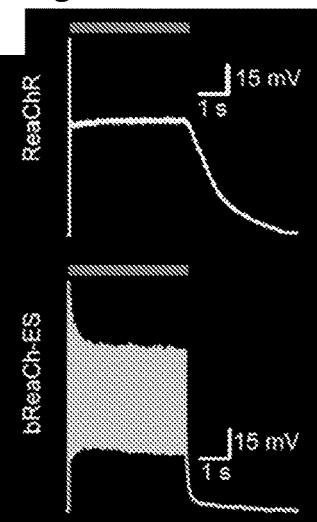
Figure 10D:
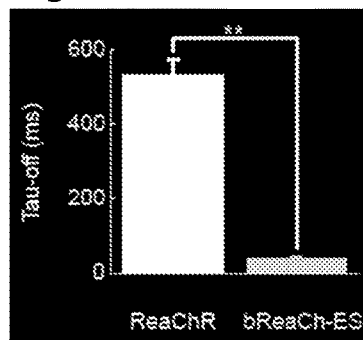
Figure 10E:
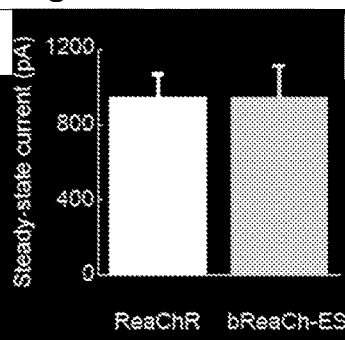
Figure 10F:
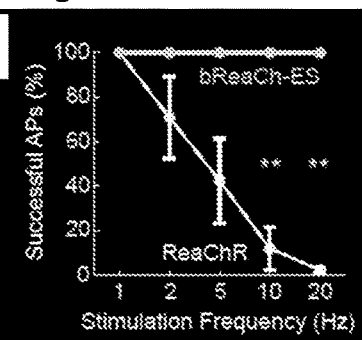
Figures 11A, 11B:
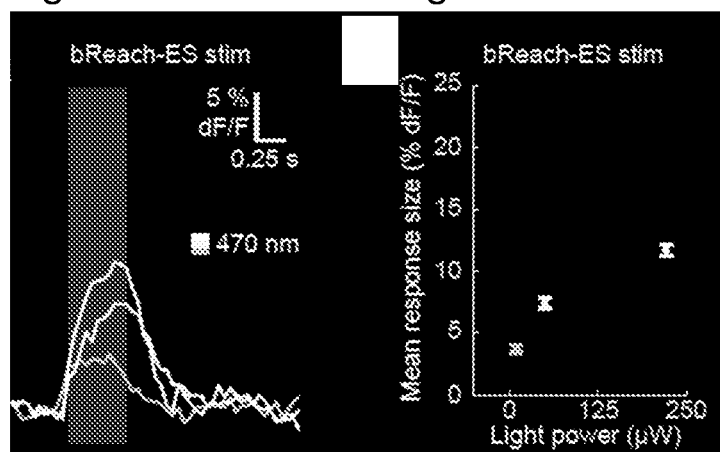
FIGS. 11A-11D are a collection of graphs showing control experimental results for simultaneous imaging and perturbation experiment, according to embodiments of the present disclosure.
Figures 11C, 11D:
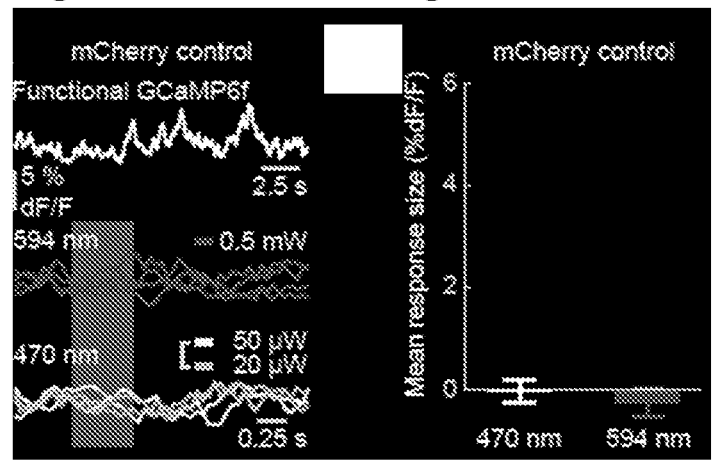

FIGS. 10A-10F. Characterization of novel bReaCh-ES opsin. FIG. 10A) Example of internal current elicited by a 4 s pulse of 590 nm light (orange) for neurons expressing ReaChR or bReaCh-ES. FIG. 10B) Voltage recordings showing 4 APs in response to 4, 5 ms pulses of 590 nm (orange) light delivered at 1 Hz to neurons expressing ReaChR or bReaCh-ES. FIG. 10C) Voltage recordings showing APs in response to 80, 5 ms pulses of 590 nm light (orange) delivered at 20 Hz to neurons expressing ReaChR or bReaCh-ES. FIG. 10D) Average tau-off kinetics measured for ReaChR and bReaCh-ES. The mean tau-off for bReaCh-ES was significantly smaller than that of ReaChR (ReaChR: 531.83±40.29 ms; bReaCh-ES: 39.33±3.69 ms; p<0.005, n=6 cells, Wilcoxon's rank-sum test). FIG. 10E) Steady-state current measured for ReaChR and bReaCh-ES. There was no significant difference between steady-state current between ReaChR and bReaCh-ES (ReaChR: 946.00±121.97 pA; bReaCh-ES: 941.17±169.30 pA; p>0.05, n=6 cells, Wilcoxon's rank-sum test). FIG. 10F) Percentage of APs successfully elicited by a 4 s train of 590 nm light pulses (5 ms pulse width) delivered at 1, 2, 5, 10, and 20 Hz to neurons expressing ReaChR or bReaCh-ES. At 10 and 20 Hz, bReaCh-ES stimulation elicits a significantly higher percentage of successful APs than ReaChR (ReaChR: 12.08±9.58% at 10 Hz, 2.29±1.04% at 20 Hz; bReaCh-ES: 100±0% at 10 and 20 Hz; p<0.005, n=6 cells, Wilcoxon's rank-sum test).

FIGS. 11A-11D. Control for simultaneous imaging and perturbation experiment. FIG. 11A) Example GCaMP6f fluorescence traces in response to bReaCh-ES cross-stimulation with 470 nm light (light to dark blue represents 10 μW, 50 μW, and 220 μW of power). FIG. 11B) Summary of the mean GCaMP6f responses to bReaCh-ES cross-stimulation with 470 nm light (dF/F$_{stimulus}$–dF/F$_{baseline}$). FIG. 11C) Top: Example GCaMP6f fluorescence trace taken from a control mouse expressing mCherry instead of bReaCh-ES to demonstrate that there is functional GCaMP6f present. Bottom:

GCaMP6f fluorescence traces in response to 0.5 mW 594 nm stimulation pulses (orange), and to 20 or 50 µW 470 nm stimulation pulses (blue). FIG. 11D) Summary of the mean GCaMP6f responses to light ($dF/F_{stimulus} - dF/F_{baseline}$) in the mCherry control mouse. There were no significant changes in GCaMP6f fluorescence with 470 nm or 594 nm stimulation light ($p > 0.05$ Wilcoxon's signed-rank test).

Example 6: Simultaneous Camera and Photoreceiver Lockin-In Measurements

To get a conservative estimate of how the sensitivity of the sCMOS camera without lock-in detection compares with the previous state-of-the-art technique employing lock-in detection, an experiment was conducted where the same calcium-dependent fluorescence was recorded simultaneously with both techniques. To accomplish this, the excitation light source was modulated at 448 Hz and synchronized with the lock-in amplifier configured with a −3 dB filter with 24 dB slope at 16 Hz (corresponding to 10 ms time constant), consistent with the imaging parameters described previously. Modulating the excitation source at 448 Hz minimized both the presence of 60 Hz electrical noise in the photoreceiver, and beating artifacts from the modulated light in the camera. The emission from the fiber was equally split with a beamsplitter between the photoreceiver connected to the lock-in amplifier and the sCMOS camera. In order to match the 16 Hz bandwidth detection of the lock-in amplifier, the camera was set to acquire frames at 32 Hz (to Nyquist sample the desired 16 Hz bandwidth). Importantly, while the signal from the lock-in amplifier benefits from the demodulation of the 448 Hz carrier signal, no attempt was made to demodulate the signal recorded by the sCMOS camera though it would be possible if sampling was done at a higher frame rate. Hence, the signal from the sCMOS camera was a conservative estimate of what would be measured with constant excitation without any modulation or lock-in detection.

Example 7: Isosbestic Excitation Wavelength of GCaMP6 and R-CaMP2

The published absorption spectrum of GCaMP3 and R-CaMP2 suggested that an isosbestic point between 405-420 nm exists where the absolute GCaMP or R-CaMP emission is independent of calcium concentration. Previous studies using the AM esterase dye Fura-2, for example, have used fluorescence emission collected with the isosbestic excitation wavelength to measure calcium-independent changes in fluorescence of the indicator. Thus by simultaneously measuring the GCaMP6 and R-CaMP2 fluorescence using the ~isosbestic 410 nm wavelength, a reference signal could be recorded that reported non-calcium related fluorescence changes that could be contributing to the measured calcium signals. While both the calcium signals and control signals were presented in the Examples, one could normalize the calcium signal by its corresponding control signal to estimate neural activity-related changes in fluorescence.

Example 8: Generation of bReaCh-ES Construct

Recently a red-shifted excitatory opsin, ReaChR, was published that exhibits large photocurrents capable of transcranial optogenetic stimulation. However, photocurrents expressing ReaChR were accompanied by a long tau-off, which hindered the ability to elicit APs at frequencies higher than 1 Hz. A mutation to the existing ReaChR was introduced to generate bReaCh-ES, which exhibited the same large photocurrents as ReaChR, but had a significantly short tau-off that allows APs to be driven 100% reliably at up to 20 Hz (FIGS. 10A-10F).

Example 9: Procedure for Estimating Cross-Stimulation of bReaCh-ES

It is well known that the excitation spectrum of GCaMP6 and the excitation spectrum of red-shifted indicators such as C1V1 exhibit significant overlap. As a result, a given choice of excitation wavelength for GCaMP6 may result in unwanted bReaCh-ES cross-stimulation to some extent, and this effect may be quantified. To characterize the amount of cross-stimulation of bReaCh-ES produced by the GCaMP6 excitation light, additional pulses of 470 nm stimulation light at 20 Hz (10 pulses with 12.5 ms pulse width) were applied while imaging GCaMP6 with 470 nm light (20 Hz, 12.5 ms pulse width). As expected, with higher powers of the 470 nm blue excitation, larger changes in GCaMP6 fluorescence were observed likely due to cross-stimulation of bReaCh-ES. As a comparison, the change in GCaMP6 fluorescence was also measured to interleaved pulse trains of 594 nm light at 20 Hz (10 pulses with 12.5 ms pulse width) intended to stimulate bReaCh-ES, and to a water reward. This protocol for characterizing the amount of cross-stimulation was a more explicit measure than those used in previous papers.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method comprising:
   a) illuminating a region of a target tissue with a light stimulus comprising light pulses of a plurality of wavelengths, wherein:
   the region is labeled with one or more cellular activity-dependent fluorescent moieties; and
   the light pulses comprise: i) a first set of light pulses at a first wavelength; and ii) a second set of light pulses at one or more wavelengths, wherein each of the one or more wavelengths are different from the first wavelength and are at an excitation wavelength of the one or more cellular activity-dependent fluorescent moieties, and wherein each light pulse of the first set are interleaved among light pulses of the second set,
   thereby generating fluorescence from the region,
   wherein a multimode optical fiber is configured to direct the light stimulus to, and collect the fluorescence from, the region;
   b) recording by an image detector, onto independent frames for each light pulse, an image of a terminal cross-section of the multimode optical fiber from the region, wherein a cross-sectional average of the fluorescence generated in response to the second set of light pulses is representative of an aggregate cellular activity of the region; and
   c) analyzing the recorded image, to generate an output comprising a measure of the aggregate cellular activity in the region, wherein the analyzing comprises:
      1) demarcating the cross-section of the multimode optical fiber from the region in the recorded image;
      2) calculating an average of the fluorescence across the cross-section; and
      3) calculating a normalized change in the fluorescence over a baseline fluorescence for the cross-section of the multimode optical fiber in the recorded image, wherein the baseline fluorescence is a median of the average fluorescence within the cross-section of the multimode optical fiber across a plurality of recorded images.

2. The method according to claim 1, wherein the multimode optical fiber has a diameter in the range of 100 to 1000 µm and the image detector comprises an image sensor.

3. The method according to claim 1, wherein the region comprises one or more collections of a plurality of neurons, or a subcellular portion thereof labeled with one or more cellular activity-dependent fluorescent moieties and the one or more collections comprise one or more functionally-defined collections of a plurality of neurons.

4. The method according to claim 3, wherein the region comprises:
   a first collection of the plurality of neurons, each neuron of the first collection comprising a first cellular activity-dependent fluorescent moiety; and
   a second collection of the plurality of neurons, each neuron of the second collection comprising a second cellular activity-dependent fluorescent moiety,
   and wherein
   the second set of light pulses comprise:
   a third set of light pulses at a second wavelength, different from the first wavelength, wherein the second wavelength is at an excitation wavelength of the first cellular activity-dependent fluorescent moiety; and
   a fourth set of light pulses at a third wavelength, different from the first and second wavelengths, wherein the third wavelength is at an excitation wavelength of the second cellular activity-dependent fluorescent moiety,
   and wherein the recording comprises recording a first image and a second image of the terminal cross-section of the multimode optical fiber from the region,
   wherein a cross-sectional average of the fluorescence generated in response to the third set of light pulses in the first image is representative of an aggregate neural activity of the first collection of a plurality of neurons, and a cross-sectional average of the fluorescence generated in response to the fourth set of light pulses in the second image is representative of an aggregate neural activity of the second collection of a plurality of neurons.

5. The method according to claim 1, wherein the first wavelength is at an isosbestic point of at least one of the one or more cellular activity-dependent fluorescent moieties.

6. The method according to claim 1, wherein the analyzing comprises 4) subtracting an average of the cellular activity-independent fluorescence across a cross-section from an average of the cellular activity-dependent fluorescence across the cross-section, to obtain a motion-corrected measure of the aggregate cellular activity.

7. The method according to claim 1, wherein the one or more cellular activity-dependent fluorescent moieties comprise a calcium- and/or a voltage-sensitive indicator dye.

8. The method according to claim 1, wherein the image detector is a charge-coupled device (CCD) or a complementary metal oxide semiconductor (CMOS) camera.

9. The method according to claim 1, wherein the fluorescence emitted from the region is split using an image splitter to form and record a separate image for the fluorescence emitted by each of the one or more cellular activity-dependent fluorescent moieties.

10. The method according to claim 1, wherein the plurality of wavelengths comprise wavelengths of 440 nm to 620 nm.

11. The method according to claim 2, wherein the multimode optical fiber has a diameter of 400 µm.

12. The method according to claim 5, wherein the isosbestic point is between 405 nm to 420 nm.

13. The method according to claim 1, wherein light pulses in the first set are pulsed at a first frequency less than a second frequency at which light pulses of the second set are pulsed.

14. A system comprising:
   a) an illumination unit;
   b) an objective, wherein the objective is configured to receive light from the illumination unit and to focus the light at a working distance from the objective;
   c) a plurality of light conduits, each light conduit comprising one or more multimode optical fibers and defining a first end, a second end opposite the first, and a light conduit numerical aperture, wherein a terminus at the first end of each of the light conduits is at the working distance from the objective;
   a terminal cross-section corresponding to each of the one or more multimode optical fibers at the first end of each of the light conduits is in a field of view of the objective;
   and the light conduit numerical aperture is less than a numerical aperture of the objective;
   d) an image detector;
   e) a processor; and
   f) a computer-readable medium comprising instructions that, when executed by the processor, causes the system to:
   generate a light stimulus comprising i) a first set of light pulses at a first wavelength; and ii) a second set of light pulses at one or more wavelengths, each of the one or more wavelengths different from the first wavelength and wherein each light pulse of the first set are interleaved among light pulses of the second set, using the illumination unit, to illuminate a plurality of regions in a target tissue, each region at the second end of each of the plurality of light conduits, wherein the regions are labeled with one or more cellular activity-dependent fluorescent moieties, wherein the plurality of wavelengths comprises one or more wavelengths at an excitation wavelength of the one or more cellular activity-dependent fluorescent moieties, thereby generating fluorescence from each region;

collect the generated fluorescence from each region via the second end of the same light conduit of the plurality of light conduits used to illuminate the region, where the collected fluorescence is transmitted through each of the plurality of light conduits to each corresponding first end;

record an image including each of the one or more terminal cross-sections at the first ends of all of the plurality of light conduits using the image detector; and analyze the recorded image, to generate an output comprising a measure of aggregate cellular activity in the regions, wherein the analyzing comprises: 1) demarcating the terminal cross-sections in the recorded image; 2) calculating an average of the fluorescence across the terminal cross-sections; and 3) calculating a normalized change in the fluorescence over a baseline fluorescence the terminal cross-sections in the recorded image, wherein the baseline fluorescence is a median of the average fluorescence within the terminal cross-sections across a plurality of recorded images.

15. The system of claim 14, wherein the one or more multimode optical fibers have a diameter in the range of 100 to 1000 μm and the image detector comprises an image sensor.

16. The system of claim 14, wherein each of the light conduits comprises: an implantable fiber-optic element comprising an attachment element; and the one or more multimode optical fibers are configured to attach to the attachment element.

17. The system of claim 14, wherein the plurality of wavelengths comprises a wavelength at an isosbestic point of the one or more cellular activity-dependent fluorescent moieties.

18. The system of claim 14, wherein the plurality of wavelengths comprises a plurality of wavelengths at an excitation wavelength of a plurality of cellular activity-dependent fluorescent moieties.

19. The system of claim 14, wherein the plurality of wavelengths comprises one or more wavelengths at an activation wavelength of one or more light-activated polypeptides.

20. The system of claim 14, wherein the illumination unit is a light-emitting diode (LED) or an LED array or a laser.

21. The system of claim 14, wherein the image detector is a charge-coupled device (CCD) or a complementary metal oxide semiconductor (CMOS) camera.

22. The system of claim 14, further comprising an image splitter.

23. The system of claim 14, wherein the regions comprise one or more collections of a plurality of neurons, or a subcellular portion thereof, and the one or more collections of a plurality of neurons comprise one or more functionally-defined collections of a plurality of neurons; wherein the one or more cellular activity-dependent fluorescent moieties are one or more neural activity-dependent fluorescent moieties.

24. The system of claim 14, wherein the objective is a microscope objective.

25. The system of claim 14, wherein the plurality of wavelengths comprise wavelengths of 440 nm to 620 nm.

26. The system of claim 17, wherein the isosbestic point is between 405 nm to 420 nm.

27. The system of claim 22, wherein the image splitter is configured to: split the fluorescence emitted from each region to separate the fluorescence emitted by each of the one or more cellular activity-dependent fluorescent moieties; collect the separated fluorescence from each region via the second end of the same light conduit of the plurality of light conduits used to illuminate the region; and record a separate image for the fluorescence emitted by each of the one or more cellular activity-dependent fluorescent moieties, including each of the one or more terminal cross-sections at the first ends of all of the plurality of light conduits, using the image detector.

* * * * *